(12) United States Patent
Black et al.

(10) Patent No.: US 7,491,942 B2
(45) Date of Patent: Feb. 17, 2009

(54) SINGLE-USE INTERNAL DOSIMETERS FOR DETECTING RADIATION IN FLUOROSCOPY AND OTHER MEDICAL PROCEDURES/THERAPIES

(75) Inventors: Robert D. Black, Raleigh, NC (US); Steven R. Widener, Wake Forest, NC (US); John Carroll, Wake Forest, NC (US); Gregory Glenwood Mann, Raleigh, NC (US); Phillip M. Lehman, Raleigh, NC (US)

(73) Assignee: Sicel Technologies, Inc., Morrisville, NC (US)

( * ) Notice: Subject to any disclaimer, the term of this patent is extended or adjusted under 35 U.S.C. 154(b) by 789 days.

(21) Appl. No.: 10/865,312

(22) Filed: Jun. 10, 2004

(65) Prior Publication Data

US 2005/0010110 A1    Jan. 13, 2005

Related U.S. Application Data

(63) Continuation-in-part of application No. 10/303,591, filed on Nov. 25, 2002.

(60) Provisional application No. 60/334,580, filed on Nov. 30, 2001.

(51) Int. Cl.
*G01T 1/02* (2006.01)

(52) U.S. Cl. ................................. 250/370.07
(58) Field of Classification Search ............ 250/370.07
See application file for complete search history.

(56) References Cited

U.S. PATENT DOCUMENTS

| | | | |
|---|---|---|---|
| 3,229,684 A | 1/1966 | Nagumo et al. | 600/302 |
| 3,638,640 A | 2/1972 | Shaw | 128/2 R |
| 3,972,320 A | 8/1976 | Kalman | 128/2.1 A |
| 4,142,383 A | 3/1979 | Eberhart | |
| 4,163,380 A | 8/1979 | Masoner | 72/342 |
| 4,326,535 A | 4/1982 | Steffel et al. | 128/631 |
| 4,361,153 A | 11/1982 | Slocum et al. | 128/419 P |
| 4,397,313 A | 8/1983 | Vaguine | 128/399 |
| 4,397,314 A | 8/1983 | Vaguine | 128/399 |
| 4,416,283 A | 11/1983 | Slocum | 128/419 PG |
| 4,431,004 A | 2/1984 | Bessman et al. | 128/635 |
| 4,475,401 A | 10/1984 | Punia et al. | |

(Continued)

FOREIGN PATENT DOCUMENTS

DE     3219558 A1     1/1983

(Continued)

OTHER PUBLICATIONS

Halvorsen, H., *Dosimetric evaluation of a new design MOSFET in vivo dosimeter*, Med. Phys. 32 (1), Jan. 2005; pp. 110-117.

(Continued)

*Primary Examiner*—David P Porta
*Assistant Examiner*—Marcus H Taningco
(74) *Attorney, Agent, or Firm*—Myers, Bigel, Sibley & Sajovec, P.A.

(57) ABSTRACT

Methods, systems, devices, and computer program products include positioning single-use radiation internal dosimeters with MOSFETs into a patient to evaluate the radiation dose delivered during a medical procedure or treatment session. The MOSFETs can be unpowered during irradiation.

70 Claims, 36 Drawing Sheets

U.S. PATENT DOCUMENTS

| | | | |
|---|---|---|---|
| 4,484,076 A | 11/1984 | Thomson | 250/370.07 |
| 4,494,545 A | 1/1985 | Slocum et al. | 128/1.5 |
| 4,519,401 A | 5/1985 | Ko et al. | 118/748 |
| 4,523,279 A | 6/1985 | Sperinde et al. | 364/416 |
| 4,541,901 A | 9/1985 | Parker et al. | |
| 4,543,953 A | 10/1985 | Slocum et al. | 128/419 PT |
| 4,554,639 A | 11/1985 | Baker et al. | |
| 4,556,063 A | 12/1985 | Thompson et al. | 128/419 PT |
| 4,571,292 A | 2/1986 | Liu et al. | 204/412 |
| 4,571,589 A | 2/1986 | Slocum et al. | 128/419 PG |
| 4,575,676 A | 3/1986 | Palkuti | 324/158 D |
| 4,625,733 A | 12/1986 | Säynäjäkangas | 128/687 |
| 4,638,436 A | 1/1987 | Badger et al. | 364/414 |
| RE32,361 E | 2/1987 | Duggan | 128/696 |
| 4,642,463 A | 2/1987 | Thoms | |
| 4,651,741 A | 3/1987 | Passafaro | 128/633 |
| 4,655,880 A | 4/1987 | Liu | 204/1 T |
| 4,678,916 A | 7/1987 | Thomson | 250/370 |
| 4,681,111 A | 7/1987 | Silvian | 128/419 PT |
| 4,703,756 A | 11/1987 | Gough et al. | 128/635 |
| 4,719,919 A | 1/1988 | Marchosky et al. | 128/401 |
| 4,750,495 A | 6/1988 | Moore et al. | 128/419 PG |
| 4,769,547 A | 9/1988 | Uber, III | 250/374 |
| 4,793,825 A | 12/1988 | Benjamin et al. | 128/419 |
| 4,796,641 A | 1/1989 | Mills et al. | 128/748 |
| 4,804,847 A | 2/1989 | Uber, III | 250/370 F |
| 4,846,191 A | 7/1989 | Brockway et al. | 128/748 |
| 4,847,617 A | 7/1989 | Silvian | 340/970.16 |
| 4,900,422 A | 2/1990 | Bryan et al. | 204/401 |
| 4,913,153 A | 4/1990 | Hagmann et al. | |
| 4,919,141 A | 4/1990 | Zier et al. | 128/635 |
| 4,935,345 A | 6/1990 | Guilbeau et al. | 435/14 |
| 4,944,299 A | 7/1990 | Silvian | 128/419 PG |
| 4,958,645 A | 9/1990 | Cadell et al. | 128/903 |
| 4,961,422 A | 10/1990 | Marchosky et al. | 128/399 |
| 4,970,391 A | 11/1990 | Uber, III | 250/374 |
| 4,976,266 A | 12/1990 | Huffman et al. | 128/659 |
| 4,989,601 A | 2/1991 | Marchosky et al. | 128/399 |
| 5,008,546 A | 4/1991 | Mazziotta et al. | 250/366 |
| 5,012,411 A | 4/1991 | Policastro et al. | 364/413.06 |
| 5,074,318 A | 12/1991 | Campbell et al. | |
| 5,098,547 A | 3/1992 | Bryan et al. | 204/401 |
| 5,109,850 A | 5/1992 | Blanco et al. | 128/635 |
| 5,117,113 A | 5/1992 | Thomson et al. | 250/370.07 |
| 5,117,824 A | 6/1992 | Keimel et al. | 128/419 PG |
| 5,121,748 A | 6/1992 | Ditz et al. | |
| 5,126,937 A | 6/1992 | Yamaguchi et al. | 364/413.11 |
| 5,127,404 A | 7/1992 | Wyborny et al. | 128/419 P |
| 5,137,022 A | 8/1992 | Henry | 128/419 PT |
| 5,148,404 A | 9/1992 | Hilferink et al. | |
| 5,159,262 A | 10/1992 | Rumbaugh et al. | 324/765 |
| 5,163,380 A | 11/1992 | Duffy et al. | 119/15 |
| 5,166,073 A | 11/1992 | Lefkowitz et al. | 436/57 |
| 5,186,172 A | 2/1993 | Fiddian-Green | 128/632 |
| 5,193,538 A | 3/1993 | Ekwall | 128/419 PT |
| 5,197,466 A | 3/1993 | Marchosky et al. | 128/399 |
| 5,205,294 A | 4/1993 | Flach et al. | 128/696 |
| 5,215,887 A | 6/1993 | Saito | 435/14 |
| 5,264,843 A | 11/1993 | Silvian | 340/870 |
| 5,309,085 A | 5/1994 | Sohn | 324/71.5 |
| 5,314,450 A | 5/1994 | Thompson | 607/32 |
| 5,318,023 A | 6/1994 | Vari et al. | 128/653 |
| 5,324,315 A | 6/1994 | Grevious | 607/60 |
| 5,330,634 A | 7/1994 | Wong et al. | 204/409 |
| 5,354,314 A | 10/1994 | Hardy et al. | 128/653 |
| 5,354,319 A | 10/1994 | Wyborny et al. | 607/32 |
| 5,355,880 A | 10/1994 | Thomas et al. | 128/633 |
| 5,372,133 A | 12/1994 | Hogen et al. | 128/631 |
| 5,377,676 A | 1/1995 | Vari et al. | 128/634 |
| 5,383,909 A | 1/1995 | Keimel | 607/5 |
| 5,400,382 A | 3/1995 | Welt et al. | |
| 5,425,361 A | 6/1995 | Fenzlein et al. | 128/635 |
| 5,431,171 A | 7/1995 | Harrison et al. | 128/698 |
| 5,444,254 A | 8/1995 | Thomson | 250/370.07 |
| 5,466,246 A | 11/1995 | Silvian | 607/32 |
| 5,470,345 A | 11/1995 | Hassler et al. | 607/36 |
| 5,476,488 A | 12/1995 | Morgan et al. | 607/30 |
| 5,476,634 A | 12/1995 | Bridges et al. | |
| 5,477,050 A | 12/1995 | Kronenberg et al. | |
| 5,480,415 A | 1/1996 | Cox et al. | 607/32 |
| 5,481,262 A | 1/1996 | Urbas et al. | 340/870.17 |
| 5,497,772 A | 3/1996 | Schulman et al. | 128/635 |
| 5,505,828 A | 4/1996 | Wong et al. | 205/777.5 |
| 5,507,786 A | 4/1996 | Morgan et al. | 607/27 |
| 5,517,313 A | 5/1996 | Colvin, Jr. | 356/417 |
| 5,535,752 A | 7/1996 | Halperin et al. | 128/670 |
| 5,538,005 A | 7/1996 | Harrison et al. | 128/698 |
| 5,543,111 A | 8/1996 | Bridges et al. | |
| 5,545,187 A | 8/1996 | Bergstrom et al. | 607/31 |
| 5,549,113 A | 8/1996 | Halleck et al. | 128/633 |
| 5,549,654 A | 8/1996 | Powell | 607/25 |
| 5,556,421 A | 9/1996 | Prutchi et al. | 607/36 |
| 5,557,702 A | 9/1996 | Yoshikawa et al. | 385/143 |
| 5,562,713 A | 10/1996 | Silvian | 607/32 |
| 5,564,434 A | 10/1996 | Halperin et al. | 128/675 |
| 5,571,148 A | 11/1996 | Loeb et al. | |
| 5,572,027 A | 11/1996 | Tawil et al. | |
| 5,572,996 A | 11/1996 | Doiron et al. | 128/633 |
| 5,591,217 A | 1/1997 | Barreras | 607/5 |
| 5,593,430 A | 1/1997 | Renger | 607/9 |
| 5,596,199 A | 1/1997 | McNulty et al. | 250/370.07 |
| 5,606,163 A | 2/1997 | Huston et al. | 250/337 |
| 5,609,820 A | 3/1997 | Bridges et al. | |
| 5,620,472 A | 4/1997 | Rahbari | 128/903 |
| 5,620,475 A | 4/1997 | Magnusson | 607/30 |
| 5,620,479 A | 4/1997 | Diederich | 607/97 |
| 5,626,630 A | 5/1997 | Markowitz et al. | 607/60 |
| 5,626,862 A | 5/1997 | Brem et al. | 424/426 |
| 5,628,324 A | 5/1997 | Sarbach | 128/670 |
| 5,630,413 A | 5/1997 | Thomas et al. | 128/633 |
| 5,637,876 A | 6/1997 | Donahue et al. | |
| 5,656,815 A | 8/1997 | Justus et al. | 250/337 |
| 5,656,998 A | 8/1997 | Fujiuchi et al. | |
| 5,681,611 A | 10/1997 | Yoshikawa et al. | 427/163.2 |
| 5,682,888 A | 11/1997 | Olson et al. | 128/653.1 |
| 5,720,771 A | 2/1998 | Snell | 607/60 |
| 5,731,957 A | 3/1998 | Brennan | |
| 5,732,704 A | 3/1998 | Thurston et al. | 128/659 |
| 5,744,094 A | 4/1998 | Castberg et al. | |
| 5,744,804 A | 4/1998 | Meijer et al. | 250/369 |
| 5,744,805 A | 4/1998 | Raylman et al. | 250/370.01 |
| 5,759,199 A | 6/1998 | Snell et al. | 607/60 |
| 5,787,144 A | 7/1998 | Findlay | |
| 5,791,344 A | 8/1998 | Schulman et al. | 128/635 |
| 5,811,814 A | 9/1998 | Leone et al. | 250/368 |
| 5,814,089 A | 9/1998 | Stokes et al. | 607/32 |
| 5,833,603 A | 11/1998 | Kovacs et al. | 600/317 |
| 5,840,148 A | 11/1998 | Campbell et al. | 156/275.5 |
| 5,847,391 A | 12/1998 | Sephton | |
| 5,855,203 A | 1/1999 | Matter | |
| 5,857,463 A | 1/1999 | Thurston et al. | 128/659 |
| 5,879,375 A | 3/1999 | Larson et al. | 607/30 |
| 5,891,179 A | 4/1999 | Er et al. | 607/27 |
| 5,916,167 A | 6/1999 | Kramer et al. | 600/436 |
| 5,918,110 A | 6/1999 | Abraham-Fuchs et al. | 438/48 |
| 5,928,150 A | 7/1999 | Call | 600/436 |
| 5,932,879 A | 8/1999 | Raylman et al. | 250/370.06 |
| 5,939,453 A | 8/1999 | Heller et al. | 514/452 |
| 5,949,075 A | 9/1999 | Kishi | |
| 5,987,350 A | 11/1999 | Thurston | 600/436 |
| 6,001,067 A | 12/1999 | Shults et al. | |
| 6,015,390 A | 1/2000 | Krag | 600/549 |
| 6,025,137 A | 2/2000 | Shyjan | 435/6 |
| 6,031,454 A | 2/2000 | Lovejoy et al. | |

| | | |
|---|---|---|
| D423,377 S | 4/2000 | Atterbury et al. ............. D10/47 |
| 6,047,214 A | 4/2000 | Mueller et al. ................. 607/61 |
| D424,453 S | 5/2000 | Atterbury et al. ............ D10/47 |
| 6,070,096 A | 5/2000 | Hayashi ....................... 600/477 |
| 6,076,009 A | 6/2000 | Raylman et al. ............. 600/436 |
| 6,087,666 A | 7/2000 | Huston et al. ............. 250/484.5 |
| 6,093,381 A | 7/2000 | Triozzi et al. .............. 424/1.49 |
| 6,099,821 A | 8/2000 | Rich et al. .................. 424/1.61 |
| 6,119,697 A * | 9/2000 | Engel et al. .................. 128/885 |
| 6,132,681 A | 10/2000 | Faran et al. |
| 6,172,368 B1 | 1/2001 | Tarr et al. .............. 250/370.07 |
| 6,177,677 B1 | 1/2001 | Alboresi et al. |
| 6,219,573 B1 | 4/2001 | Pompei |
| 6,239,724 B1 | 5/2001 | Doron et al. ........... 340/870.28 |
| 6,240,312 B1 | 5/2001 | Alfano et al. ............... 600/478 |
| 6,242,741 B1 | 6/2001 | Miller et al. ........... 250/363.02 |
| 6,259,095 B1 | 7/2001 | Bouton et al. ............. 250/336.1 |
| 6,272,373 B1 | 8/2001 | Bouton ....................... 600/436 |
| 6,274,159 B1 | 8/2001 | Marotta et al. .............. 424/426 |
| 6,295,680 B1 | 10/2001 | Wahl et al. ....................... 14/1 |
| 6,304,766 B1 | 10/2001 | Colvin, Jr. .................. 600/317 |
| 6,363,940 B1 | 4/2002 | Krag .......................... 128/899 |
| 6,398,710 B1 | 6/2002 | Ishikawa et al. ............... 600/3 |
| 6,402,689 B1 | 6/2002 | Scarantino et al. |
| 6,444,475 B1 | 9/2002 | Anderson, Jr. et al. ...... 436/161 |
| 6,614,025 B2 | 9/2003 | Thomson et al. ....... 250/370.01 |
| 6,650,930 B2 | 11/2003 | Ding .......................... 600/436 |
| 6,746,465 B2 | 6/2004 | Diederich et al. |

FOREIGN PATENT DOCUMENTS

| | | |
|---|---|---|
| DE | 3332075 A1 | 3/1984 |
| DE | 4341903 A1 | 6/1995 |
| EP | 0364045 A1 | 10/1989 |
| EP | 0420177 A1 | 3/1991 |
| EP | 0471957 A2 | 2/1992 |
| EP | 0537761 A2 | 4/1993 |
| EP | 0245073 B1 | 12/1993 |
| EP | 0386218 B1 | 10/1996 |
| GB | 2263196 A | 7/1993 |
| JP | 02147882 | 6/1990 |
| JP | 07306269 | 11/1995 |
| JP | 63221278 | 9/1998 |
| SU | 414900 | 7/1976 |
| SU | 1603314 | 10/1990 |
| WO | WO95/17809 | 7/1995 |
| WO | WO97/33513 | 9/1997 |
| WO | WO98/02209 | 1/1998 |
| WO | WO98/05965 | 2/1998 |
| WO | WO98/43701 | 10/1998 |
| WO | WO98/58250 | 12/1998 |
| WO | WO99/48419 | 9/1999 |
| WO | WO99/58065 | 11/1999 |
| WO | WO99/63881 | 12/1999 |
| WO | WO00/29096 | 5/2000 |
| WO | WO00/18294 | 6/2000 |
| WO | WO00/33065 | 6/2000 |
| WO | WO00/40299 | 7/2000 |
| WO | WO01/22874 A1 | 4/2001 |
| WO | WO02/09775 A2 | 2/2002 |
| WO | WO02/39917 A1 | 5/2002 |
| WO | WO02/39918 A1 | 5/2002 |
| WO | WO02/86449 A2 | 10/2002 |
| WO | WO02/100485 A1 | 12/2002 |
| WO | WO03/047694 A2 | 6/2003 |

OTHER PUBLICATIONS http://www.thomson-elec.com/linearrray.htm, *Linear Array, Linear 5ive MOSFET Array*, Thomson/Nielsen Monitoring radiation in this world and beyond... Dated Feb. 16, 2005, 5 sheets.

http://www.thomson-elec.com/buildupcaps.htm, *Build-up Caps, Hemispherical Build-up Caps*, Thomas/Nielsen Monitoring radiation in this world and beyond... © 2004, 1 sheet.

http://www.cirsinc.com/products/model_plasticwater.html, *Plastic Water™, Calibrate photon and electron beams with 0.5% of true water dose*, Computerized Imaging reference Systems, Inc., © 2001, 1 sheet.

European Search Report for Application No. 02784637.7; date of mailing Sep. 15, 2006.

Akin et al. *RF Telemetry Powering and Control of Hermetically Sealed Integrated Sensors and Actuators*, Digest, IEEE Solid-State Sensors and Actuators Workshop, pp. 145-148, Hilton head, SC, Jun. 1990.

Akin et al. *An implantable multichannel digital neural recording system for a micromachined sieve electrode*, Proc. Int. Conf. on Solid-State Sensors and Actuators, Stockholm, Sweden, vol. 1, pp. 51-54 (jun. 1995).

Alecu et al., *Dose perturbations due to in vivo dosimetry with diodes* Radiotherapy and Oncology, pp. 289-291, vol. 42, (1997).

Almond et al., *AAPM's TG-51 protocol for clinical reference dosimetry of high-energy photon and electron beams*, Med. Phys. 26 (9), pp. 1847-1870, (Sep. 1999).

Barber et al., *Comparison of NaI(Tl), CdTe, and HgI2 surgical probes: physical characterization*, Med. Phys., 18(3):373-381 (May-Jun. 1991).

Barthe, Jean, *Electronic dosimeters based on solid state detectors*, Nuclear, Instruments. and Methods in Physics Research Sec. B vol. 184, pp. 158-189 (2001).

Bergh, Van Den, H., *On the Evolution of Some Endoscopic Light Delivery Systems for Photodynamic Therapy*, Endoscopy, May 1998, pp. 392-407.

Berthold et al., *Method for in-situ detection of tritium in water*, McDermott technology Inc./RDTPA 99-03, pp. 1-9 (Sep. 19-22, 1999).

Biotelemetrics, Inc., 6520 Contempo Lane, Boca Raton, Florida 33433, Tel: 407-394-0315. Biotelemetry Page, http://biotelemetrics.com/telemtry html retrieved Oct. 20, 2004.

Blackstock et al., *Tumor retention of 5-fluorouracil following irradiation observed using 19F nuclear magnetic resonance spectroscopy*, Init J Radiat Oncol Biol Phys, 36(3):641-648 (Oct. 1, 1996).

Bojsen et al., *A portable external two-channel radiotelemetrical GM-detector unit, for measurements of radionuclide-tracers in vivo*, Int J Appl Radiat Isot, 25(4):161-166 (Apr. 1974).

Bojsen et al., *A radiotelemetrical measuring device, implantable on animals, for long term mersurements of radionuclide tracers*, Int J Appl radiat Isot, 23(11):505-511 (Nov. 1972).

Braichotte et al., *Clinical Pharmacokinetic Studies of Photofrin by Fluorescence Spectrscopy in the Oral Cavity, the Esophagus, and the Bronchi*, Cancer, vol. 75, No. 11, Jun. 1, 1995, pp. 2768-2778.

Brochure, *Be as smart as you can be with BMDS and Smart Alec™ your partners in intelligence*, Bio Medic Data Systems, Inc. (© 1999).

Brochure, *Come along for the incredible journey in the development of the IPTT-200*, Bio Medic Data Systems, Inc. (© 2000).

Butson, et al, *A new radiotherapy surface dose detector: The MOSFET*, Medical Physics, American Institute of Physics, vol. 23 (5) pp. 655-658 (May 1996).

Cortese et al., *Clinical Application of a New Endoscopic Technique for Detection of In Situ Bronchial Carcinoma*, May Clinic Proceedings, vol. 54, Oct. 1979, pp. 635-641.

Cosofret et al., *Microfabricated sensor array sensitive to pH and K+ for ionic distribution measurements in the beating heart, Analytical Chemistry*, vol. 67, pp. 1647-1653 (1995).

Daghighian et al., *Intraoperative beta probe: a device for detecting tissue labeled with positron or electron emitting isotopes during surgery*, Med Phys, 21(1):153-157 (Jan. 1994).

Data Sciences International, http://www ispex ca/companies/instrumentation/DataScInt html, Profile web pp. 1-2 and Instrumental Products 1-7, Copyright Ispex Exchange Inc., 2003, for examination purposes, applicant admits its similar devices were available prior to earlier filing date of application.

Demidecki et al., *Considerations on the calbration of small thermoluminescent dosimeters used for measurement of beta particle absorbed doses in liquid environments*, Med. Phys. 20 (4), pp. 1079-1087, (Jul./Aug. 1993).

Deutsch, S., *Fifteen-electrode time-multiplex EEG telemetry from ambulatory patients*, IEEE Transactions on Biomedical Engineering, vol. BME-26, pp. 153-159 (1979).

Dewhirst et al., *Soft-Tissue Sarcomas: MR Imaging and MR Spectroscopy for Prognosis and Therapy Monitoring*, Radiology, 174:847-853 (1990).

Dewhirst, *Concepts of oxygen transport at the microcirculatory level*, Seminars in Radiation Oncology, vol. 8, 1998, pp. 143-150.

Dienes et al., *Radiation Effects in Solids, Interscience Monographs in Physics and Astronomy*, vol. II, Intersicence Publishers, Inc., pp. 1-4, 56-85, 90-122 and 129-177 (© 1957).

Dimitrakopoulou et al., *Studies with Positrons Emission Tomography After Systemic Administration of Fluorine-18-Uracil in Patients with Liver Metastases from Colorectal Carcinoma*, J Nucl Med, 34:1075-1081 (Jul. 1993).

Essers, M. et al., "In Vivo Dosimetry During External Photon Beam Radiotherapy", Int. J. Radiation Oncology Biol. Phys., vol. 43, No. 2, pp. 245-259, (1999).

Farrar IV Harry et al., *Gamma-Ray Dose Mapping in Operational Candu Reactor Containment Areas Using MOS Dosimeters*, pp. 441-446, Reactor Dosimetry, ASTM, 1994.

Fernald, *A microprocessor-based system for the fast prototyping of implantable instruments for biomedical research applications*, Doctoral Dissertation, Elect. & Computer Eng., NC State Univ., (1992).

Fernald, K., T. Cook, T. Miller, III, J. Paulos, *A microprocessor-based implantable telemetry systems*, Computer, vol. 24, No. 7, pp. 23-30 (1991).

Fisher, DR, *Radiation dosimetry for radioimmunotherapy. An overview of current capabilities and limitations*, Cancer, 73(3 Suppl):905-911 (Feb. 1, 1994).

Fryer, T., H. Sandler, W. Freund, E. McCutcheon, E. Carlson, *A multichannel implantable telemetry system for flow, pressure, and ECG measurements*, Jour. of Applied Physiology, vol. 39, pp. 318-326 (1973).

Gelezunas et al., *Silicon avalanche radiation detectors: the basis for a new ini vivo radiation detection probe*, Eur J Nucl Med, 8(10):421-424 (1983).

Gerweck, *Tumor pH: Implications for Treatment and Novel Drug Designs*, 8 Seminars in Radiation Oncology, No. 5, pp. 176-182 (Jul. 1998).

Gilligan et al., *Evaluation of a subcutaneous glucose sensor out to 3 months in a dog model*, Diabetes Care, vol. 17, pp. 882-887 (1994).

Gladstone et al., *A miniature MOSFET radiation dosimeter probe*, Med. Phys. 21 (11), pp. 1721-1728, (Nov. 1994).

Gladstone et al., *Real-Time, In Vivo Measurement of Radiation Dose during Radioimmunotherapy in Mice Using a Miniature MOSFET Dosimeter Probe*, Radiation Research 141, pp. 330-335 (1997).

Gratz et al., *Smart card for detection of alpha radiation sensors and actuators* 61 pp. 431-435 (1997).

Griffiths et al., *The OxyLite: a fibre-optic oxygen sensor*, British J. of Radiology, vol. 72, pp. 627-630 (1999).

Gschwend, S., J. Knutti, H. Allen, J. Meindl, *A general-purpose implantable multichannel telemetry system for physiologica research*, Biotelemetry Patient Monitoring, vol. 6, pp. 107-117 (1979).

Hamburger et al, *Primary Bioassay of Human Tumor Stem Cells*, Science, 197:461-463 (1977).

Hansen, B., K. Aabo, J. Bojsen, *An implantable, externally powered radiotelemetric system for long-term ECG and heart-rate monitoring*, Biotelemetry Patient Monitoring, vol. 9, pp. 228-237 (1982).

Hassan et al., *A radiotelemetry pill for the measurement of ionizing radiation using a mercuric iodide detector*, Phys med Biol, 23(2):302-308 (Mar. 1978).

Heij et al., *Intraoperative search for neuroblastoma by MIBG and radioguided surgery with the gamma detector*, Med Pediatr Oncol, 28(3):171-174 (Mar. 1997).

Hines et al. *Advanced Biotelemetry Systems for Space Life Sciences: PH Telemetry*, Biotelementry XIII, March 26-31, pp. 131-137 (1995).

Hirsch et al., *Early Detection of Lung Cancer: Clinical Perspectives of Recent Advances in Biology and Radiology*, Clinical Cancer Research, vol. 7, Jan. 2001, pp. 5-22.

Hoffman et al., *Intraoperative probes and imaging probes*, Eur Jnl Nucl Med, 26(8):913-935 (Aug. 1999).

Holmstrom et al. *Long-term in vivo experience of an electrochemical sensor using the potential step technique for measurement of mixed venous oxygen pressure*, Biosensors & Bioelectronics, 13, pp. 1287-1295 (1998).

Jornet et al., *Calibration of semiconductor detectors for dose assessment in total body irradiation*, Radiotherapy and Oncology, pp. 247-251, vol. 38, (1996).

Kastrissios et al., *Screening for Sources of Interindividual Pharmacokinetic Variability in Anticancer Drug Therapy: Utility of Population Analysis*, Cancer Investigation, 19(1):57-64 (Jan. 30, 2001).

Kern, D.H., *tumor Chemosensitivity and chemoresistance Assays*, Cancer 79(7):1447-1450 (1997).

Khouri et al., *An implantable semiconductor beta-radiation detector*, Am J Physiol, 232(1):H95-98 (Jan. 1977).

Kinsey et al. *Endoscopic System for Simultaneous Visual Examination and Electronic Detection of Fluorescence*, Review of Scientific Instruments, vol. 51, No. 10, Oct. 1980, pp. 1403-1403.

Kissel et al. *Noninvasive determination of the arterial input function of an anticancer drug from dynamic PET scans using the population approach*, Med Phys 26(4):609-615 (Apr. 1999).

Kolbert et al. *Implementation and Evaluation of Patient-Specific Three-Dimensional Internal Dosimetry*, Journal of Nuclear Medicine, vol. 38, No. 2, pp. 301-307, (Feb. 7, 1996).

Konigsberg Instruments, Inc., http://guide.labanimal.com/guide/companydjsp?b=3930, Lab Animal p. 1, Product Catergories p. 1, Lab Animal Buyers Guide 2003 p. 1 and Animal Research Equipment pp. 1-12, Nature Publishing Group, 2003, for examination purposes, applicant admits similar devices were available prior to earlier filing date of application.

Koutcher et al., *Potentiation of a Three Drug Chemotherapy Regiment by Radiation*, Cancer Res, 53:3518-3523 (1993).

Kulapaditharom et al., *Performance characteristics of fluorescence Endoscope in Detection of Head and Neck Cancers*, Annals of Ontology, Rhinology & Laryngol, vol. 110 (1), Jan. 2001, pp. 45-52.

Lambrechts et al. *Biosensors: Microelectrochemical Device*, NY, NY: IOP Publishing Ltd., pp. 206-208 (1992).

Leichner et al. *Patient-Specific Dosimetry of Indium-111- and Yttrium-90-Labeled Monoclonal antibody CC49*, Journal of Nuclear Medicine, vol. 38, No. 4, pp. 5122-516, (Apr. 1997).

Liu et al., *A Radionuclide Therapy Treatment Planning and Dose Estimation System*, The Journal of Nuclear Medicine, vol. 40, No. 7, pp. 1151-1153, (Jul. 1999).

Loeb et al., *Injectable microstimulator for functional electrical stimulation*, Med. & Biol. Eng. & Comput., vol. 29, pp. NS13-NS19, (1991).

Lowe, S., et al., *p53 status and the efficacy of cancer therapy in vivo*, Sci., vol. 266, pp. 807-810 (1994).

Ma et al., *The photosensitizing effect of the photoproduct of protoporphyrin IX*, J. Photochem Photobiol B, Jul. 2001, vol. 60 (2-3), pp. 108-113.

Mackay et al. *Gamma-Ray Dose Mapping in Operational Candu Reactor Containment Areas Using MoS Dosimeters*, pp. 441-446, Reactor Dosimetry, ASTM, 1994.

Mackay, *Bio-Medical Telemetry, Sensing and Transmitting Biological Information from Animals and Man*, Second edition. New York, NY: IEEE Press (1993).

Marzouk et al., *Electrodeposited Iridium Oxide pH Electrode for Measurement of Extracellular Myocardial Acidosis during Acute Ischemia*, Anal. Chem., vol. 70, pp. 5054-5061 (1998).

Mathur, V.K, *Ion storage dosimetry*, Nuclear Instruments and Methods in Physics Research B, vol. 184 pp. 190-206 (2001).

Mayinger et al., *Endoscopic Fluorescence Spectroscopy in the Upper GI Tract for the Detection of GI Cancer: Initial Experience*, The American Journal of Gastroenterology, vol. 96, No. 9, Sep. 2001, pp. 2616-2621.

Mayinger et al., *Light-induced Autofluorescence Spectroscopy for the Endoscopic Detection of Esophageal Cancer*, Gastrointestinal Endoscopy, vol. 54, No. 2, Aug. 2001, pp. 195-201.

Messenger et al., *The Effects of Radiation on Electronic systems*, Van Nostrand Reinhold, pp. 332-349 (1992).

Miller et al., *Clinical Molecular Imaging*, J Amer Coll Radiol 2004, 1, pp. 4-23.

Mittal et al., *Evaluation of an Ingestible Telemetric Temperature Sensor for Deep Hyperthermia Applications*, Int. J. Radiation Oncology Biol. Phys., vol. 21, pp. 1353-1361 (1991).

Moreno, D.J. et al, *A Simple Ionizing Radiation Spectrometer/Dosimeter based on Radiation Sensing Field Effect Transistors (RadFETs)* Transducers '97 International Conference on Solid-State Sensors and Actuators Chicago, pp. 1283-1286 (Jun. 16-19, 1997).

Mueller et al. *Feasibility of inductive powering of miniature low-power biotelemetry for use with microfabricated biomedical sensors*, Proc. Biotelemetry XIII, Williamsburg, VA, March., pp. 372-377 (1995).

Myeck et al., *Colonic polyp differentiation using time-resolved autofluorescence spectroscopy*, Gastrointest. Endosc., Oct. 1998, No. 48 (4), pp. 390-394.

National Aeronautics and Space Administration, *Extravehicular Activity Radiation Monitoring (EVARM)*, Fact Sheet FS 2001-11-191-MSFC, abstract review, 10/01.

Nardin et al., *A multichannel neuromuscular microstimulator with bidirectional telemetry*, Proc. Int. Conf. on Solid-State Sensors and Actuators, Stockholm, Sweden, vol. 1, pp. 59-62 (Jun. 1995).

Olthuis et al. *Simplified design of the coulometric sensor-actuator system by the application of a time-dependent actuator current*, Sensors and Actuators B, vol. 7, pp. 479-483 (1992).

Oshima et al, *Development of Micro-Telemetering Multi-Sensor Capsule System with newly developed LSI for the clinical applications*, Transducers '87, The 4$^{th}$ International Conference on Solid-State Sensors and Actuators, pp. 163-166 (1987).

Pauley et al. *A microminiature hybrid multichannel implantable biotelemetry system*, Biotelemetry Patient Monitoring, vol. 8, pp. 163-172 (1981).

PCT International Search Report, International Application No. PCT/US01/47373 dated Aug. 6, 2002.

PCT International Search Report, International Application No. PCT/US02/12855 dated Dec. 16, 2002.

PCT International Search Report, International Application No. PCT/US02/38111.

Peet, D.J. *Evaluation of a MOSFET radiation sensor for the measurement of entrance surface dose in diagnostic radiology*, The British Journal of Radiology, 72:562-568 Jun. 1993.

Pendower, J., *Spontaneous Disappearance of Gall-stones*, Medical Memoranda, British Medical Journal, vol. 2, p. 492, 1964.

Piwnica-Worms et al., *Functional Imaging of Multidrug-resistant P-Glycoprotein with an Organotechnitium Complex*, Cancer Res, 53:977-984 (1993).

Presant et al., *Enhancement of Fluorouracil Uptake in Human Colorectal and Gastric Cancers by Interferon or by High-Dose Methotrexate: An In Vivo Human Study Using Noninvasive$^{19}$F-Magnetic Resonance Spectroscopy*, J Clin Oncol, 18:255-261 (2000) Jan. 4, 1999.

Presant et al., *Human tumor fluorouracil trapping: clinical correlations of in vivo 19F nuclear magnetic resonance spectroscopy pharmacokinetics*, J Clin Oncol, 8(11): 1868-1873 (Nov. 1990).

Puers, B., P. Wouters, M. DeCooman, *A low power multi-channel sensor interface for use in digital telemetry*, Sensors and Actuators A, vols. 37-38, pp. 260-267 (1993).

Ranii, D., N&O Article, *Company's device aims to monitor disease from inside*. Mar. 30, 2000.

Ranii, D., N&O Article, *Sicel seeks go-ahead for clinical trials*. Apr. 17, 2002.

Raylman et al., *Evaluation of ion-implanted-silicon detectors for use in intraoperative positron-sensitive probes*, Med Phys, 23(11): 1889-1895 (Nov. 1996).

Reece M.H. et al., *Semiconductor Mosfet Dosimetery*, Health Physics Society annual Meeting, pp. 1-14, 1988.

Rollins et al., *Potential new endocscopic techniques for the earlier diagnosis of pre-malignancy*, Best Pract. Res. Clin. Gastroenterol, Apr. 2001, vol. 15 (2), pp. 227-247.

Schantz et al, *In vivo native cellular fluorescence and histological characteristics of head and neck cancer*, Clin. Cancer Res., May 1998, vol. 4 (5), pp. 1177-1182.

Shani, Gad, *Radiation Dosimetry Instrumentation and Methods*, CRC Press, Boca Raton, Florida, 5 sheets including Table of Contents (1991).

Shortt, Dr. Ken et al., *A New Direct Reading Extremity Dosimeter—How the ED-1 Sensor Works*, Health Physics Society Annual Meeting, Jul. 1994.

Siegal et al., *MIRD Pamphlet No. 16: Techniques for Quantitative Radiopharmaceutical Biodistribution Data cquisition and Analysis for Use in Human Radiation Dose Estimates*, Journal of Nuclear Medicine, 40-27S-61S (1999).

Siegal et al., *The Importance of Patient-Specific Radiation Dose Calculations for the Aministration of Radionuclides in Therapy*, Cellular and Molecular Biology 48 (5), pp. 451-459 (Mar. 1, 2002).

Small Business Innovation Research Program Phase One Grant Application entitled *An Implantable Multi-channel System for Monitoring Tumors*, submitted on or about Dec. 1996 to U.S. Public Health Service.

Small Business Innovation Research Program Phase One Grant Application entitled *An Implantable Multi-channel System for Monitoring Tumors*, resubmitted on or about Aug. 1997 to the National Institute of Health.

Small Business Innovation Research Program Phase One Grant Application entitled *An Implantable Multi-channel System for Monitoring Tumors*, resubmitted to the U.S. funding authority on or about Apr. 1998.

Soubra, M. et al., *Evaluation of a dual bias metal oxide-silicon semiconductor field effect transistor detector as radiation dosimeter*, American Assoc. Phys. Med., vol. 21, No. 4, pp. 567-572, Apr. 1994.

Stabin, M. G., *Internal Radiation Dosimetry*, Nuclear Medicine, Part Two, The Scientific Basis of Nuclear Medicine, pp. 316-333 (1996).

Stenson et al., *Effects of implantable biomaterials on radiation dosimetry*, Head Neck, vol. 19, No. 5 pp. 384-390 (Aug. 1997).

Stepp et al., *Fluorescence endoscopy of gastrointestinal diseases: basic principles, techniques, and clinical experience*, Endoscopy, May 1998, vol. 30 (4), pp. 379-386.

Stevens et al., *5-Flourouracil metabolism monitored in vivo by $^{19}F$ NMR*, Br J Cancer, 50:113-117 (1984).

Sweeney et al., *Visualizing the kinetics of tumor-cell clearance in living animals*, PNAS, vol. 96, No. 21, pp. 12044-12049, Oct. 12, 1999.

Tarr, N.G. et al., *A Floating Gate MOSFET Dosimeter Requiring No External Bias Supply*, Redecs 97. Fourth European Conference on Radiation and Its Effects on Components and Systems (Cat. No. 97$^{TH}$8294), pp. 277-281 (1998).

Taylor et al., *The Forces in the Distal Femur and the Knee During Walking and Other Activities Measured by Telemetry*, J. of Anthroplasty, vol. 13, No. 4, pp. 428-437 (1998).

Thomson et al., *Radiation Dosimetry with MOS Sensors*, Radiation Protection Dosimetry, Viol. 6, No. 1-4, Nuclear Technology Publishing, pp. 121-124, 1984.

UCL Christian de Duve Institute of Cellular Pathology, Ludwig Institute for Cancer Research, URL www.Icp.ucl.ac.be/report95/licr95.html (1995).

Von Hoff et al., *Selection of Cancer Chemotherapy for a Patient by an In Vitro Assay Versus a Clinician*, JNCI 82:110-116 (1990) Oct. 25, 1989.

Watanabe et al., *A Preliminary Report on Continuous Recording of Salivary pH Using Telemetry in an Edentulous Patient*, Int'l J. Prosthodontics, vol. 12, No. 4, pp. 313-317 (1999).

Wayne, E. et al., *Treatment of Thyroid Disorders*, To-day's Drugs, British Medical Journal, pp. 493-496, Aug. 22, 1964.

Webster, Editor, *Design of Cardiac Pacemakers*, New York, NY: IEEE Press, pp. 155-157 (1995).

Williams et al., *Multipurpose chip for physiological measurements*, IEEE International Symposium on Circuits and Systems, vol. 4, pp. 255-258, Proc. (1994).

Wolf et al., *19F-MRS studies of fluorinated drugs in humans*, Adv Drug Deliv Rev, 41(1):55-74 (Mar. 15, 2000).

Wolf et al., *Non-invasive 19F-NMRS of 5-fluorouracil in pharmacokinetics and pharmacodynamic studies*, NMR Biomed 11(7):380-387 (Nov. 1998).

Wolf et al., *Potential of microsensor-based feedback bioactuators for biophysical cancer treatment*, Biosensors & Bioelectronics, vol. 12, pp. 301-309 (1997).

Wolf et al., *Tumor trapping of 5-fluorouracil: In vivo $^{19}F$ NMR spectroscopic pharmacokinetics in tumor-bearing humans and rabbits*, Proc Natl Acad Sci USA, 87:492-496 (Jan. 1990).

Woolfenden et al., *Radiation detector probes for tumor localization using tumor-seeking radioactive tracers*, AJR Am J Roentgenol, 153(1): 35-39 (Jul. 1989).

Wouters et al., *A Multi-purpose CMOS sensor interface for low-power applications*, IEEE Journal of Solid-State Circuits, vol. 29, No. 8, pp. 952-956 (Aug. 1994).

Yang et al., *Visualizing gene expression by whole-body fluorescence imaging*, PNAS, vol. 97, No. 22, pp. 12278-12282, Oct. 24, 2000.

Yarnell et al., *Drug Assays on Organ Cultures of Biopsies from Human Tumours*, Br Med J 2:490-491 (1964).

Young et al. *Cell cycle characteristics of human solid tumors in vivo*, Cell Tissue Kinetics, vol. 3, pp. 285-290 (1970).

Zanzonico et al. *The intraoperative gamma probe: basic principles and choices available*, Semin Nucl Med 30 (1): 33-48 (Jan. 2000).

Zonios et al. *Diffuse reflectance spectroscopy of human adenomatous colon polyps in vivo*, Applied Optics, Nov. 1999, vol. 1; 38 (31), pp. 6628-6637.

Zuckier et al., *Remotely Pollable Geiger-Muller Detector for Continuous Monitoring of Iodine-131 Therapy Patients*, J. of Nuclear Med., vol. 39, No. 9, pp. 1558-1562 (Sep. 1998).

Akabani, Gamal, *Absorbed Dose Calsulations in Haversian Canals for Several Beta-Emitting Radionuclides*, Journal of Nuclear Medicine; 34:1361-1366, (1993).

Loncol et al., *Entrance And Exit Dose Measurements With Semiconductors And Thermoluminescent Dosemeters: A Comparison Of Methods And In Vivo Results*, Radiotherapy and Oncology, pp. 179-187, vol. 41, (1996).

Ma et al., in *Ionizing Radiation Effects in MOS Devices and Circuits*, John Wiley & Sons, pp. 35-46 (1989).

* cited by examiner

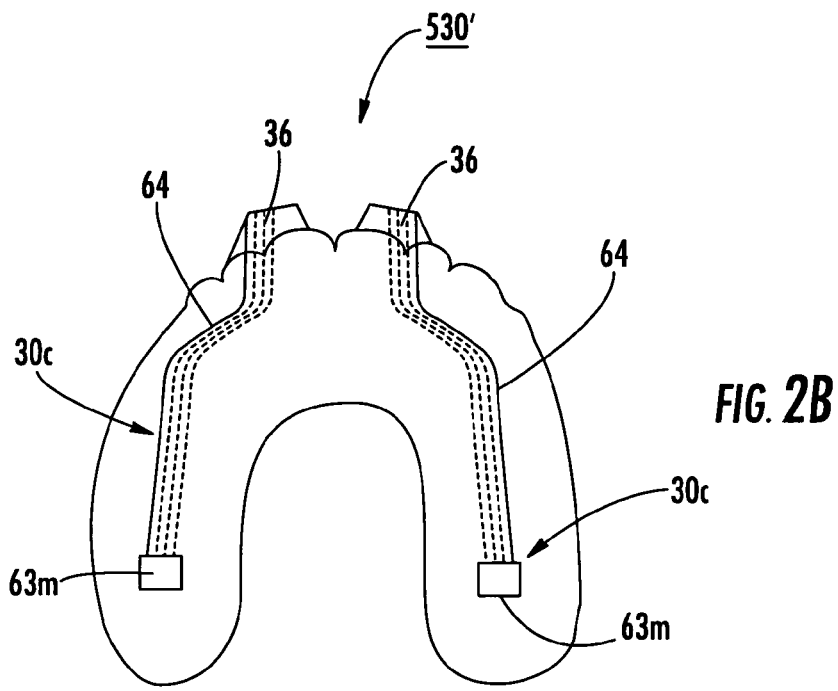
*FIG. 2B*
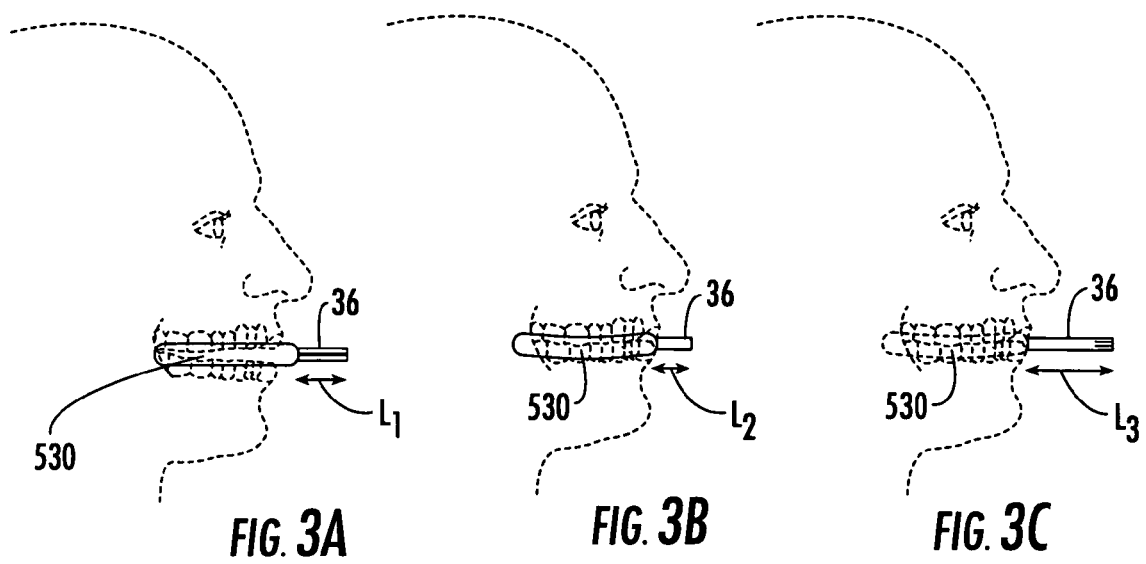
*FIG. 3A*  *FIG. 3B*  *FIG. 3C*

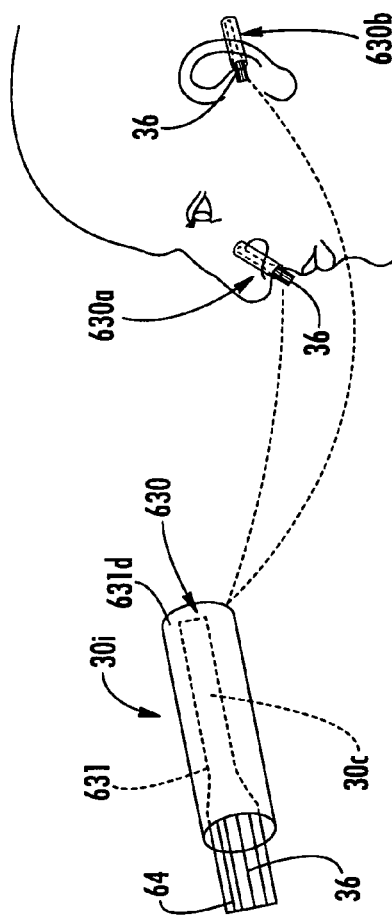
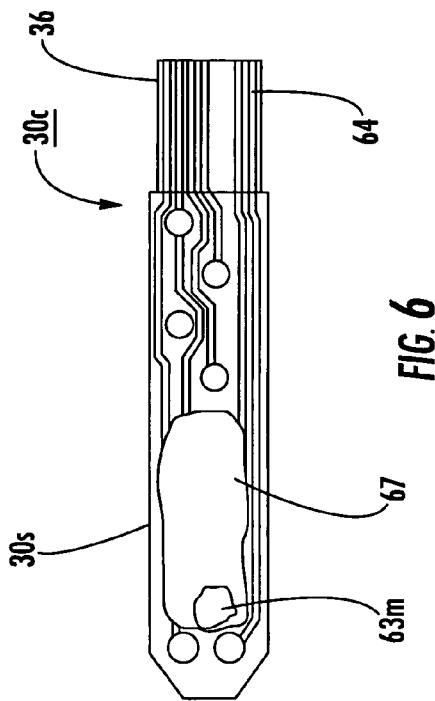
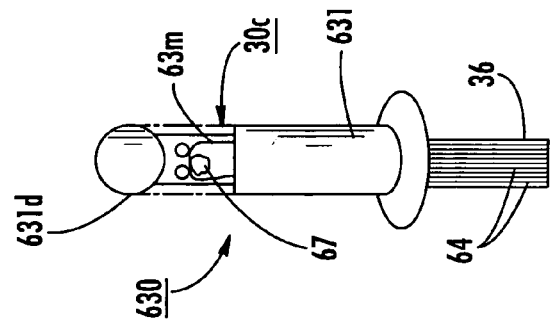
FIG. 5A
FIG. 6
FIG. 5B

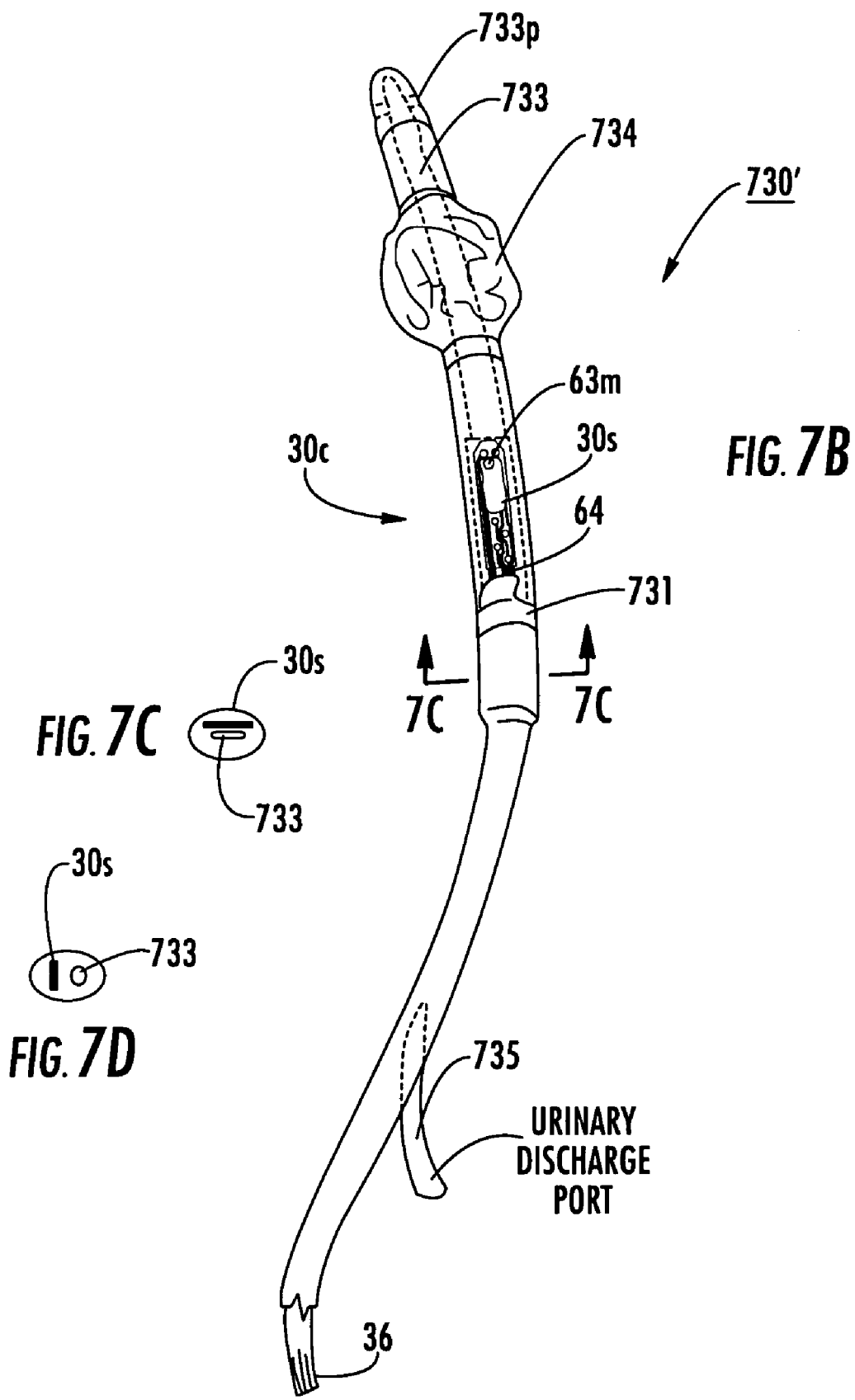

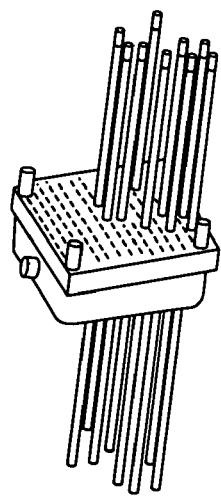
FIG. 13A
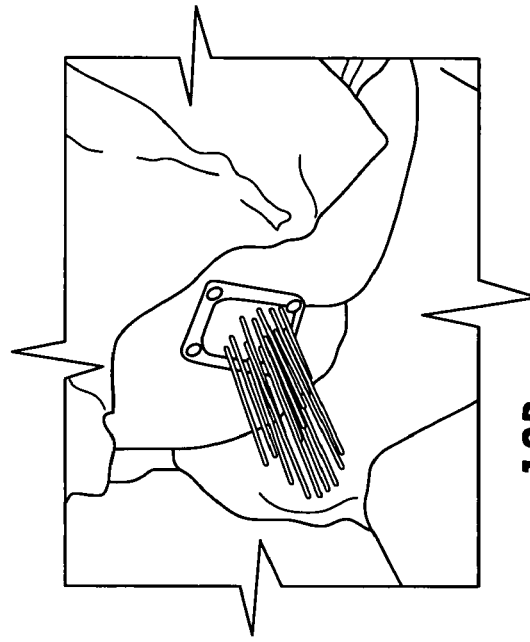
FIG. 13B
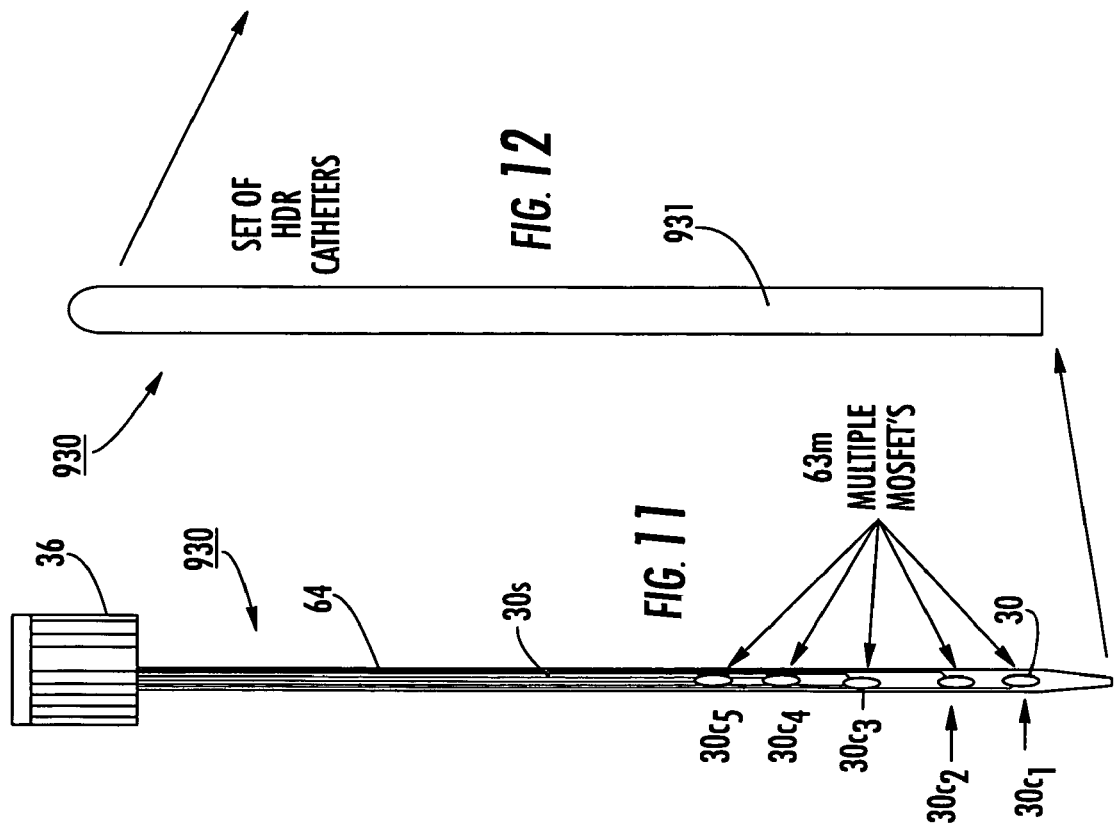
FIG. 12
FIG. 11

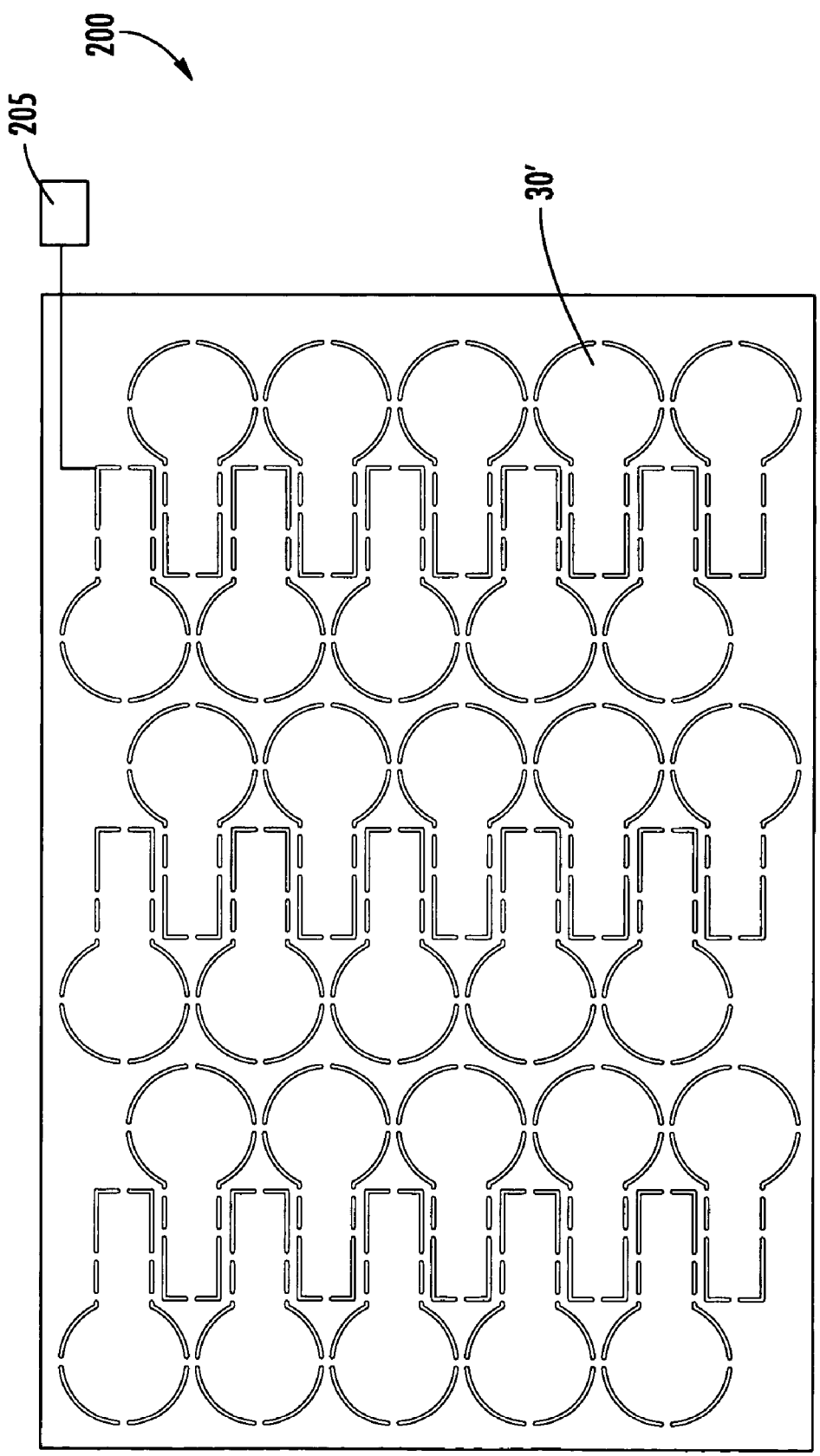

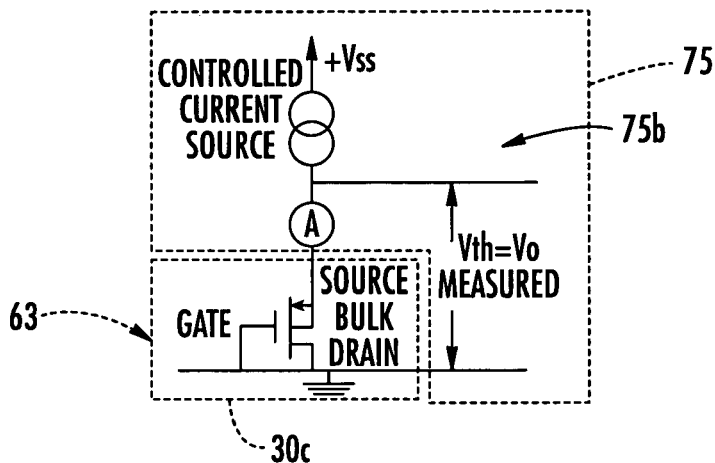
*FIG. 22A*
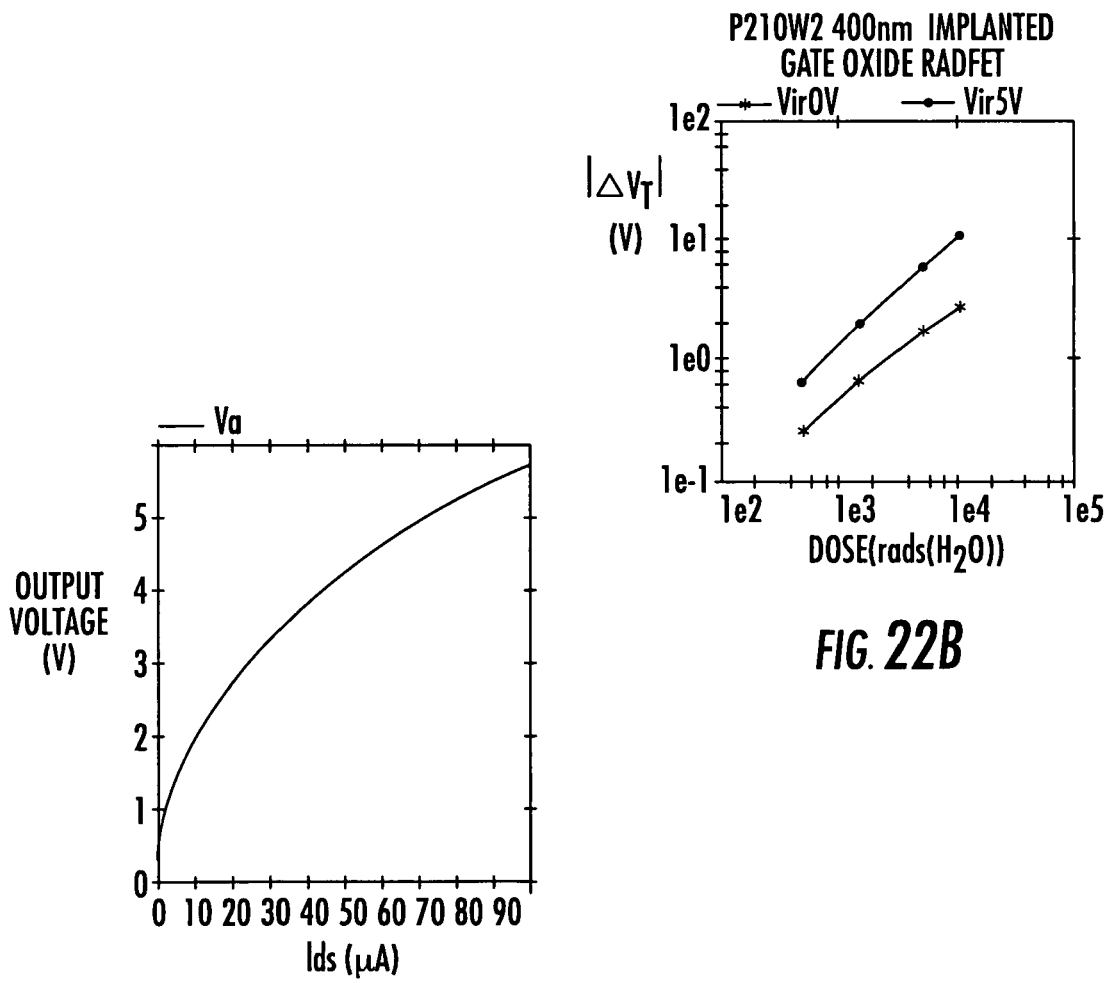
*FIG. 22B*
*FIG. 23*

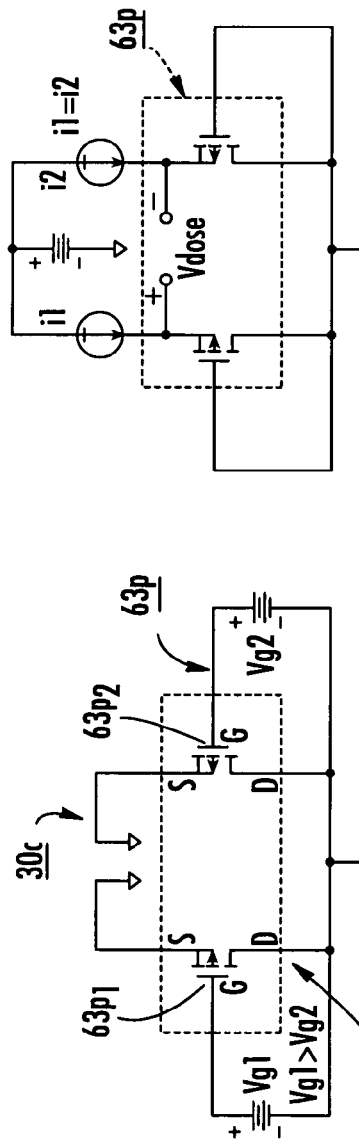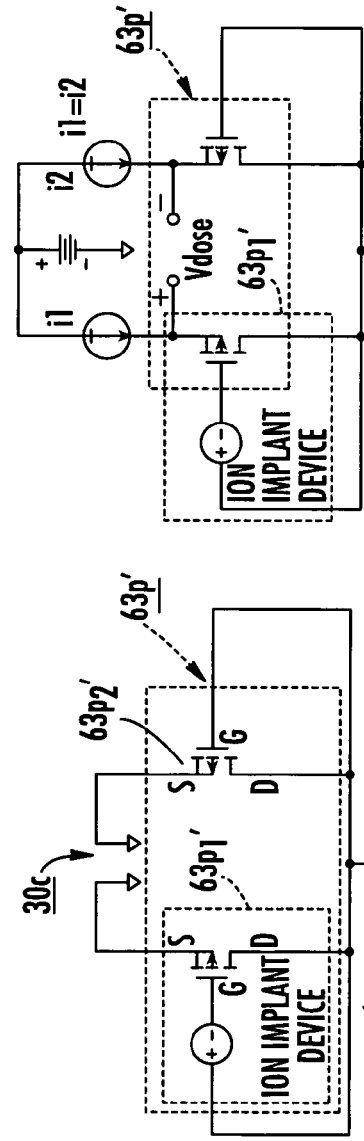
FIG. 24A
FIG. 24B

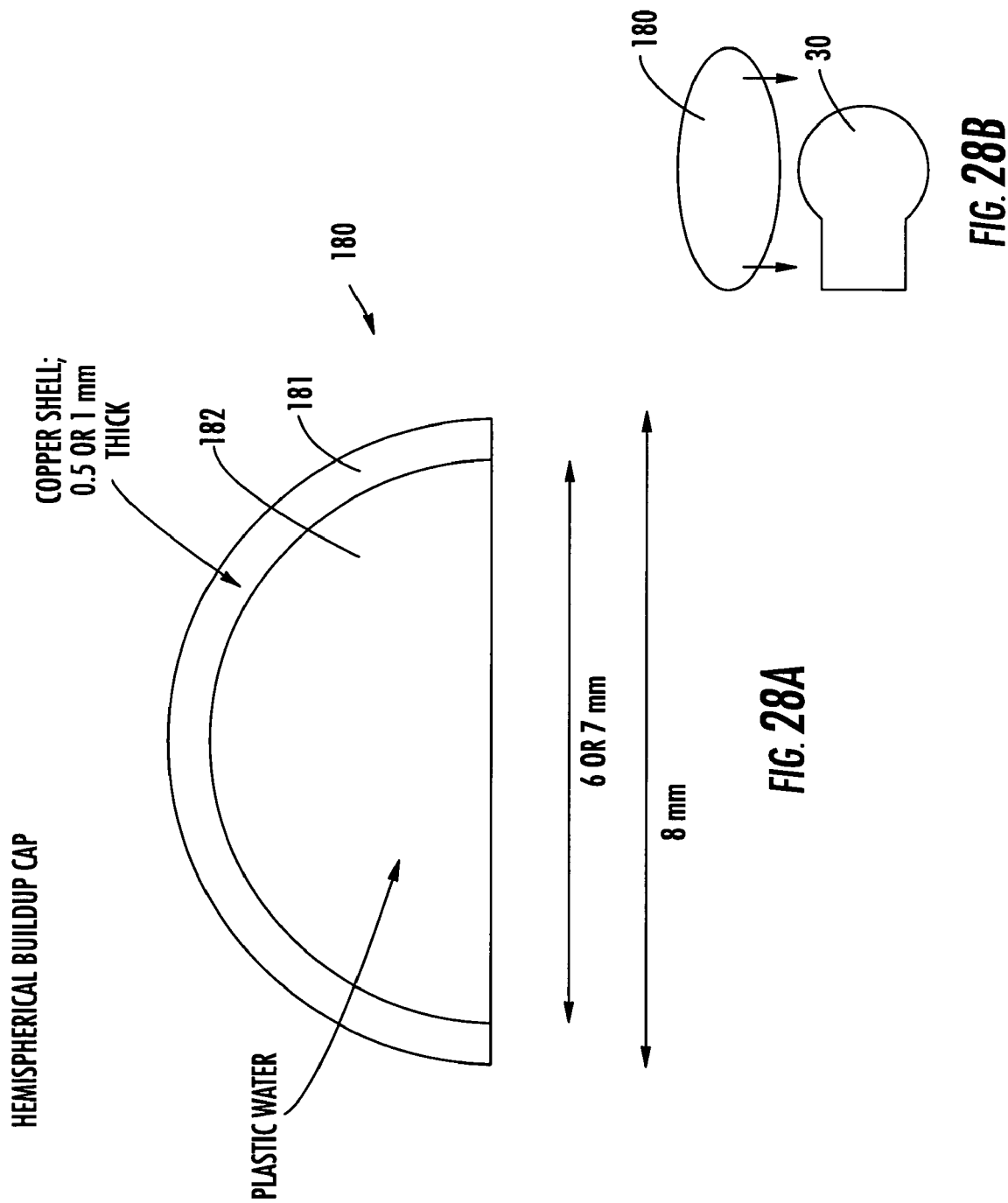

| PARAMETER | MIN | MAX | UNITS |
|---|---|---|---|
| ZTC BIAS CURRENT (DRAIN + GATE SHORTED) NOTE: THIS MAY BE ACHIEVED THROUGH THE ADDITION OF THE SERIES DIODE ELEMENT. | 2 | 50 | $\mu A$ |
| TEMPCO VS. ZTC BIAS CURRENT SLOPE (MEASURED +/-1$\mu A$ AROUND THE ZTC CURRENT) | 0 | 100 | $(\mu V/°C)/\mu A$ |
| ZTC BIAS CURRENT DRIFT WITH DOSE (100cGy DOSE) | 0 | 0.5 | $\mu A/cGy$ |
| TEMPERATURE COEFFICIENT AT 10$\mu A$ BIAS CURRENT (RADFET ONLY) | -2 | 2 | mV/°C |
| INITIAL THRESHOLD VOLTAGE (RADFET) (MEASURED AT ZTC CURRENT- ONE DOSE) | 0.25 | 6.0 | V |
| INITIAL THRESHOLD VOLTAGE (RADFET) (MEASURED AT 10$\mu A$ - DVS) | 0.25 | 0.65 | V |
| TRANSCONDUCTANCE (MEASURED AT ZTC CURRENT) | 10 | 100 | $\mu$Mho |
| SENSITIVITY (INITIAL 100 cGy DOSE) | 0.35 | 2 | mV/cGY |
| FADE (INITIAL 100cGy DOSE - MEASURE CHANGE IN SHIFT FROM 5 MINUTE TO 15 MINUTE READINGS) | -2.5 | 2.5 | % OF VOLTAGE SHIFT |
| DIODE FORWARD VOLTAGE (MEASURED AT ZTC CURRENT - ONEDOSE ONLY) | 0.4 | 0.7 | V |

TABLE 1

FIG. 29

| FACTOR | VALUE |
|---|---|
| ENERGY = 8 MeV, ELECTRON | 1.055 |
| DOSE RATE = 300cGy / MIN | 1.000 |
| FIELD SIZE = 10 cm * 10 cm | 1.000 |
| TEMPERATURE = 33C | 1.000 |
| WEDGE ANGLE = 30 DEGREES | 0.990 |
| FADE TIME = 22 MINUTES | 1.021 |

TABLE 2

| COEFFICIENT | LOCATION |
|---|---|
| a - TEMPERATURE | 370-373h |
| b - TEMPERATURE | 374-377h |
| c - TEMPERATURE | 378-37Bh |
| d - TEMPERATURE | 37C-37Fh |

| COEFFICIENT | LOCATION |
|---|---|
| a - FADE | 380-383h |
| b - FADE | 384-387h |
| c - FADE | 388-38Bh |
| d - FADE | 38C-38Fh |

TABLE 4

| DESIRED CURRENT (μA) | IDEAL DAC SETTING REQUIRED (DEC) | ACTUAL DAC SETTING REQUIRED (DEC) |
|---|---|---|
| 2 | 32448 | 32317 |
| 5 | 31968 | 31837 |
| 10 | 31168 | 31039 |
| 20 | 29568 | 29439 |
| 30 | 27968 | 27841 |
| 40 | 26368 | 26242 |
| 50 | 24768 | 24644 |
| 100 | 16768 | 16651 |
| 150 | 8768 | 8659 |
| 200 | 768 | 666 |

| FIELD | DESCRIPTION (PATCH AND/OR INTERNAL DOSIMETER MEMORY LOCATION) |
|---|---|
| READING NUMBER | READING RECORD NUMBER |
| SERIAL NUMBER (KEY) | THE SENSOR'S SERIAL NUMBER (10-DIGIT BCD, FORMAT AABBCCDD-EE) |
| CALCULATED DOSE | THE CALCULATED DOSE IN cGy (IEEE-754) |
| ZEROING A/D VALUE | THE 24-BIT A/D CONVERSION VALUE FROM THE ZEROING OPERATION |
| READING A/D VALUE | THE 24-BIT A/D CONVERSION VALUE FROM THE READING OPERATION |
| PATIENT ID | THE PATIENT'S ID# (14-DIGIT BCD) |
| THERAPY MACHINE | THE THERAPY MACHINE'S ID# (2-DIGIT BCD) |
| FIELD NUMBER | THE FIELD # (2-DIGIT BCD) |
| SENSOR LOCATION | A NUMERIC DESCRIBING THE SENSOR PLACEMENT (2-DIGIT BCD)AND/OR TYPE |
| PLANNED DOSE | THE PLANNED DOSE IN cGy (4-DIGIT BCD, FORMAT AAB.B) |
| THERAPIST NUMBER | THE THERAPIST'S ID# (4-DIGIT BCD) |
| ZERO TIME STAMP | THE ZERO READING TIME STAMP FOR THE SENSOR |
| DOSE TIME STAMP | THE DOSE READING TIME STAMP FOR THE SENSOR |
| % PLAN | THE PERCENTAGE OF THE PLANNED DOSE ACTUALLY DETECTED (IEEE-754) |
| CALC_CONFIG | THE CALCULATION CONFIGURATION REGISTER USED DURING DOSE CALCULATION |
| FIELD SIZE | THE FIELD SIZE (4-DIGIT BCD, FORMAT AA X BB $cm^2$) |
| DOSE RATE | THE DOSE RATE IN MU/MIN |
| ENERGY TYPE | TREATMENT ENERGY TYPE: 0 = NOT SPECIFIED, 1= PHOTON, 2 = ELECTRON |
| ENERGY | TREATMENT ENERGY IN MB OR MeV USED |
| MONITOR UNITS | THE # OF MONITOR UNITS (MU) APPLIED |
| SSD | THE SOURCE-TO-SURFACE DISTANCE |
| BOLUS THICKNESS | THE THICKNESS OF BOLUS IN mm (2-DIGIT BCD) |
| WEDGE ANGLE | THE WEDGE ANGLE (IN DEGREES) (2-DIGIT BCD) |
| CHECKSUM | 16-BIT CRC CHECKSUM FOR THE DOSE RECORD (62-BYTES) |

TABLE 6

FIG. 40

TABLE 7
Functional Specifications of a Test Strip
- The test strip may be constructed as a dosimeter with the RADFET replaced with a series combination of a 1.2V shunt reference (specified at 0.1% tolerance and a 10K resistor (0.1% tolerance). The Gate/Drain connection may have a 39K, 0.1% tolerance resistor connected to circuit ground on the test strip.
- The test strip memory map may contain all of the defaults from the base load (at the ZTC process).

FIG. 41

TABLE 8
Exemplary Functional Specifications of a Reader

- The Reader bias current may be configured to have an accuracy of within about +/-50nA.
- The Reader may reproduce the bias current between the "pre" and "post" readings to within about 1nA.
- The reader battery may be about a 9V user-replaceable type; other battery types may be used.
- A 5 Volt regulator may power the reader pcb (Vcc).
- The initial tolerance of the Vcc supply may be specified at about 3% or better.
- The battery may constantly supply a low-power (such as about 3.3V) regulator (which may be independent of the power switch state) to serve as a backup supply for the real-time clock.
- The back-up supply may have sufficient storage capacitance to allow for changing the battery without the loss of the real-time clock settings (typically at least 2 minutes).
- The main voltage reference may be specified as about a 4.096V, with about a 0.1% initial accuracy device with a specified temperature coefficient of about 10ppm/C or better.
- The battery voltage (after reverse polarity protection and the switching circuitry) may be sensed by the A/D converter on the Display Controller in order to monitor the battery voltage.
- The Reader Software may periodically sample the battery voltage and provide a "Low Battery" warning.
- The Reader Software may disable dose readings and may display a "Replace Battery" message on the display based on the sensed battery voltage.
- The reader may have an on-board substantially real-time clock capable of keeping track of time and date.
- The reader software may have functions to set and retrieve the current time and date.
- The time and date may be displayed on the LCD display and may be recorded as part of the electronic Dose record for each individual patch.
- The clock may maintain date and time settings long enough for the user to replace the battery (typically at least 2 minutes).
- The Reader may have on-board memory capable of storing reader-specific calibration coefficients, serial number, and user entered information (ex. Hospital ID).
- There may be a bank of memory capable of storing multiple dose records for display or for download through the USB port.
- Each Dose Record within the reader memory may contain multiple fields. Each record may have a size limit, such as about 64 bytes in length.
- The reader memory may be large enough to hold at least about 100-250 dose records.
- The display may be a 2-line, 16-character LCD module.
- This digital to analog controller, referenced as the IBIAS DAC, may work in conjunction with op-amp circuitry to provide about ±2 – ±50μA of programmable bias current with at least about 20nA of resolution under processor control.
- The A/D converter may have a resolution of better than about 100μV and a range of at least about 2 Volts.
- There may be a USB interface provided for downloading records from the Reader memory to a remote pc and/or computer.

FIG. 42A

TABLE 8
- The Reader may be designed to remain in calibration for at least about 6 months (typically about 1 year). The user may have the option to test the reader calibration using an external test strip.
- The reader may interrogate the test strip memory and request that the user perform a "zeroing operation". The test strip may be zeroed and the resulting DACB value may be compared to the DACB value determined at the factory and may indicate a "Reader OK" if the DACB value is within the limits provided or a "Reader needs Cal" message if the DACB value is outside the limits. The limits may be determined on a per-Reader basis in factory calibration. The test strip may be configured so as not to be modified by the reader.
- The reader may indicate "Reader OK" when the test strip is inserted and the (4.096V) reference is within a target range (typically 4.075 - 4.116V for the 4.096 V reference) and display "Reader needs Cal" if outside of these limits. The tolerance on the limits may be about +/- 0.005V.

FIG. 42B

TABLE 9
Exemplary Functional Specification of a Patch and/or internal dosimeter

- The flex circuit may be designed for ease of manufacturability and for substantial conformance to the contours of the body.
- The flex circuit may be smaller than about 4cm long by about 1cm wide, and/or have about a 0.5mm narrow dimension.
- There may be test points on the top-side of the patch to simplify the test fixturing for the patch.
- The flex circuits may be configured in an array of about 16*2.
- The 32 RADFET devices may fit within a window of about 0.75" by 4."
- There may be an area reserved on the flex circuit panel for an adhesive barcode to uniquely identify the panel.
- The flex circuit may be compatible with multiple insertions (such as at least about 10-20) into an appropriate connector.
- The RADFET may be a p-type enhancement-mode device.
- The SENSOR may be constrained so that at the Zero-Temperature Coefficient (ZTC) current, the threshold voltage, measured upon receipt, is less than about 6 Volts and greater than about 0.25V.
- The initial voltage shift of the SENSOR may be at least about 35mV for a 100cGy dose.
- The maximum initial threshold voltage shift for the SENSOR is about 200mV for a 100cGy dose.
- The system may be designed for a maximum difference in temperature between the "pre" and "post" readings of about ±5°C.
- The ZTC current for each individual SENSOR may be determined during factory processing and be configured to operate within a drift tolerance.
- The SENSOR may have a trans-conductance between about $1/10K\Omega$ and $1/100K\Omega$ ($100\mu Mho$ and $10\mu Mho$ respectively) when measured at the ZTC current.
- The SENSOR may not fade more than 2.5% when a 100cGy dose is applied and the measurements taken at one or more of 5 minutes and 15 minutes after dose application.
- The Patch and/or internal dosimeter may have an on-board memory to store biasing, calibration and the dose record information.
- The device memory may comprise a serial EEPROM with a clock and data interface.
- The device may be rated to operate from about 3.3V − 10% to 5V +10%.
- The device may accommodate at least 2k bits of storage.
- The patch and/or internal dosimeter may be characterized for energy dependence and correction factors applied as necessary.
- There may be an adhesive (with peel away strip) on the bottom of the patch that allows direct placement on the patient.
- The SENSOR may have a ZTC current in the range of about 2μA to 50μA.
- A single patch and/or internal dosimeter may be provided to cover the 4-25MV, 4-25Mev energy range without correction factors.

*FIG. 43*

SINGLE-USE INTERNAL DOSIMETERS FOR DETECTING RADIATION IN FLUOROSCOPY AND OTHER MEDICAL PROCEDURES/THERAPIES

RELATED APPLICATIONS

This application is a continuation-in-part of U.S. patent application Ser. No. 10/303,591, filed Nov. 25, 2002, which claims priority from United States Provisional Patent Application Ser. No. 60/334,580, entitled Disposable Single-Use External Dosimeters for Use in Radiation Therapies, filed Nov. 30, 2001, the contents of each of which are hereby incorporated herein by reference.

FIELD OF THE INVENTION

The present invention generally relates to the assessment and/or quantitative evaluation of the amount of radiation exposure a patient undergoing therapy receives.

BACKGROUND OF THE INVENTION

Conventionally, radiation therapies are carried out over one or a successive series of treatment sessions. For certain radiation therapies, high-energy photons and/or electrons are carefully directed and/or focused from an ex vivo radiation source so that they travel into a targeted treatment area in a patient's body. In other radiation therapies, the radiation is delivered internally via planted radioactive seeds, radioactive analytes, and the like.

Generally stated, the size, shape, and position of the treatment area (typically where a tumor is or was) as well as its anatomical location in the body and its proximity to sensitive normal tissues are considered when generating a particular patient's treatment plan. That is, the treatment is planned so as to deliver a suitably high dose of radiation to the tumor or targeted tissue while minimizing the dose to nearby sensitive tissue that typically cannot be completely avoided. Directing radiation into non-affected regions may produce undesired side effects, particularly as it relates to tissue that may be sensitive to certain dosages of radiation. Unfortunately, even when the patient plan is carefully constructed to account for the location of the cancerous tissue and the sensitive non-affected regions, even small errors in set-up due to beam angle or patient position during delivery of the radiation therapy can inadvertently misdirect radiation into those regions or can influence the dose amount that is actually received by the targeted tissue. Further, the demand for radiation treatment equipment is typically relatively high and this demand may limit the set-up time allowed or allocated in the treatment room between patients.

In the past, implantable devices for oncology applications have been proposed to evaluate the radiation dose amount received in vivo at the tumor site. See, e.g., U.S. Pat. No. 6,402,689 to Scarantino et al., the contents of which are hereby incorporated by reference herein. Measuring the radiation at the tumor site in vivo can provide improved estimates of doses received. However, for certain tumor types or situations, alternatively configured internal radiation dosimeters may be desirable and sufficient for clinical purposes.

In view of the foregoing, there remains a need for improved economical and easy to use internal radiation dosimeters.

SUMMARY OF EMBODIMENTS OF THE INVENTION

Certain embodiments are directed to cost-effective internal radiation dosimeters that can be used to evaluate radiation dose exposure delivered to a patient in a single treatment session.

Some embodiments of the present invention provide a memory storage device on a radiation dosimeter probe that can be used to record the dose history of the dosimeter probe. The dosimeter probe can be a single-use (used to obtain radiation data during a single treatment session) disposable, elongate internal probe that includes a memory storage device may be queried by a reader in order to obtain a record of the dose. Other information, such as patient identification, time, date, hospital, therapist, state of the device, dosed/undosed and calibration data may be stored in the memory storage device.

The internal probes can be used to provide an economic method of determining the amount of radiation delivered to a patient undergoing a medical treatment, such as an oncology patient in situ.

Embodiments of the present invention are directed to a disposable, single-use internal radiation dosimeter that and operates in a relatively easy to operate and read manner without requiring the use of lead wires (or even power) during irradiation.

The internal dosimeter may include at least one radiation sensor, each comprising a single MOSFET. The dosimeter can be positioned in the patient so as to place at least one of the radiation sensors in a location that is generally proximate to the target treatment site.

In some embodiments, the dosimeter radiation sensor may be pre-dosed and/or calibrated before the dosimeter probe is inserted into the patient. Certain data obtained may be stored in an electronic storage device provided on/in the dosimeter itself. The storage device may be, for example, an EEPROM. Other information, such as the patient's name, the doctor's name, the test or treatment date and the like, may also be stored in the storage device provided in/on the dosimeter probe. Alternatively, the data can be stored on a computer readable memory integrated on a physical record sheet that can be placed in the patient's file.

Some embodiments are directed to methods for monitoring radiation exposure for a patient undergoing a medical procedure. The methods include: (a) inserting a single-use dosimeter into a patient; (b) exposing the patient to radiation in a medical procedure during a treatment session, wherein the at least one dosimeter comprises at least one radiation sensor circuit with a MOSFET and electronic memory that holds calibration data for the MOSFET; (c) transmitting data from the dosimeter to a dose-reader device after the exposing step to obtain the calibration data and data associated with a change in an operational parameter in the MOSFET of the dosimeter radiation sensor circuit; (d) removing the dosimeter from the patient proximate in time to and end of the treatment session; and (d) determining radiation received by the patient during the exposing step based on the change in the operational parameter of the MOSFET and the calibration data.

The internal dosimeter probe body can be configured to reside within a natural lumen or cavity, such as a mouthpiece and/or bite block, an ear plug, a nasal plug, a rectal plug, a male genourinary catheter, a female geno-urinary plug or catheter, and the like. In other embodiments, the dosimeter probe can be configured as a transcutaneous device.

Other embodiments are directed to systems for monitoring radiation administered to a patient during a diagnostic and/or therapeutic treatment. The systems include: (a) at least one single-use internal dosimeter, the internal dosimeter comprising at least one radiation sensor circuit comprising a MOSFET having an associated threshold voltage that changes when exposed to radiation and electronic memory comprising calibration data for determining radiation dose; and (b) a portable dose-reader configured to obtain voltage threshold data and calibration data from the at least one internal dosimeter corresponding to a dose amount of radiation exposure received during irradiation exposure.

The dosimeter can be configured with a body holding the at least one radiation sensor circuit having a MOSFET (typically a single unbiased MOSFET) and the electronic memory can include stored calibration coefficient for the respective MOSFET in the radiation sensor circuit for determining radiation dose. During irradiation, the dosimeter radiation circuit can be quiescent and unpowered with a perimeter that is devoid of outwardly extending loose lead wires. The radiation circuit and memory may be disposed on a substrate that is removeable from the probe body and may be retained in a patient data record/file allowing the probe body to be discarded.

In some embodiments, the system can also include at least one an external skin mounted patch dosimeter. The patch can include at least one radiation sensor circuit, each having a respective one MOSFET. Each MOSFET in respective radiation sensor circuits can be configured to independently detect radiation, and each of the radiation sensor circuits may share certain operative components, such as memory, or may operate independently.

Still other embodiments are directed to internal single-use radiation dosimeters. The dosimeters include: (a) at least one radiation sensor circuit with a MOSFET having an associated threshold voltage that changes when exposed to radiation to provide quantifiable radiation exposure data, wherein the radiation sensor circuit is unpowered during irradiation; (b) electronic memory having radiation calibration data for the MOSFET; and (c) a reader contact zone on the dosimeter configured to allow a portable reader to electrically engage the dosimeter to obtain the radiation exposure and calibration data. The radiation dosimeter is a single-use dosimeter configured for use during a single medical treatment session.

The calibration data can include a zero temperature coefficient and the electronic memory may include electronic instructions for automatically directing a remote reader on how to communicate with the dosimeter.

Other embodiments are directed to portable medical radiation dose readers. The readers include: a portable housing and a circuit held in the portable housing. The circuit is configured to communicate with an electronic memory of at least one single use internal dosimeter to obtain voltage threshold data corresponding to a dose amount of radiation exposure that the at least one dosimeter is exposed to during irradiation and to prompt a user to input predetermined data associated with dose evaluation, patient data and/or clinic data.

In some embodiments, the reader is also configured to communicate with an electronic memory of at least one single use external skin mount radiation dosimeter patch to obtain voltage threshold data corresponding to a dose amount of radiation exposure that the at least one patch is exposed to during irradiation and to prompt a user to input predetermined data associated with dose evaluation, patient data and/or clinic data.

The reader can include computer program code for identifying what type of dosimeter is undergoing evaluation, and computer program code that provides a selectable list of differently configured dosimeters, including an external skin mount patch and a plurality of different internal dosimeters, all configured to be evaluated by the same dose reader.

Another embodiment is directed to a computer program product for evaluating a radiation dose delivered to a patient. The computer program product comprises a computer readable storage medium having computer readable program code embodied in the medium. The computer-readable program code comprises: (a) computer readable program code for receiving pre-irradiation threshold voltage data associated with an internal dosimeter having at least one (but can have a plurality of spaced apart) radiation sensor circuit(s) (b) computer readable program code for directing a reader to communicate with the dosimeter to obtain radiation data from the at least one (or plurality of different) radiation sensor circuit (s); and (c) computer readable program code for determining the voltage threshold shift of the at least one radiation sensor circuit(s) after radiation to determine the radiation exposure.

In still further embodiments of the present invention, a dose-reader may be adapted to communicate with the dosimeter via a sensor port. The dose-reader can be a pocket or palm sized portable device. The dose-reader may also include a communications port, for example, a universal serial port (USB), RS 232 and the like, for downloading obtained data to a computer application or remote computer. The dose-reader functionality may be incorporated into a personal digital assistant (PDA) or other pervasive computer device.

In particular embodiments, the dose-reader may be a multi-purpose reader configured to communicate with surface mount sensor patches as well as the internal dosimeter configurations contemplated by embodiments of the present invention. In some embodiments, both a surface mount dosimeter patch and an internal dosimeter can be used and read by the same reader.

In further embodiments the dosimeter may be configured to communicate with the dose-reader wirelessly. For example, the sensor patch and the dose-reader may both be equipped with a radio frequency (RF) interface so that information may be shared between the two devices.

The foregoing and other objects and aspects of the present invention are explained in detail in the specification set forth below.

BRIEF DESCRIPTION OF THE FIGURES

FIG. 2B is a top schematic view of another embodiment of an oral cavity dosimeter according to the present invention.

FIG. 3A is a side schematic view of an oral cavity dosimeter being placed in position according to embodiments of the present invention.

FIGS. 3B and 3C are side schematic views of the oral cavity dosimeter shown in FIG. 3A, each having different extension tab lengths according to embodiments of the present invention.

FIG. 5A is a schematic view of an internal nasal and/or ear plug dosimeter according to embodiments of the present invention.

FIG. 5B is a partial cutaway view of a nasal and/or ear plug dosimeter similar to that shown in FIG. 5A.

FIG. 6 is a top view of a radiation sensor circuit on a flex circuit substrate that can be held in the body of the plugs shown in FIGS. 5A and 5B according to embodiments of the present invention.

FIG. 7B is a perspective view of a catheter with an anchoring balloon configured to hold the dosimeter therein according to other embodiments of the present invention.

FIGS. 7C and 7D are section views of different embodiments of the catheter shown in FIG. 7B, the view taken along lines 7C-7C, illustrating a urine discharge channel and a dosimeter substrate held in the catheter according to embodiments of the present invention.

FIG. 11 is a top view of a dosimeter having a flex circuit substrate holding a plurality of axially spaced apart MOSFETs configured to be received in a flexible catheter sheath shown in FIG. 12.

FIG. 12 is a side view of a catheter or sheath member configured to receive the elongate substrate shown in FIG. 11.

FIGS. 13A and 13B are digital photographs that illustrate a prior art set of HDR (high dose radiation) catheters held in a grid member (the photographs were obtained from Indianacancer.com). FIG. 13B illustrates the device in position on a patient undergoing brachytherapy. The elongate dosimeter shown in FIG. 11 can be configured to be directly inserted into one or more of the open catheters shown in FIG. 13A or 13B or may be covered in the sheath shown in FIG. 12 and then inserted therein, according to particular embodiments of the present invention.

FIG. 20B is a schematic illustration of a sheet of sensors according to further embodiments of the present invention.

FIG. 22A is a schematic of a threshold voltage reader circuit according to further embodiments of the present invention.

FIG. 22B is a graph of the change in the threshold voltage value versus radiation dose according to still further embodiments of the present invention.

FIG. 23 is a graph of the threshold voltage dependence on Ids using the voltage ($V_0$) of the reader illustrated in FIG. 22A.

FIG. 24A is a schematic of a circuit diagram with a MOSFET pair, the left side of the figure corresponding to an irradiation operative configuration and the right side of the figure corresponding to a read dose operative configuration, according to some embodiments of the present invention.

FIG. 24B is a schematic circuit diagram with a MOSFET pair, the left side of the figure corresponding to an irradiation operative configuration and the right side of the figure corresponding to a read dose operative configuration, according to further embodiments of the present invention.

FIGS. 28A and 28B are schematic diagrams illustrating buildup caps according to further embodiments of the present invention.

FIG. 29 is a table including sensor specifications according to further embodiments of the present invention.

FIG. 40 is a table including a list of items included in an exemplary dose record according to some embodiments of the present invention.

FIG. 41 is a table including functional specifications of test strips according to further embodiments of the present invention.

FIGS. 42A and 42B are a table including functional specifications of readers according to still further embodiments of the present invention.

FIG. 43 is a table including functional specifications of patches and/or internal dosimeters according to some embodiments of the present invention.

DESCRIPTION OF EMBODIMENTS OF THE INVENTION

Figure 1:
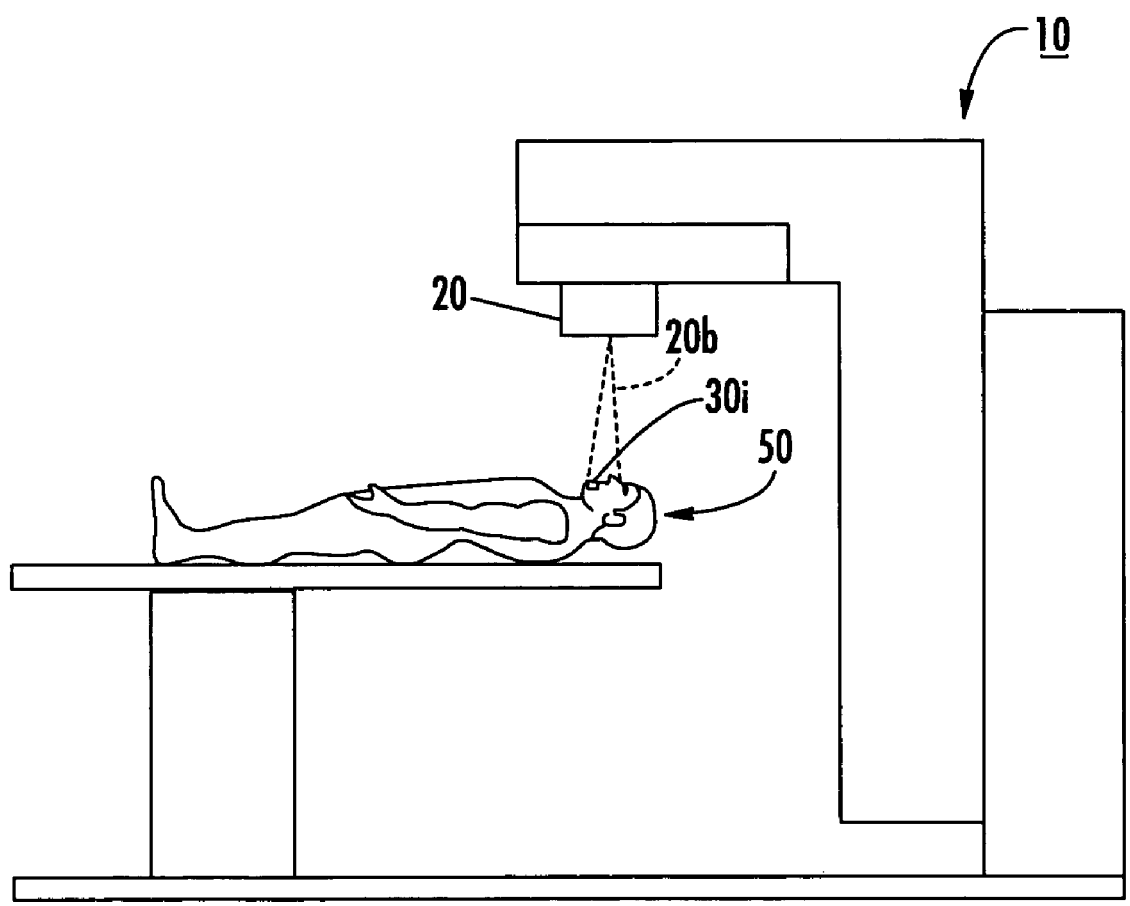
FIG. 1 is a schematic illustration of a patient undergoing radiation treatment according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components, features, or layers may be exaggerated for clarity. In the block diagrams or flow charts, broken lines indicate optional operations, or features unless stated otherwise. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense expressly so defined herein.

With reference to certain particular embodiments, the description of a radiation sensor circuit having a single operative MOSFET means that the circuit may include a semiconductor component that has more than one MOSFET thereon/therein, but only a single MOSFET is operatively required to obtain the radiation data for a single radiation circuit (biasing of two MOSFETS is not required). The term "probe" describes a body member that is sized and configured for internal positioning inside an object, typically an animal, and more typically a human subject. The term "probe" is meant to be broadly interpreted and includes, but is not limited to, catheters (slender, flexible tubes), stents, plugs, suppository and/or tampon-like bodies that hold at least one radiation sensor circuit thereon or therein. The probes can be sized and configured for intracavity or natural lumen placement. In some embodiments the probes are configured to be releaseably securable and/or in a generally fixed target location in the body, in a natural lumen or cavity during the irradiation. In other embodiments, the probes may be sized and configured for transcutaneuous and/or subcutaneous placement. Biocompatible materials and/or coatings can be used to allow for placement in an in vivo body. The term "genourinary" includes the gender-specific natural lumens and cavities, such as, for females, the vagina, the cervix, the uterus, the urethra, and the bladder, and for males, the urethra and the bladder (including the urethra proximate the prostate). However, in certain embodiments, the probes of the present invention may be alternately configured and adapted as appropriate for insertion in other natural lumens or body cavities such as, but not limited to, the rectum, the colon, the uterus, the cervix, the throat, the mouth, the ear, the nose, the esophagus or other fluid or respiratory passages, and the like.

The statements characterizing one or more of the priority applications as a "continuation-in-part" application of a prior application listed under the "Related Applications" section above is used to indicate that additional subject matter was added to the specification of the prior application but does not necessarily mean that the entire invention described and claimed in the present application is not supported in full by the prior application(s).

FIG. 1 illustrates an example of a radiation system 10 with a radiation beam source 20 directed at a patient 50 having a tumor site. The patient 50 can be positioned so as to be aligned and stationary with respect to the beam 20b (illustrated by the diverging dotted lines) during the treatment. As such, the patient 50 can be arranged in any desired position depending on the direction of the beam, the location of the tumor, and the type of radiation therapy system employed. As shown, the patient is reclined, substantially flat and face up on a table so that the beam 20b is directed into the targeted tumor site in the body as the patient undergoes radiation therapy in a treatment session. However, the patient may be sitting, generally vertically, or partially reclined during the treatment. Typically, the patient will undergo a plurality of successive treatment sessions over a treatment period. Each treatment session may be planned to administer radiation doses of between about 1-2 Gray (100-200 cGy) with an overall treatment limit of about 35-80 Gray. However, for certain higher dose therapies, such as those provided using HDR sources, daily doses may be between about 5-15 Gy. In any event, a different dosimeter will typically be used for each treatment monitored. In other embodiments, radiation is delivered during alternative medical procedures or treatment sessions, such as during fluoroscopy procedures. In some embodiments, single-use dosimeters 30i can work over a 20-1500 cGy operating range, while in other configurations, the single-use dosimeters 30i can be configured to operate over typical or high dose ranges, such as about 20-500 cGy, or 500-1500 cGy, providing flexibility for varying treatment plans. As used herein, "disposable" means that the sensor patch is not reused and can be disposed of or placed in the patient's records.

In some embodiments, the internal dosimeters 30i contemplated by the instant invention can be used in Quality Assurance evaluations of planned radiation therapies for dose verification. Thus, the internal dosimeters can be used during a dose planning session (such as for Quality Assurance in set-up, confirmation-to-plan analysis, and the like, whether in a phantom and/or an actual subject to compare the planned dose to the actual dose) and/or used during active radiation therapy sessions.

In the embodiment shown in FIG. 1, the patient is undergoing radiation treatment directed to the neck and/or head region. As such, an internal dosimeter 30i can be placed in one or more of the ear canal, the nasal cavity and/or the mouth cavity. In addition, an external skin mounted patch dosimeter 30 can also be used to monitor radiation dose. A similar radiation sensor circuit 30c can be used for both the internal dosimeter 30i and the external patch (where used) and/or for each of the internal dosimeters employed. For example, two internal dosimeters 30i can be used, a nasal plug dosimeter (FIG. 5A) and a mouthpiece dosimeter (FIG. 2A), and each can include at least one radiation sensor circuit 30c that includes a radiation sensitive device 63, typically a MOSFET, that changes in a predictable and detectable manner when exposed to irradiation, but does not require powering during irradiation. As will be discussed further below, an external dosimeter patch 30 can also be used. The patch 30 can also include a radiation sensor circuit 30c with a radiation sensitive device 63, also typically a MOSFET 63m, that changes in a predictable and detectable manner when exposed to irradiation, but does not require powering during irradiation. Each of the different internal dosimeters 30i and/or an internal dosimeter and the external patch 30 can be configured to be read by a common portable reader 75 (as illustratively shown, for example, in FIG. 17A).

Figure 30:
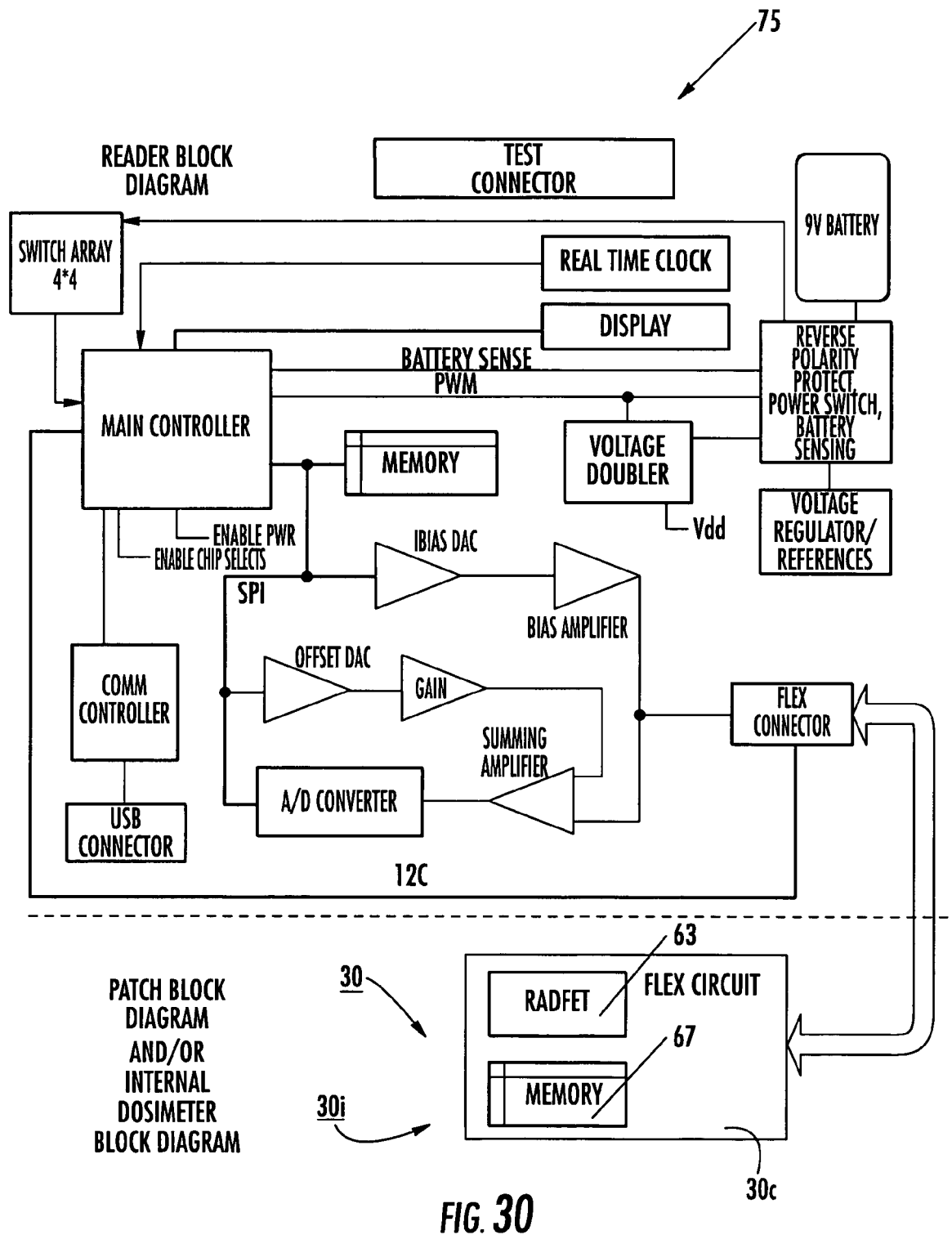
FIG. 30 is a block diagram illustrating functions of a reader device and a patch according to some embodiments of the present invention.

FIG. 30 illustrates that the radiation circuit 30c of each of the internal dosimeter 30i and the patch 30 can be generally the same, in that each has a MOSFET 63m (typically a single operative MOSFET for each radiation circuit 30c) and is in communication with a memory 67. In some embodiments where multiple radiation circuits 30c are held on a single patch 30 and/or in or on a single internal dosimeter 30i (see, e.g., FIG. 11), certain circuit components may be shared (such as the memory 67 and a common flex circuit substrate) or each circuit 30c may be independent and have a respective MOSFET 63 and memory 67. For more discussion of multi-sensor patches, see co-pending co-assigned U.S. patent application Ser. No. 10/865,430 filed Jun. 10, 2004, identified by, the contents of which are hereby incorporated by reference as if recited in full herein. Similarly, for additional discussion of external skin mounted patches, see co-pending co-assigned U.S. patent application Ser. No. 10/303,591, and U.S. patent application Ser. No. 10/865,615, filed Jun. 10, 2004, identified by, the contents of which are hereby incorporated by reference as if recited in full herein.

Figure 7A:
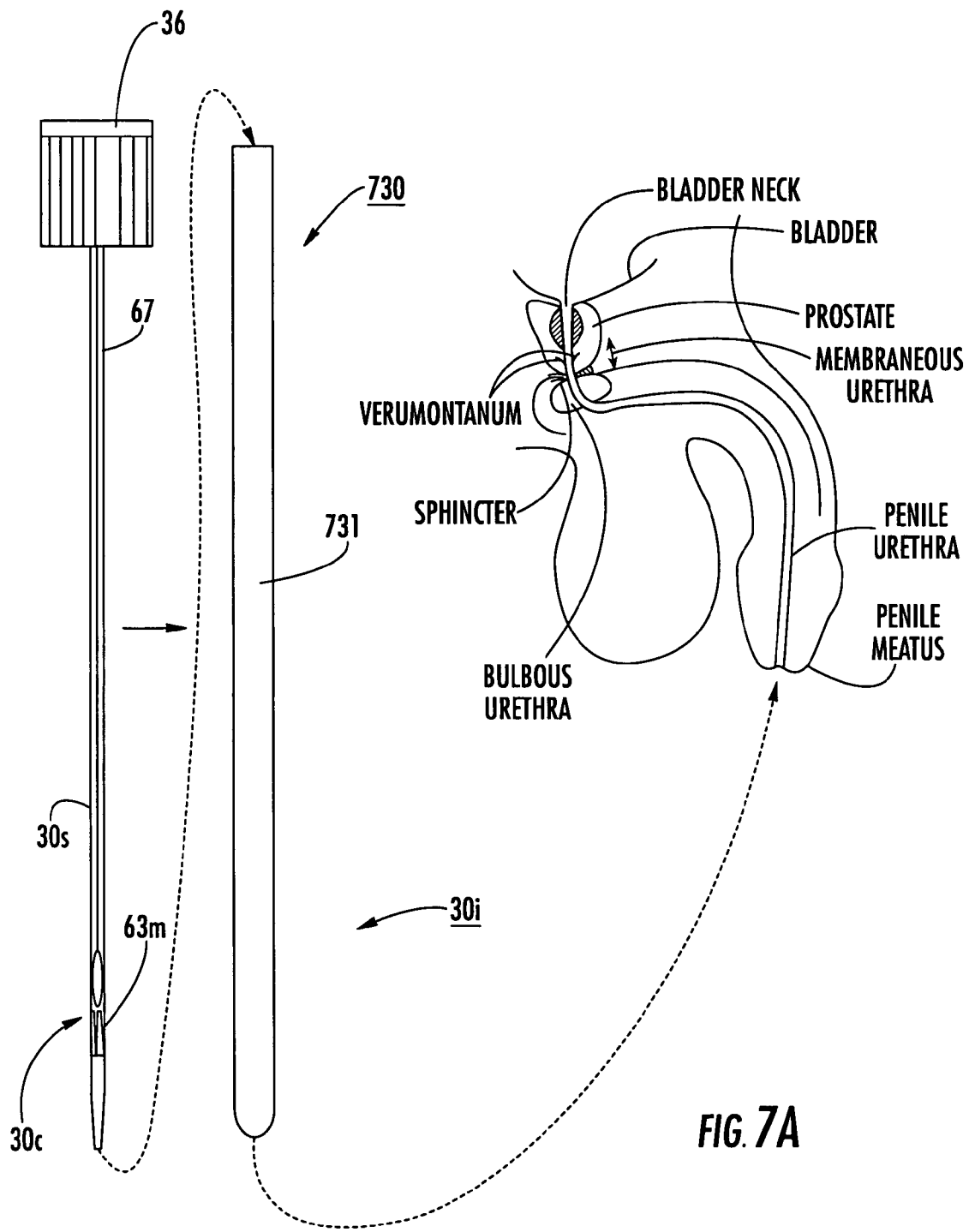
FIG. 7A is an exploded schematic illustration of an internal male urethra probe with a flexible sheath and a dosimeter configured to reside in the male urethra during irradiation according to some embodiments of the present invention.
Figures 8, 9:
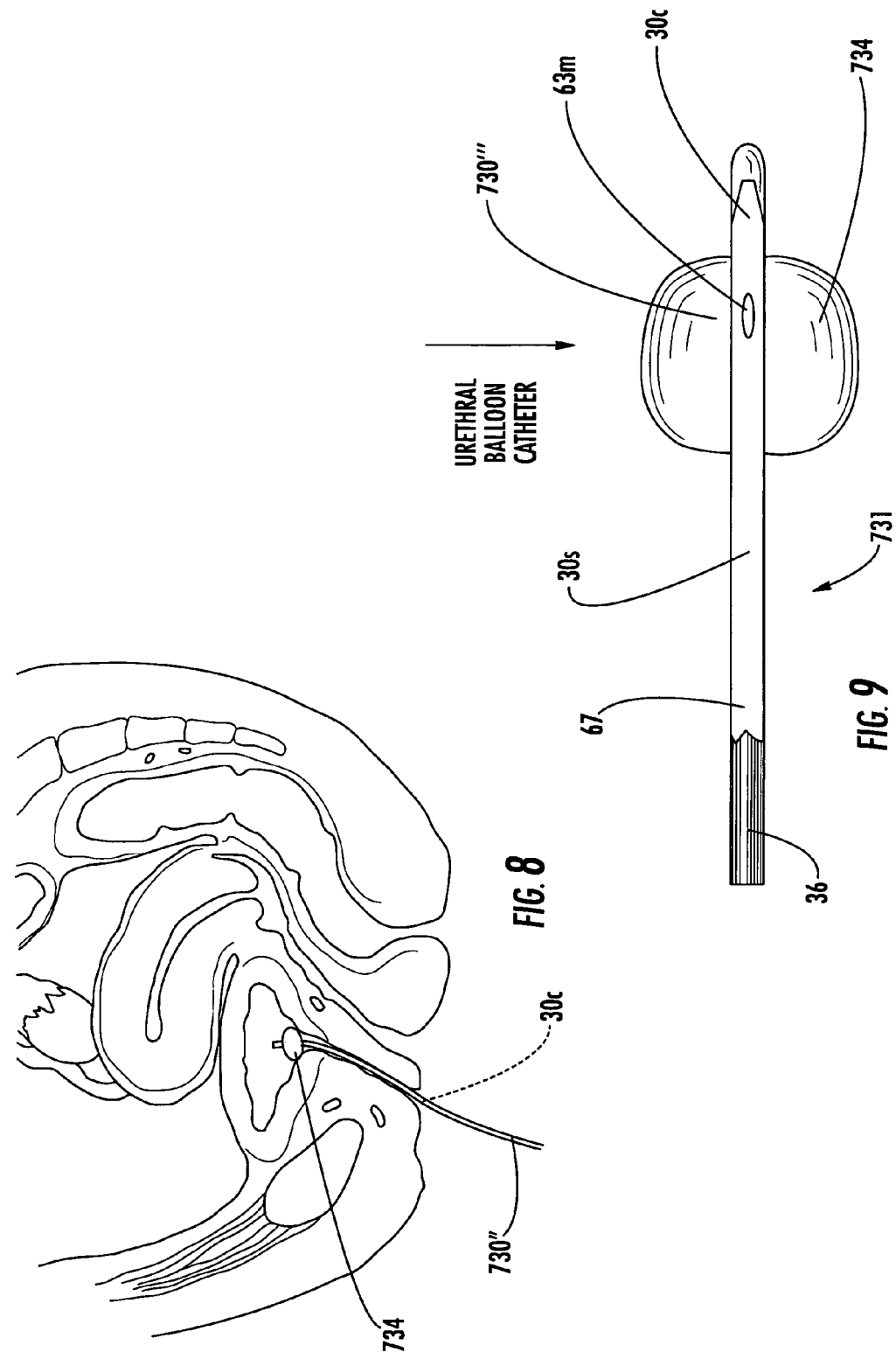
FIG. 8 is a schematic illustration of a female genourinary system with a balloon catheter held in the bladder thereof according to embodiments of the present invention.
FIG. 9 is a side view of a balloon catheter with the balloon inflated and the internal dosimeter radiation circuit held therein.

It is noted that the memory 67 may be located proximate the MOSFET 63m such as shown in FIG. 6. In other embodiments, the memory 67 (as well as other ancillary circuit components) may be positioned closer to a proximal end portion away from the MOSFET 63m, such as closer to the tab portion 36 (where used) to decrease the circuit size extending from a distal portion of the dosimeter 30i to the proximal portion (the latter of which, in position, may reside outside the body). For example, for genourinary catheters 30i, such as shown in FIGS. 7A, 7B and 9, the MOSFET 63m can be positioned at a distal end portion of the catheter while the memory can be disposed a distance away from the MOSFET 63m. With reference to FIGS. 6 and 30, where the radiation circuit 30c is held on a flex circuit substrate 30s, all or a portion of the flex circuit substrate may be configured to extend in a generally planar configuration in or on the internal dosimeter probe body. Alternatively, all or a portion of the flex substrate may be configured to have a curvilinear contour that can conform to an inner or outer wall of the probe body, or an interior space in the probe body (not shown).

To help monitor or estimate the amount of radiation that is delivered to the patient during a treatment session, at least one disposable single-use dosimeter 30, 30i can be used. As used herein, "single-use" is used to refer to a use for a single patient during a treatment session. The internal dosimeter 30i is typically used only once proximate in time and during a treatment. The internal dosimeter 30i may be removed after the treatment or sometime during the treatment, typically removed at the end of a single treatment session. It will be understood that a treatment session may include an active radiotherapy administration during a single treatment session or serially spaced apart treatment sessions. The treatment session may have a duration of minutes, hours, days and the like. The memory 67 or other electronic components may be configured to inhibit or prevent reuse. Furthermore, a calibration dose obtained before the external sensor 30 and/or internal dosimeter 30i is positioned on/in a patient is not to be considered the "single-use." The dosimeters 30i can be configured from biocompatible materials and sterilized prior to use. The dosimeters 30i can be packaged in sterilized packages for medical use. The dosimeters 30i can be packaged in a medical kit of at least one external mount skin patch 30 and at least one internal dosimeter 30i, and can, in certain embodiments, include two differently configured internal dosimeters (i.e., one for the mouth cavity and one for the ear cavity).

As discussed above, the internal dosimeter 30i is configured to change in an operational parameter in a predictable manner that correlates to the radiation dose it receives, as will be discussed further below. The internal dosimeter 30i can be configured so as to be self-contained and discrete and devoid of dangling lead wires extending to a remote power source or operating system during irradiation in position on the patient. As such, a reader, for example, reader 75 (FIGS. 16A and 30), can be configured to obtain the data from the radiation sensor circuit 30c by, for example, electrically contacting the dosimeter 30i of interest. An example of one embodiment of a suitable portable reader is shown in U.S. Design patent application Ser. No. 29/197,934, filed Jan. 20, 2004, the contents of which are hereby incorporated by reference as if recited/shown in full herein. The reader 75 can include computer program code for identifying what type of dosimeter 30i is undergoing evaluation, and may also include computer program code that provides a selectable list of differently configured dosimeters, including an external skin mount patch 30 and/or a plurality of different internal dosimeters 30i, all configured to be evaluated by the reader 75. In some embodiments, the reader 75 may include computer program code that prompts a user to identify the dosimeter configuration being evaluated.

As used herein, the reference number "75" will be used to refer generally to a reader device according to embodiments of the present invention. Particular embodiments of a reader device 75 may be referred to using the reference number 75 and followed by one or more apostrophes (or primes) attached thereto. For example, particular embodiments of the reader device may be denoted 75' or 75". This convention may similarly be used with respect to other features of the present invention. For example, the reference number "30'" will be used to refer to particular embodiments of an external skin mountable sensor patch and "30i" will be used to refer to embodiments of an internal dosimeter, herein. It will be understood that features discussed with respect to any embodiment of the present invention may be incorporated into other embodiments of the present invention even if these features are not discussed specifically with reference to each individual embodiment.

Figure 2A:
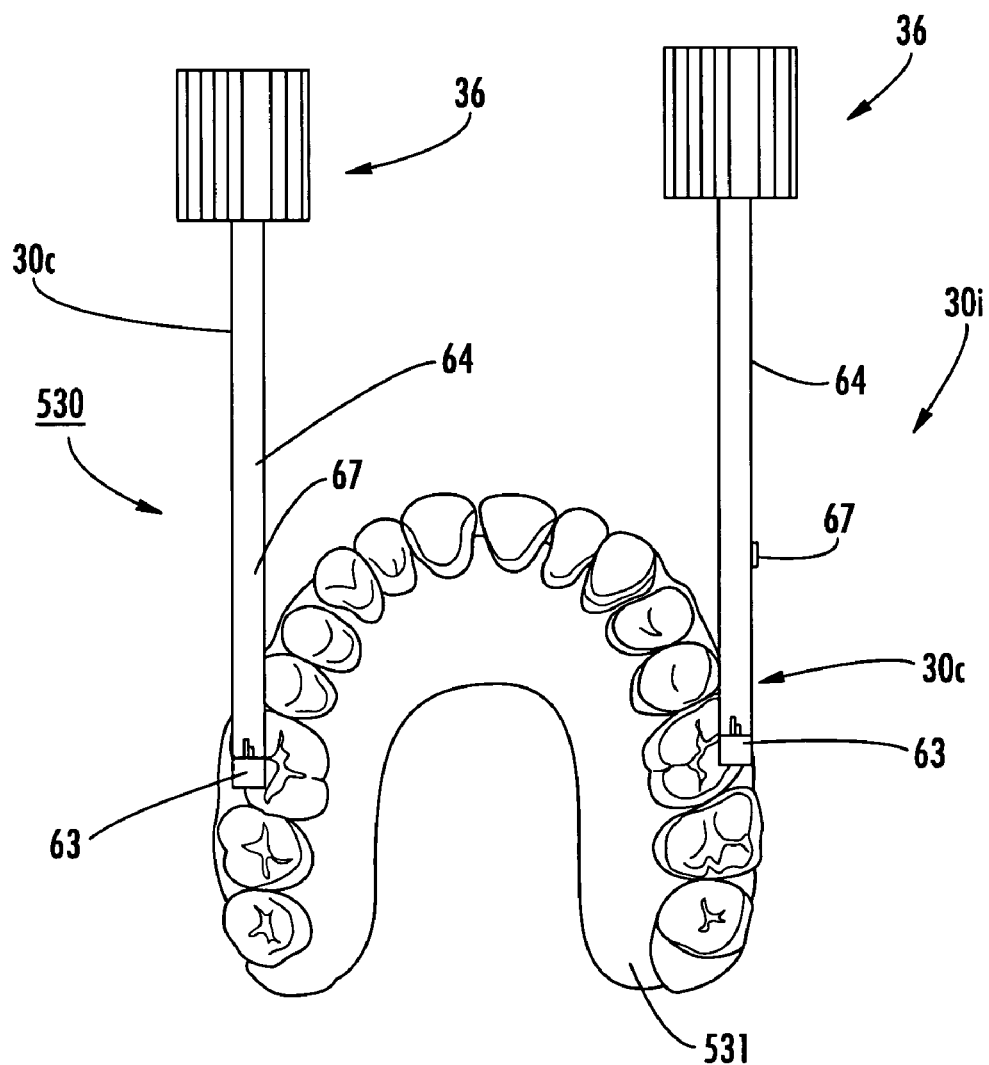
FIG. 2A is a top schematic view of an oral cavity dosimeter according to embodiments of the present invention.

FIG. 2A illustrates an internal dosimeter 30i that is configured to reside in the oral cavity of the mouth. This configuration may be suitable for radiation therapies delivered to the head and neck, and may be particularly suitable for use with treatment of oral cancers. For clarity, due to the number of different internal dosimeters that will be described, the oral cavity internal dosimeter will be referenced as internal dosimeter 530. The oral cavity internal dosimeter 530 includes a mouthpiece body 531 that holds the radiation sensitive component 63 (typically the MOSFET 63m) thereon or therein. The mouthpiece body 531 can be configured to be customized to fit a particular patient, or may be provided in predetermined size ranges. The mouthpiece can be configured as a bite block. The mouthpiece body 531 holds at least a portion of at least one radiation circuit 30c thereon and/or therein. The radiation circuit 30c includes a radiation sensitive component 63, typically a MOSFET 63m, at least one electrical trace 64, and electronic memory 67. The memory 67 is disposed between the reader contact tab portion 36 and the MOSFET 63m. The memory 67 can be positioned to reside within or outside of the oral cavity during irradiation.

In some embodiments, the MOSFET 63m is embedded as an integral component in the body of the mouthpiece. In other components, the MOSFET 63m and radiation circuit 30c can be held on a substrate that can be inserted into the mouthpiece (cutting into the body of the mouthpiece or into a channel formed into the mouthpiece). The mouthpiece can be configured to fit over the upper bite or lower bite of the user. The MOSFET 63m can be positioned in the body 531 so that the body shape and/or body tissue provides a suitable build-up therefor (see below for more discussion of build-up configurations).

In some embodiments, as shown in FIG. 2A, the dosimeter body 531 can hold a plurality of spaced apart radiation circuits 30c (shown as two radiation circuits, but other numbers can be used). In particular embodiments, at least one outwardly extending tab portion 36 (shown as two in FIG. 2A) can be configured to reside outside of the oral cavity during irradiation. FIGS. 3A-3C illustrate that the tab portions 36 may be of different extension lengths ($L_1$-$L_3$). In other embodiments, the tab portions 36 can be folded or held snug against or in the body 531 (not shown). FIG. 2B shows that the dosimeter 530' can have tab portions 36 that can reside in close proximity to the body of the mouthpiece 531. The outwardly extending portion of the dosimeter 530 may be generally rigid or generally resilient, but should be configured in a minimally intrusive manner to allow a user to close his or her mouth over the body during irradiation. The outwardly extending portions of the circuits 30c may have a thin film protective liner, coating, and/or elastomeric cover that can protect the circuit components from saliva and the like, but that can be selectively removed to allow a reader 75 (FIG. 30) to electrically contact the circuit 30c.

Figure 4A:
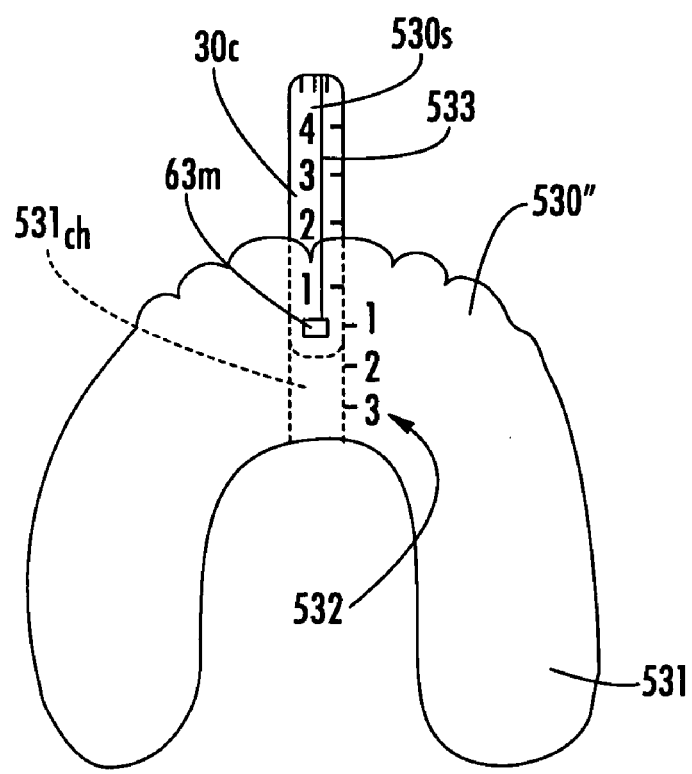
FIG. 4A is a top schematic view of another oral cavity dosimeter, which is configured to allow for adjustable placement of a dosimeter according to embodiments of the present invention.
Figure 4B:
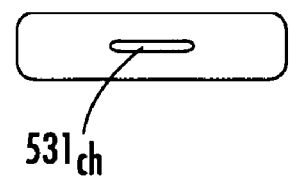
FIG. 4B is a front view of the device shown in FIG. 4A illustrating one position of an adjustment channel according to embodiments of the present invention.

As shown in FIG. 4A, in some embodiments, the dosimeter 530 can be configured to hold the MOSFET 63m of the radiation circuit 30c in a medial location. As also shown in FIG. 4A, in some embodiments, the radiation circuit 30c can be configured on a substrate 530s that can be positionally adjusted in situ. As shown in FIG. 4A, the substrate 530s can include an alignment scale 533 that cooperates with indicia on the body 531 that allows a clinician to slide the substrate 530s in or out to position the MOSFET 63m at a desired known evaluation location. For example, when the substrate 530s is positioned with "1" held at the boundary of the body 531, the MOSFET is held at "position 1" in the channel 531ch. The substrate 530s can be configured to frictionally engage the channel 531ch or other retaining means to hold the substrate at the desired location during use. FIG. 4B illustrates that the channel 531ch can be a subsurface channel that encloses the substrate 530s. However, in other embodiments, a channel 531ch can be formed on an upper or lower surface with a floor or ceiling partially open (not shown).

FIGS. 5A and 5B illustrate additional embodiments of an internal dosimeter 30i. This internal dosimeter 30i is referred to as dosimeter 630 and is a cavity dosimeter that can be sized and configured either as a nasal cavity plug or ear plug 630a, 630b, respectively. In some embodiments, the body of the dosimeter 631 has a generally cylindrical shape. The body 631 may comprise a conformable material (such as foam or similar materials) that encases at least a distal forward portion of the circuit 30c and allows the body 631 to be compressed, inserted and then expanded to fit in the target cavity. The tab portion 36 (where used) can also reside within the body of the dosimeter 631 or extend outwardly a distance from the body 631 to allow easy external access as shown. For the former, for embodiments where the tab portion 36 is used to communicate with the reader 75, the circuit 30c may be able to be pulled outward for access. FIG. 6 illustrates one example of a circuit 30c, which may be held on a flex circuit substrate 30s. The body 631 may be integrally molded about the circuit 30c to at least partially encase the circuit 30c or the circuit 30c may be releasably inserted into a chamber in the body 631. FIG. 5B illustrates a partial cutaway view of the dosimeter 630 with the radiation sensor circuit 30c held therein. As shown, the MOSFET 63m and memory 67 may disposed at a distal end portion 631d of the body 631. The body of the dosimeter 631 may be formed, shaped and/or filled with a material selected to provide a desired build up and/or the placement in the patient body cavity may provide suitable operational build-up for radiation detection and determination.

FIGS. 7A and 7B illustrate yet another internal dosimeter 30i. This internal dosimeter 30i is a genourinary catheter 730. The catheter 730 is flexibly configured so as to be able to bend and flex to follow the shape of the lumen or cavity (even those with curvatures as shown in FIG. 7A) as it is introduced into the lumen or cavity until a distal portion of the catheter 730 reaches the desired evaluation site. FIG. 7A illustrates that at least one radiation sensor circuit 30c can be held on an elongate flex substrate 30s with at least one MOSFET 63m (or other radiation sensitive element) held on a distal end portion thereof. The flex circuit substrate 30s can be held in the flexible catheter body 731. In other embodiments, portions of the circuit 30c may be formed on an inner or outer wall of the catheter body 731. In the embodiment shown in FIG. 7A, the catheter body 731 is a sheath that is sized and configured to receive at least a portion of the radiation circuit 30c therein. The proximal end portion of the radiation circuit 30c or flex substrate 30s may reside outside or inside the sheath. The memory 67 may reside on a proximal end portion of the radiation circuit 30c a distance away from the MOSFET 63m. In other embodiments, the memory 67 and MOSFET 63m can be proximately positioned at a distal end portion of the catheter body 731. The substrate 30s may be configured to slide into and/or out of the catheter body 731 to allow for positional adjustment of the MOSFET 63m within the subject. Radioopaque indicia can be placed on the catheter body 731 and/or substrate 30s and an imaging modality can image the device in position in the body to determine the position of the MOSFET 63m relative to the target location. In some embodiments, similar to the mouthpiece dosimeter 530 embodiment above, location indicia (typically on a graduated scale format) can be formed on the catheter body 731 as well as the substrate 30s and used to guide the positioning of the MOSFET 63m into a desired axial location.

FIG. 7B illustrates a catheter 730', similar to a Foley catheter, which has a urinary intake port 733p and channel 733 and anchoring balloon 734. The radiation circuit 30c can be held in fluid isolation from the urinary discharge channel 733 as shown, for example, in the two different cross-sections illustrated in FIG. 7C. As shown, the substrate 30s is held spaced apart from the urinary drain channel 733. In addition, in some embodiments, as shown in FIG. 7B, the urinary drain channel 733 may exit via a discharge port 735 in a different direction from the radiation circuit substrate 30s, thereby inhibiting fluid contamination of the tab portion 36 (where used). As such, as before, the tab portion 36 can reside outside or inside the catheter body (which includes the conduit leading thereto).

FIG. 7B illustrates that the MOSFET 63m can be positioned below the anchoring balloon 734, which in position, typically resides in the bladder neck (FIG. 7A). This can locate the MOSFET 63m in the prostatic urethra. The MOSFET 63m can be held in the catheter body above or within the balloon 734 region as well. For example, if the bladder is the target region, the catheter body 731 can be configured to extend a further distance distally and the MOSFET 63m can be positioned in the bladder neck or bladder. In addition, the dosimeter 730 (which is used to be inclusive of all derivatives 730 herein) can include a flex substrate 30s that holds a plurality of different axially spaced apart radiation circuits 30c and/or MOSFETs 63m as shown, for example, in FIG. 11.

The catheter dosimeter 730 can be provided in a range of different sizes (with the widths varying as well as the placement/size of the balloon) to accommodate different size males and different size prostates, particularly where the treatment under evaluation is the prostate. For example, the catheter 730 can be sized as an elongated tubular body with a relatively small cross-sectional area having a thin outer wall so as to be able to be inserted into and extend along a length of the desired lumen to reach the desired treatment site. As used herein, the term "thin outer wall" means a wall having a thickness of about 2 mm or less, and preferably about 1.2 mm or less, and can be, in certain embodiments about 0.5 mm or less. For prostate or male urinary applications, the cross-sectional width or outer diameter of the catheter tubular body, is typically between about 6-8 mm (18-24 French). Of course, as noted above, the flexible catheter 730 can be alternatively sized and dimensioned to fit other lumens, cavities and/or treatment applications.

FIGS. 8 and 9 illustrate female catheters 730", 730''', respectively, that are configured with an anchoring balloon 734 and at least one radiation circuit 30c on a flex circuit substrate 30s. The catheter 730' shown in FIG. 8 is sized and configured for the urethra and bladder while that shown in FIG. 9 can be sized and configured for the cervix and/or uterus. As for the male catheter shown in FIG. 7A, the anchoring balloon 734 may not be required and other anchoring means may be used to hold the radiation circuit in position. FIG. 9 illustrates at least one MOSFET 63m at a distal end portion of the catheter body 731. The length of the female catheter and associated substrate 30s and/or radiation circuit 30c may be less than that of the male catheter and respective substrate 30s and/or circuit 30c. The width of the substrate 30s and/or catheter body may also be different.

Figure 10:
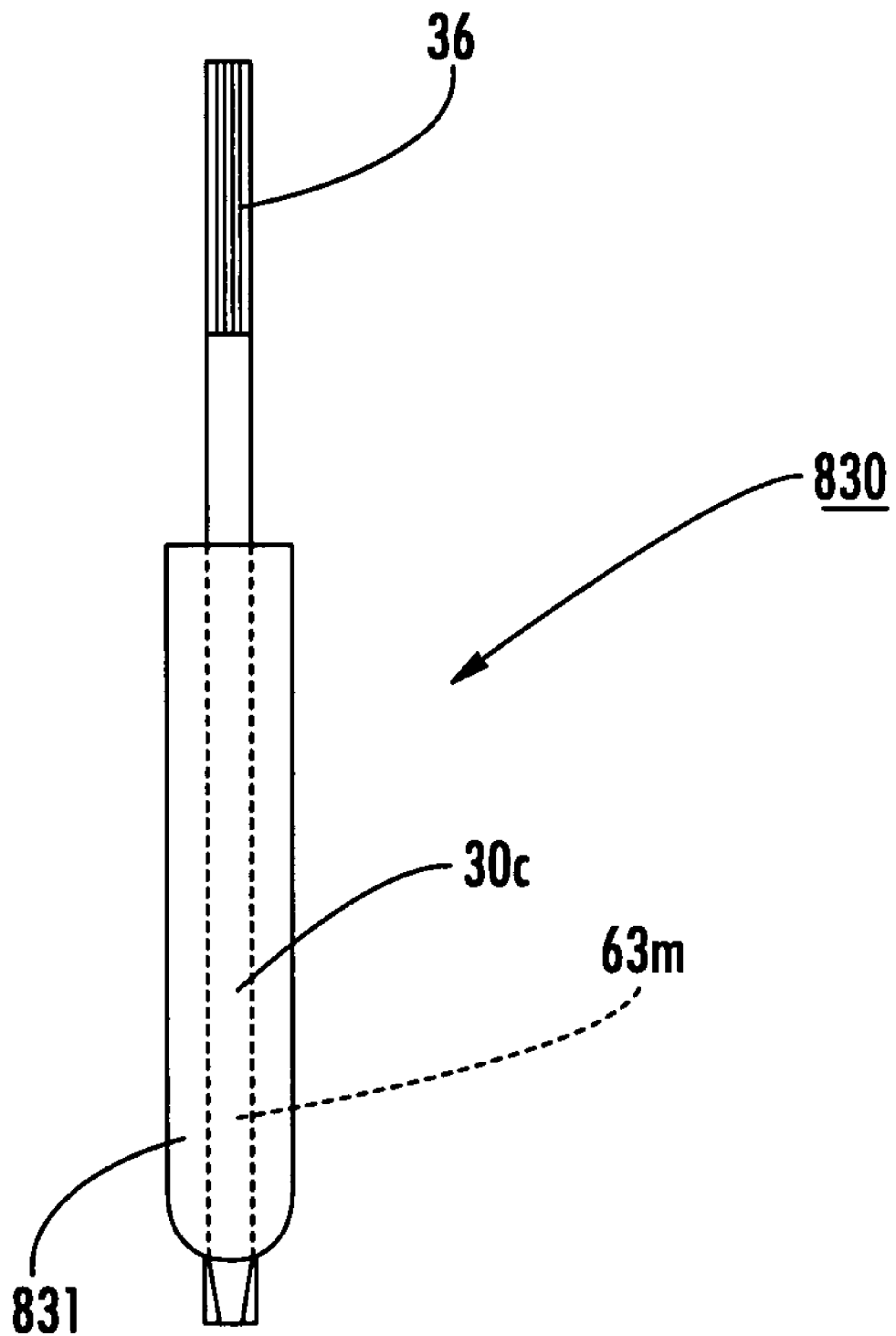
FIG. 10 is a side view of an internal probe according to yet other embodiments of the present invention.

FIG. 10 illustrates an elongate plug body dosimeter 830 suitable for both rectal and vaginal insertion (when sized appropriately). As shown, the body of the dosimeter 831 is generally cylindrical and may be formed in a tampon or suppository-like shape. The body 831 is generally less flexible, more structurally rigid, and/or shorter than that of the catheters 730 described above. As shown, the tab portion 36 may extend outwardly a distance from the primary body of the dosimeter 831. One or more radiation circuits 30c and/or MOSFETs 63 may be held in the body of the dosimeter 831, typically on a common flex substrate 30s, although non-flexible substrates may also be used. In some embodiments, the body 831 can hold a plurality of separate substrates 30s with each having at least one radiation circuit 30c (not shown). The body 831 may be formed of absorbent or non-absorbent material, but should be configured to remain in position during irradiation. If the body comprises absorbent material, then the radiation circuit 30c may be coated with a protectant material. Similar to the nasal and ear plug embodiments described above, the radiation sensor circuit 30c and/or substrate 30s can be configured to slide into the body 831, or the body 831 can be molded thereabout to form an integral device. The body 831 may comprise an internal channel (not shown) sized to receive the substrate 30s and allow adjustable positioning of the MOSFET 63m, as with other embodiments described above. In addition, the build-up of the device 830 can be provided by the shape of the body 831 and/or the intrinsic build-up provided upon positioning in the body.

FIG. 11 illustrates a substrate 30s (typically a flex circuit substrate) that holds a plurality of radiation circuits 30c and respective axially spaced apart MOSFETs 63m thereon that can be used in internal dosimeters contemplated by the instant invention. Each MOSFET 63m can evaluate radiation at a different position, and, as noted above, each radiation circuit 30c may function independently of the others, or may share certain ancillary components and memory 67. The multi-sensor substrate 30s can be used with any of the internal dosimeter embodiments described herein.

In the embodiment shown in FIG. 12, the substrate 30s can be inserted into a sheath and/or catheter body 931 that is sized and configured to form an internal dosimeter 30i suitable for entering one or more of a catheter in a set of HDR (high dose) brachytherapy, radiation therapy, catheters. As shown in FIGS. 13A and 13B, the catheter set is held in a grid and the catheters positioned transcutaneously. In operation, a number of open catheters are placed in the target treatment region (breast, prostate or other) in a matrix or grid format. Then, a "hot" radiation source, such as Ir-92, is "snaked" into the catheters and run in and out over a certain time to deliver the high-dose radiation. The internal dosimeter 930 can be inserted into a selected catheter to provide radiation data that can be compared to conventional projected dose estimates (provided by a software program based on dwell time and average tissue attenuation). The reader 75 can be configured to automatically input the actual data into a computer that can compare the projected and actual data in real time to provide feedback that can be used to adjust the treatment. A multi-sensor line of radiation circuits/MOSFETs 63m can provide overlapping readings as the source runs in and out of the catheter. The internal dosimeter 30*i* can be configured to provide dose data after one pass of the HDR source. The dosimeter 30*i* can be used in one dedicated open catheter or used in one or more of the operative catheters.

Figure 14:
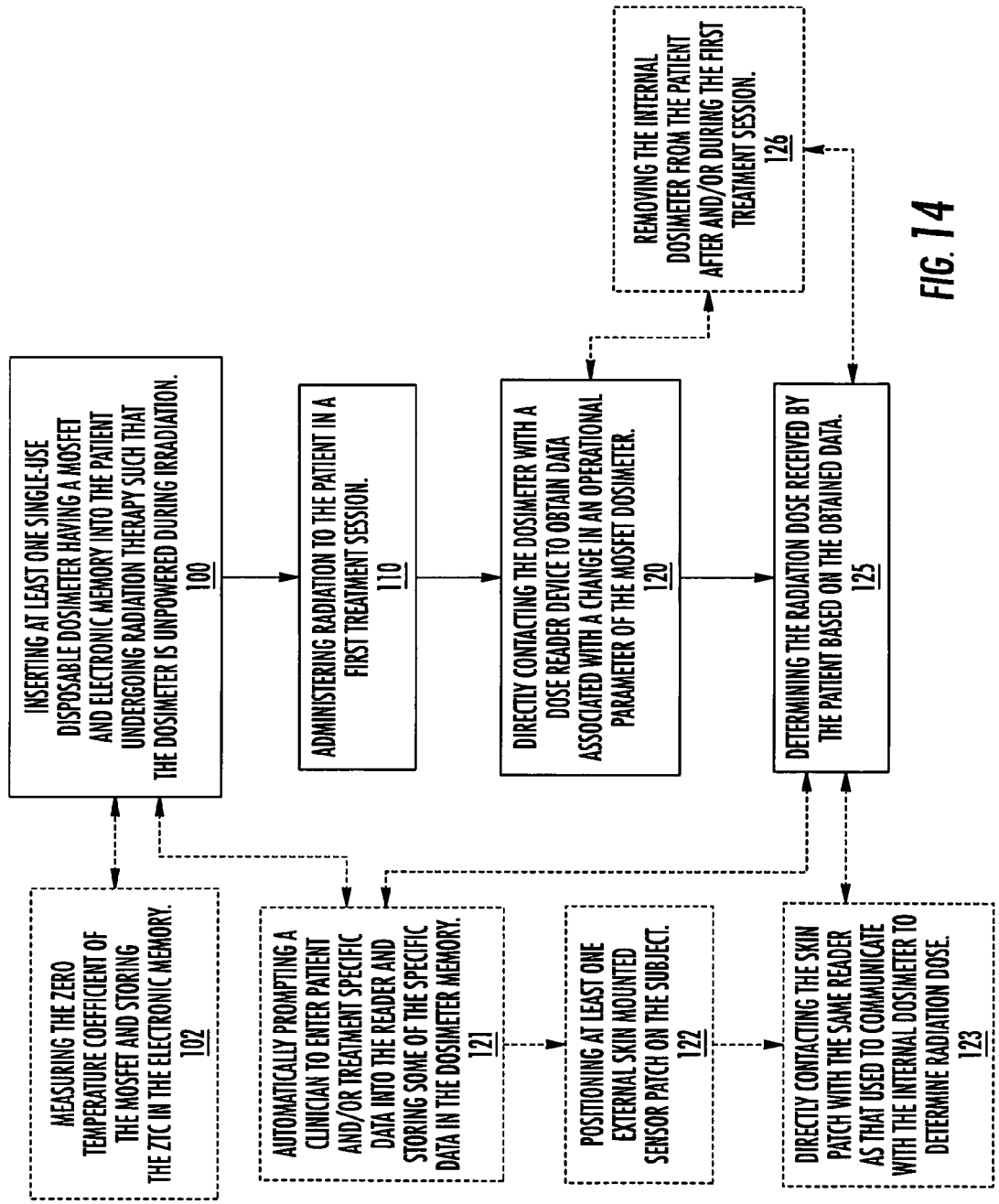
FIG. 14 is a block diagram of operations for monitoring patients undergoing therapy.

Referring to FIG. 14, operations that can be carried out to monitor the radiation dose that is delivered to a patient undergoing therapy are illustrated. At least one single-use internal dosimeter having a MOSFET and electronic memory can be inserted into the patient (block 100). Radiation can be administered to a patient in a first treatment session (block 110) and the dosimeter can be directly contacted with a reader device to obtain data associated with an operational change in the MOSFET (block 120). The radiation dose can be determined based on the obtained data (block 125).

The internal dosimeter is typically removed during, at the end of, or after the first treatment session (providing a single use evaluation) (block 126). A clinician can be automatically prompted by the reader to enter specific data into the reader, some of which can be stored in the memory in the dosimeter (block 121). In addition, at least one skin mounted dosimeter patch may be placed on the subject (block 122) and the same reader can be used to contact the patch to obtain additional radiation data, that may be used to determine a radiation dose (block 123). The prompting operation can be carried out prior to, during, and/or after the treatment session.

Similarly, the dosimeter can be removed prior to reading by the reader or read in position in the body.

In certain embodiments, as noted above, the internal dosimeter may be calibrated and/or pre-dosed and/or the zero temperature coefficient can be measured and stored in the memory before being inserted into the patient. The calibration and/or pre-dosing of the sensor patch may be done on an individual patch basis or many sensor patches may be calibrated and/or pre-dosed in batches simultaneously as discussed further below.

In certain particular embodiments, the reading may be able to be obtained in situ during the treatment session (without removing the sensor patch(es) from the patient) to provide real-time feedback to the clinician estimating whether the desired dose is being administered to the patient. In certain embodiments, the temperature of the sensor patch (such as at a location adjacent the circuitry) or of the subject (skin or core body) can also be ascertained or obtained and taken into account when calculating the radiation dose. In any event the dose reading can be obtained without requiring external powering or externally applied biasing of the MOSFET 63*m* in the sensor circuit 30*c* during the radiation treatment.

In certain embodiments, a plurality of discrete sensor patches 30 can be positioned to cover a region on the skin that is in the radiation beam path so as to reside over a target treatment site (typically diseased tissue associated with a tumor site). Further, in particular embodiments, one or more sensor patches 30 can also be positioned in radiation sensitive areas of the body to confirm stray radiation is not unduly transmitted thereto. Sensitive regions include, but are not limited to, the thyroid, the spine, the heart, the lungs, the brain, and the like.

In any event, radiation is administered to the patient in a first treatment session. Data associated with a change in an operational parameter in the patch radiation circuit and the internal dosimeter radiation circuit may be obtained from the sensor patch using the reader after/during administering the radiation to the patient. In further embodiments, the reader may contact the sensor patch as discussed further below. However, it is noted, that in other embodiments, the reader may transfer data from the internal dosimeter and/or sensor patch wirelessly. The radiation dose received by the patient can be determined based on the obtained data.

In some embodiments of the present invention, the obtained data may include a voltage threshold of a metal-oxide semiconductor field-effect transistor (MOSFET) included in the radiation circuit 30*c* of the internal dosimeter 30*i* and, where used, on the at least one sensor patch 30. In these embodiments of the present invention, a pre-radiation voltage threshold of the MOSFET and a zero temperature coefficient of the MOSFET may be measured before the patient undergoes radiation therapy. The pre-radiation threshold voltage and the zero temperature coefficient of the MOSFET may be stored in the electronic memory of the dosimeter. The stored zero temperature coefficient may be used to bias the MOSFET on the internal dosimeter 30*i* and the least one sensor patch 30 (where used) after the patient undergoes radiation therapy and before the post-radiation threshold voltage is measured as discussed further below.

It will be understood that the radiation dose may be automatically determined by the reader 75 without any input by a doctor or technician. However, in some embodiments of the present invention, the doctor or technician may be prompted for additional information by the reader 75 to determine the radiation dose. For example, the reader 75 may prompt the technician for a correction factor related to a particular set-up or radiation equipment type employed or a particular configuration of the dosimeter (ie, whether internal 30*i* or external 30). Once the clinician supplies the requested additional information, the reader 75 may automatically determine the radiation dose using the additional information provided. The obtained data, as well as other information, may be stored in an electronic memory (memory device) included on the dosimeter (patch or internal).

In particular, the electronic memory may include methodology data that instructs the reader 75 how to interface with, i.e., obtain data from the radiation circuit 30*c*. Thus, for example, if the radiation circuit 30*c* changes electronic configuration, the memory 67 can be configured to automatically instruct the reader 75 on how to obtain the radiation and other patch data of interest, allowing the reader 75 to operate with different versions of patches. In other embodiments, the reader 75 can be periodically upgraded with software to communicate with the different versions of patches. Combinations of these configurations may also be used.

The electronic memory may further include radiation-dose data, patient data, time and date of a radiation reading, calibration data and the like. Furthermore, as discussed above, the electronic memory may include the zero temperature coefficient of a MOSFET included in the radiation circuit 30*c*. This zero temperature coefficient may be used to bias the MOSFET after the radiation treatment before a post-radiation threshold voltage is obtained as discussed further below.

The internal dosimeter 30*i* (and, where used, the sensor patch 30) does not require lead wires extending from a remote power source or computer system to operate (i.e., is basically inactive and/or unpowered) during irradiation. For example, where a MOSFET-based radiation sensor circuit is used, the MOSFET is generally passive but collects a permanent space charge as a result of the passage of ionizing radiation. After radiation exposure or at a desired evaluation time, the biosensor(s) can be inductively powered and the MOSFET-based radiation data can be transferred to a remote reader.

In some embodiments, the dosimeter 30*i* can transmit or relay radiation data upon contact with and/or insertion into a reader device 75 and may store data in an electronic memory device 67 included in the dosimeter 30*i*. As discussed above, in other embodiments, the internal dosimeter 30*i* may be configured to communicate wirelessly with the reader 75. The radiation dose received by the dosimeter 30i and/or sensor patch 30 can be determined and used to estimate the dose received by the patient during the radiation therapy session based on the data obtained by the reader. The reader 75 itself can be a handheld portable unit that may or may not require wires to connect with a remote controller or computer or may use a standard communication port as will be discussed further below. The reader 75 can include a user input such as a touch screen and/or keypad entry. In any event, the operations can be carried out for each or a selected radiation treatment session. If the operations are repeated for each treatment session, a cumulative amount of delivered radiation can be estimated/confirmed to allow a clinician to evaluate whether additional treatments are desired.

In certain embodiments, data may be included in the memory storage device 67, for example, an electrically programmable memory such as an electrically erasable read only programmable memory (EEPROM), for each dosimeter 30i. The memory storage device 67 may include information such as patient identification, time, date, hospital, therapist, state of the device, dosed/undosed sensor data and calibration data. The memory storage device 67 may further be used to store bias parameters and/or information with respect to measurement methodology for a particular individual dosimeter 30i. For example, the measurement methodology may include instructions for the reader 75 on how to communicate with the radiation circuit 30c in the dosimeter 30i. Including these instructions in the memory storage device may allow the reader 75 to operate with any version of the dosimeter 30i and/or sensor patch 30 as the reader 75 may not have to be configured for the specifications of a particular dosimeter. The memory 67 may also include data that identifies the type of internal dosimeter it is. In some embodiments of the present invention, the memory storage device 67 of the sensor patch 30 may have at least 2K of storage thereon.

The MOSFET 63m in the radiation circuit 30c can have an individual calibration coefficient, dose data or characterizing data. In other embodiments, those MOSFETS produced in a common production run (off of the same wafer or chip) with substantially similar characterizing data may have common single calibration characterizing data. In certain embodiments, the calibration related characterizing data can include the pre-irradiation threshold voltage value of a MOSFET(s) that is measured at an OEM and provided in the memory 67.

In some embodiments, the memory storage device 67 may include a zero temperature bias parameters associated with the MOSFET included in the dosimeter 30i. The zero temperature coefficient of the MOSFET may be measured prior to administration of radiation therapy to the patient and stored in the memory storage device 67. The zero temperature coefficient of the MOSFET may be used to bias the MOSFET before obtaining a post-radiation threshold voltage value of the MOSFET as discussed further below.

Referring now to FIG. 29, Table 1 summarizes exemplary specifications for the internal dosimeter 30i and/or sensor patch 30 according to some embodiments of the present invention. It will be understood that the specifications provided in Table 1 are provided for exemplary purposes only and that embodiments of the present invention should not be limited to this configuration/features.

In certain embodiments, a first set-up pre-dose verification protocol can be carried out to deliver a first radiation dose and a first radiation dose value can be obtained for at least one selected patch 30 and/or internal dosimeter 30i to confirm that the radiation beam focus location is correct or suitable (or whether a sensitive area is receiving radiation). In addition, the system can be configured to map a dose gradient by correlating the determined radiation dose values at each patch location to the anatomical location on the subject of each patch.

In certain embodiments, the storage or memory device 67 (FIG. 30) can be retained to form a portion of the medical records of a patient and may be accessed to determine dosing information etc. if this information fails to be recorded, is misplaced or requires verification. Accordingly, the memory device 67 may serve as an electronic dosimetry patient record form.

Figure 15:
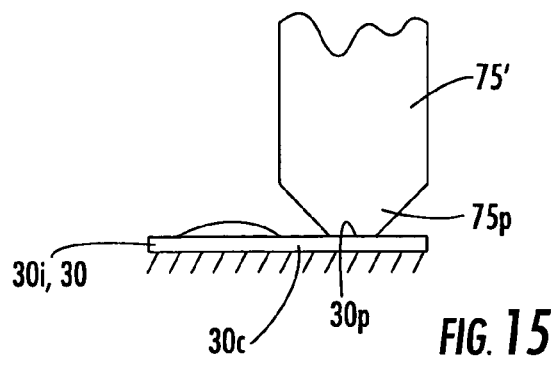
FIG. 15 is a schematic illustration of exemplary embodiments of a reader contacting the sensor to obtain the radiation dosage data according to still further embodiments of the present invention.

FIG. 15 illustrates a reader or data acquisition device 75' according to embodiments of the present invention, in point contact with the underlying radiation circuit 30c in order to detect the amount of radiation exposure during (or after) the treatment session. The reader 75' can be configured with a probe 75p that is configured to electrically contact an electrically conductive probe region so as to obtain a reading in a "short" time of under about 30 seconds, and typically in less than about 5-10 seconds, for each of the sensor patches 30.

Figure 16A:
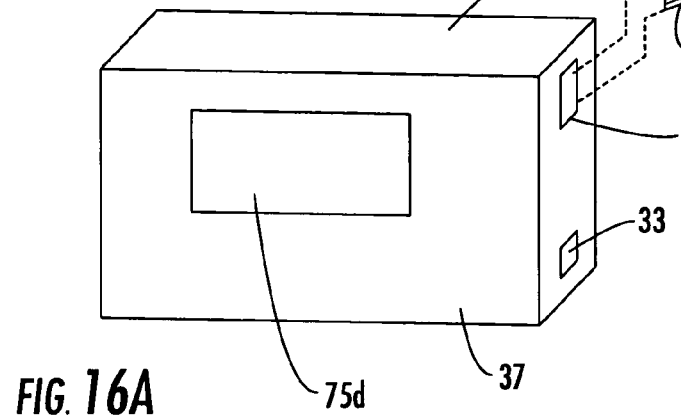
FIG. 16A is a schematic illustration of further embodiments of a reader configured to receive a portion of the dosimeter in a sensor port, and optionally, can also receive a portion of a skin mountable dosimeter patch, to obtain the radiation dosage data according to some embodiments of the present invention.
Figure 16B:
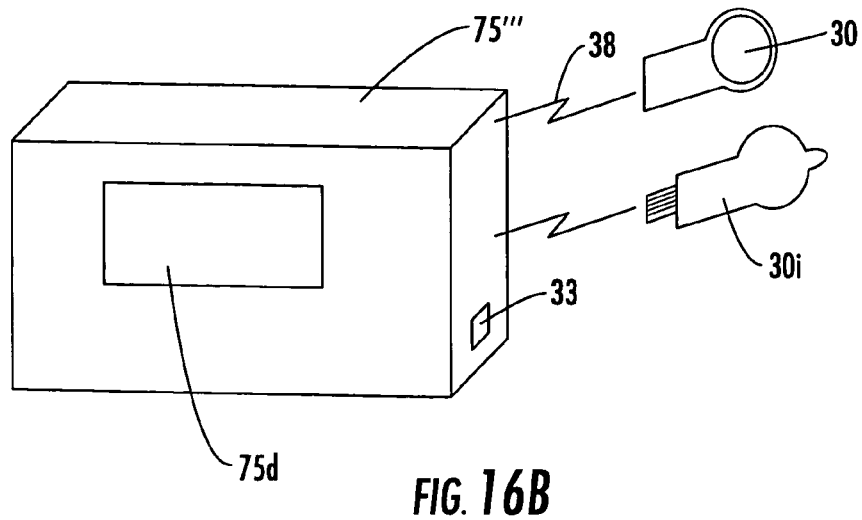
FIG. 16B is a schematic illustration of still further embodiments of a reader receiving wireless communications from the sensor to obtain the radiation dosage data according to further embodiments of the present invention.

Referring now to FIG. 16A, a reader or data acquisition device 75 is adapted to receive (a portion of) the internal dosimeter 30i and the internal dosimeter 30i may be adapted to be inserted into the reader 75. As shown, the internal dosimeter 30i can include a tab portion 36 that is sufficiently rigid to sustain its shape for proper electrical coupling when inserted into a port 32 in the reader device 75 to transmit the radiation data. The term "tab portion" includes any member configuration that provides coupling to the reader 75, although, for internal dosimeters 30i, the tab portion can be a relatively short portion of the overall length of the radiation circuit 30c. The port 32 may be configured similar to conventional devices that read, for example, glucose strip sensors and the like. The port 32 illustrated in FIG. 16A may contain one or more electrical contacts configured to contact one or more electrical contacts on the dosimeter tab portion 36 to electrically connect the reader 75 to the radiation circuit 30c. FIG. 16B illustrates that the reader 75 and dosimeter 30i (and, in some embodiments, patch 30) can wirelessly communicate.

Figure 17B:
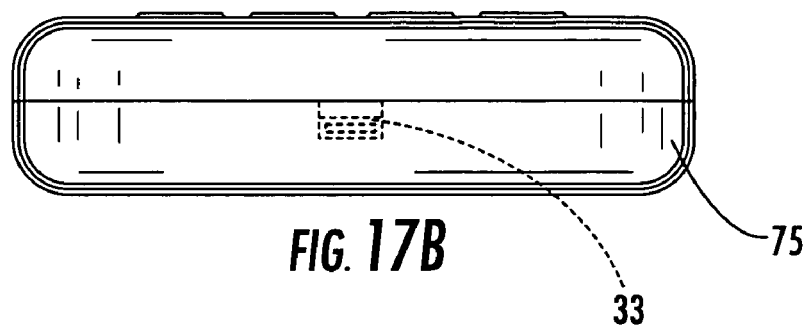
FIG. 17B is an end view of the reader shown in FIG. 17A.
Figure 17A:
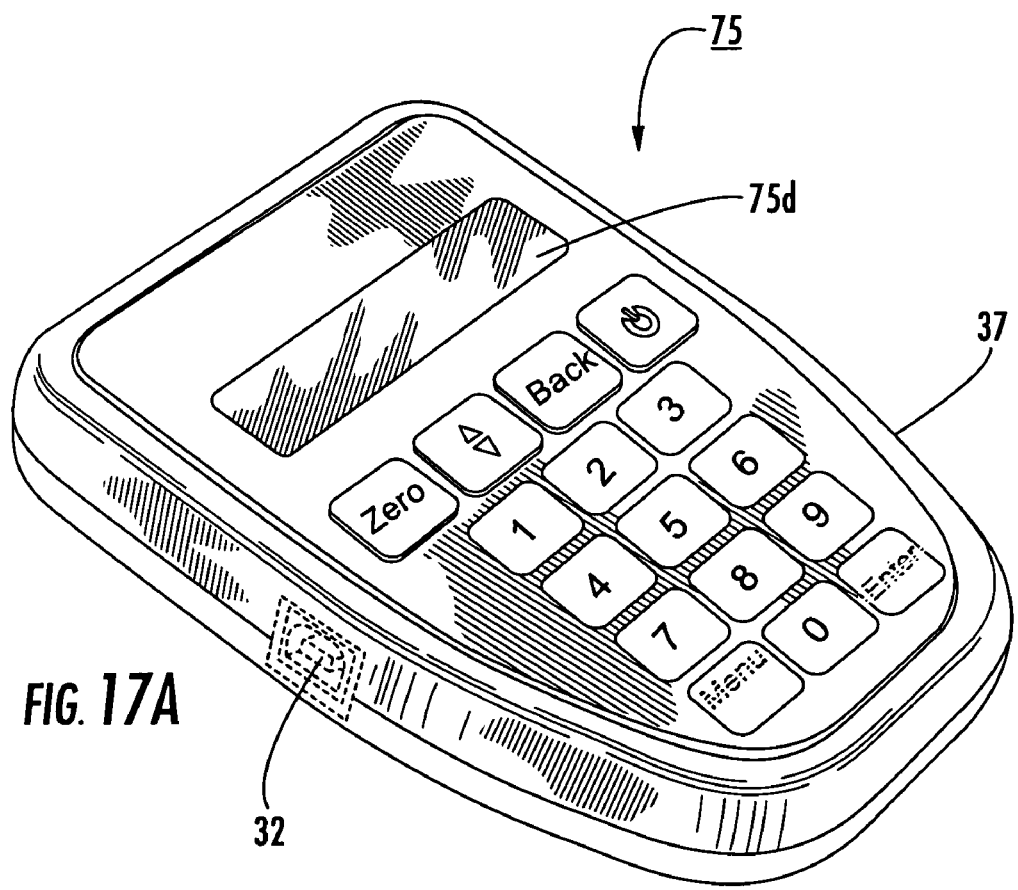
FIG. 17A is a side perspective view of an exemplary portable hand-held reader according to embodiments of the present invention.

Referring to FIGS. 17A and 17B, the reader 75 can be held in a portable housing 37 that can include a radiation dosimeter port 32. It may be pocket-sized and battery powered. In certain embodiments, the reader device 75 may be rechargeable. As shown in FIG. 17A, the reader 75 may include a display portion 75d, for example, a liquid crystal display (LCD), to provide an interface to depict data to the doctor and/or technician.

The function of the reader 75 may be incorporated into any portable device adapted to communicate with an internal dosimeter 30i (and, in certain embodiments also a sensor patch 30). For example, the reader 75 fuctionality/circuitry could be disposed in a personal digital assistant (PDA) that is adapted to include a radiation sensor port 32. The reader 75 may further include a remote computer port 33. The port 33 may be, for example, RS 232, infrared data association (IrDA) or universal serial bus (USB), and may be used to download radiation and/or other selected data from the internal dosimeter 30i to a computer application or remote computer.

In certain embodiments, the reader 75 may be configured to obtain data stored in the memory device 67 of the dosimeter 30i using, for example, electrical contacts on the reader 75 and the dosimeter 30i, to transfer the data stored in the memory device 67. This data obtained from the memory device 67 may, for example, be stored locally on the reader 75 or be downloaded to an application on, for example, a remote computer using a port 33 provided in the reader 75. The memory device 67 may serve as a permanent record of the radiation dose and may contain a real time clock such that the obtained data may include a time and date stamp.

Figure 31:
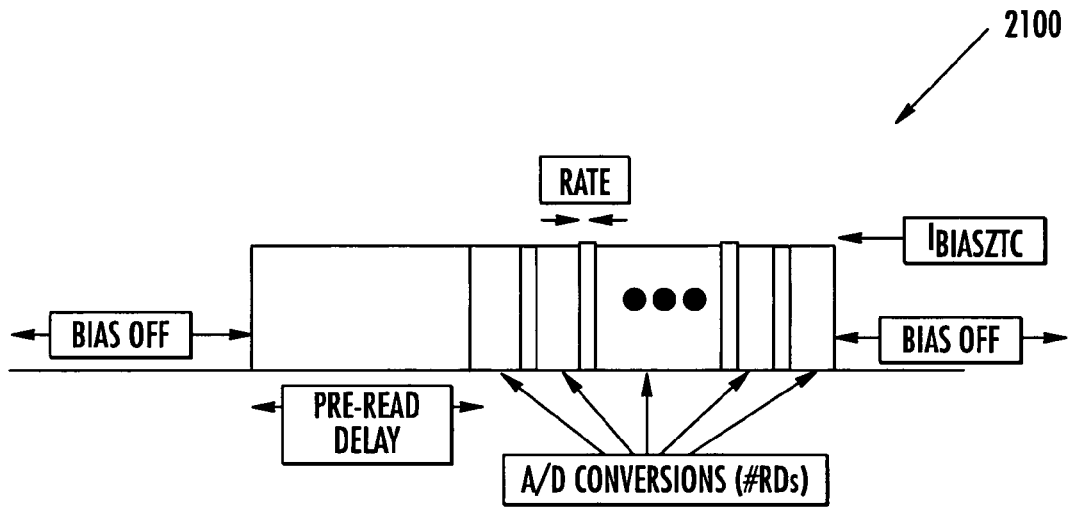
FIG. 31 is a block diagram illustrating a process for modifying conversion parameters and bias timing according some embodiments of the present invention.

An exemplary block diagram of a reader 75 and an internal dosimeter 30i including a RADFET 63 and an electronic memory 67 according to some embodiments of the present invention is provided in FIG. 30. It will be understood that the block diagram of the reader 75 and the dosimeter 30i and sensor patch 30 of FIG. 30 is provided for exemplary purposes only and embodiments of the present invention should not be limited to the configuration provided therein. Furthermore, a flow diagram 2100 of FIG. 31 illustrates how a number of reads, a read delay and/or a rate may modify conversion parameters of the RADFET according to some embodiments of the present invention.

The sensor patch(es) 30 can be configured as a discrete, low profile, compact non-invasive and minimally obtrusive device that conforms to the skin of the patient. The sensor patch(es) may be less from about 0.25 to about 1.5 inches long and wide and have a thin thickness of from about 1 to about 5 mm or less. In certain embodiments of the present invention, the sensor patch 30 can be attached to the patient so that it makes and retains snug contact with the patient's skin. Air gaps between the sensor 30 and the patient's skin may cause complications with respect to obtaining the estimated dosage data.

Some embodiments of the present invention include the placement of an overlay material over the sensor patch 30 to, for example, simulate placement of the sensor patch 30 beneath the patient's skin. This type of simulation may inhibit scatter of the radiation beam and/or establish electronic equilibrium in proximity to the sensor patch 30 and, therefore, increase the reliability of radiation measurement. Radiation measurement using the sensor electronics may be optimal at from about 0.5 to about 3 cm beneath the patient's skin, but typically is from about 1 to about 1.5 cm beneath the patient's skin. Accordingly, the overlay material may be from about 0.5 to about 3 cm thick to simulate subsurface depth measurement conditions. The presence of this overlay material may decrease the influence of air gaps between the sensor 30 and the patient's skin. The overlay material may be, for example, a resilient flubber like or flexible material that will conform to the skin such as an elastomeric or the like. Some embodiments of the present invention include the placement of a buildup cap over the sensor patch 30 to, for example, simulate placement of the sensor patch 30 beneath the patient's skin. This type of simulation may help to focus a narrow portion of the radiation beam in proximity to the sensor patch 30 and, therefore, increase the reliability of radiation measurement. The buildup cap may have a hemispherical shape and may simulate placement of the sensor patch 30 inside the body to a depth called "Dmax". Dmax may be, for example, from about 1 to about 3 cm and is the depth at which the absorbed dose reaches a maximum for a given energy. The buildup cap may include a material equivalent to water and a metallic material. For example, the buildup cap may include a layer of polystyrene having a diameter of from about 6 to about 7 mm and a layer of copper on the polystyrene have a thickness of about 0.5 to about 1 mm. The buildup cap may include a small lip (not shown) that hooks onto the front edge of the patch for consistent alignment. The buildup cap may have a medical grade adhesive that would stick well, but not permanently, to the top face of the sensor patch 30. In some embodiments of the present invention, the geometry of the cap could be made to help with isotropy. The buildup cap may be placed on the sensor patch 30 separately based on the energy range of the buildup cap, thereby allowing the underlying sensor patch 30 to be used with different buildup caps for different energy ranges. In some embodiments of the present invention, the buildup caps may be provided in different colors, the colors indicating the energy range of the buildup cap. Thus, in some embodiments of the present invention, the bulk of the buildup cap may be injection molded polystyrene that is coated with a copper layer and some rubbery or elastomeric surface paint applied in different colors corresponding to the different energy ranges provided by the buildup cap. The buildup cap can also be shaped to provide a measurement that is independent of X-ray beam entry angle. With respect to the discussion in the preceeding paragraphs, it is noted that for internal dosimeters 30i, their build-up can be provided by shape and material of the probe body, alone or in combination with the tissue at the target internal location.

Figure 18:
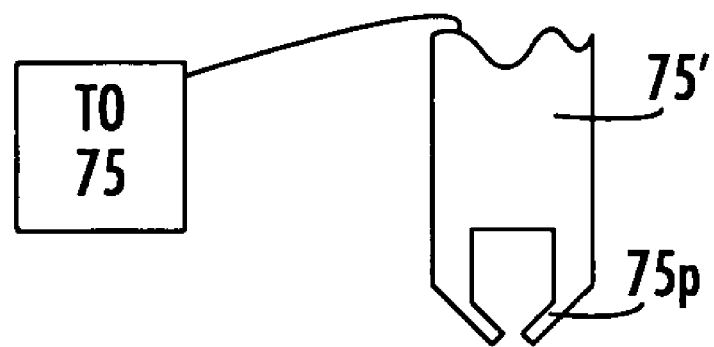
FIG. 18 is a partial cutaway view of a probe head for a reader according to some embodiments of the present invention.

FIG. 18 illustrates that the reader 75 can include a probe portion 75p. As illustrated, the probe portion 75p may be configured so that the probe 75p includes, for example, conductive calipers, pinchers, or other piercing means, that can penetrate to make electrical contact with the probe contacting region of the radiation circuit 30c.

Figure 19:
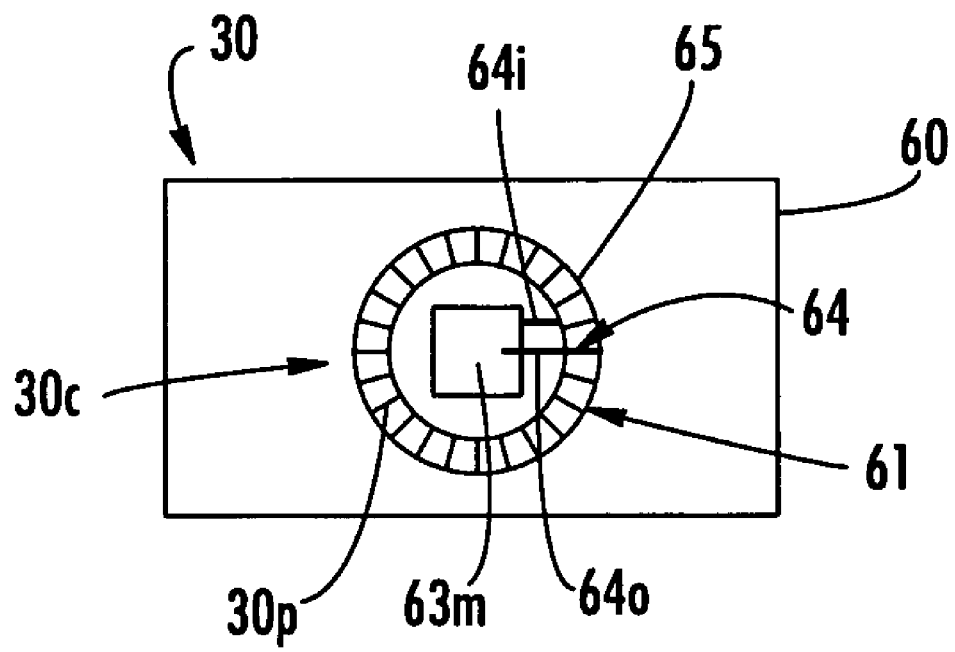
FIG. 19 is a schematic illustration of embodiments of a sensor patch with a circuit thereon according to further embodiments of the present invention.

FIG. 19 illustrates a top view of embodiments of a circuit layer 61. As shown, the circuit layer 61 includes the radiation sensitive operative sensor circuit 30c that is self-contained and devoid of outwardly extending or hanging lead wires that connects to an operational member during irradiation. The sensor patch circuitry 30c includes a radiation sensitive device 63 that exhibits a detectable operational change when exposed to radiation. In certain embodiments, the radiation sensitive device 63 is a miniaturized semiconductor component such as a MOSFET 63m. Suitable MOSFETs include RADFETs available from NMRC of Cork, Ireland. In certain embodiments, the MOSFET may be sized and configured to be about 0.5-2 mm, or less, in width and length, with the flex circuit being configured to accommodate the particular dosimeter use (the flex circuit substrate may be longer for certain internal dosimeters than for the patches). The circuitry 30c also includes at least one conductive lead or trace 64 extending from the MOSFET 63m to the conductive probe contacting region 30p. In the embodiment shown, the conductive probe contacting region 30p is an annular ring, but other configurations may be used. As also shown there are two traces 64i, 64o that connect the device 63m to the ring 30p. The traces or leads 64 may be formed, placed, or deposited onto the substrate layer 30s in any suitable manner including, but not limited to, applying conductive ink or paint or metal spray deposition on the surface thereof in a suitable metallic pattern, or using wires. As desired, an upper layer 62 such as described above (such as epoxy) may be formed over the circuit layer 61. The sensor patch 30 may include integrated Electro Static Discharge (ESD) protection, the reader 75 may include ESD protection components, or the user/operator may use ESD straps and the like during readings. The same or similar circuit configurations may be used on an elongate flex circuit substrate 30s used for the internal dosimeters 30i described above.

In other particular embodiments, the sensor circuit 30c can be configured with two or more MOSFETS. In embodiments configured to have two MOSFETS, one may be positioned over the other on opposing sides of the substrate in face-to-face alignment to inhibit orientation influence of the substrate. (not shown). Additionally, other materials, e.g. certain epoxies, can be used to both encapsulate the MOSFETs and provide further scattering influence to facilitate isotropic response of the MOSFETs (this feature may particularly apply to the skin patch dosimeters 30). In addition, there are well known influences of radiation backscatter from the surface of patients on whom surface-mounted dosimeters are used. The backscatter effect can be taken into account when calculating an entrance or exit dose or sufficient build-up may be provided on the top of the dosimeter to promote the equilibration of scattered electrons. See, *Cancer, Principles and Practice of Oncology*, 3d edition, ed. V T DeVita, S. Hellman, and S A Rosenberg (J B Lippincott Co., Phila., 1989), the contents of which are hereby incorporated by reference as if recited in full herein. The underside or bottom of the sensor patch 30 may include a medical grade releasable adhesive to allow the sensor patch 30 to be secured to the skin during the treatment session and then easily removed without harming the skin.

Figure 20A:
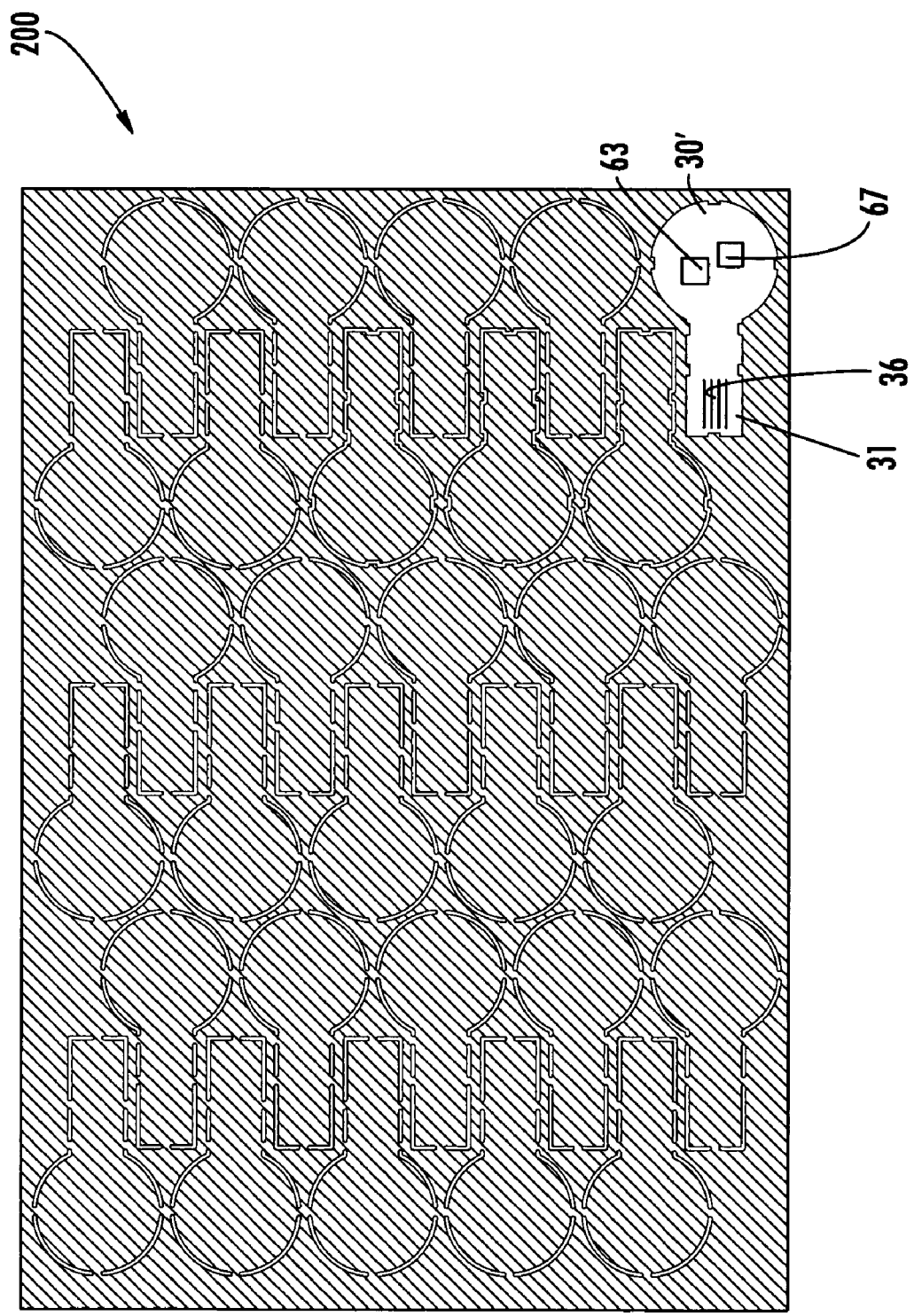
FIG. 20A is a schematic illustration of a sheet of sensors according to embodiments of the present invention.

Radiation circuits 30*c* according to embodiments of the present invention may be provided individually or in sheets containing multiple circuits 30*c*. In particular, the sensor flex substrates 30*s* may be fabricated in high-density sheets. As used herein, "high density" refers to multiple sensor patches provided on a unitary sheet. High density is intended to encompass very large sheets containing, for example, hundreds or thousands of sensors, as well as, for example, 3×3 regions of these very large sheets typically including 6 or more sensors per region. Providing the sensor circuit substrates 30*s* including memory devices 67, for example EEPROMs, on high density sheets 200 as illustrated in FIGS. 20A through 20D provide the capability of calibrating and/or pre-dosing the entire sheet at one time. As shown in FIG. 20A, the sheets 200 may include perforations for subsequent separation of the individual sensor patches 30 from the high density sheet 200. Similar configurations are contemplated for elongate internal dosimeter 30*i* circuits 30*c*. Thus, although shown configured as a typically shaped sensor patch, the substrates can be configured to provide the desired radiation circuit shape for the internal dosimeters as well. In certain embodiments, the sheet of sensors 200 may include from about 30 to about 100 sensors 30*s* per sheet.

Figure 20C:
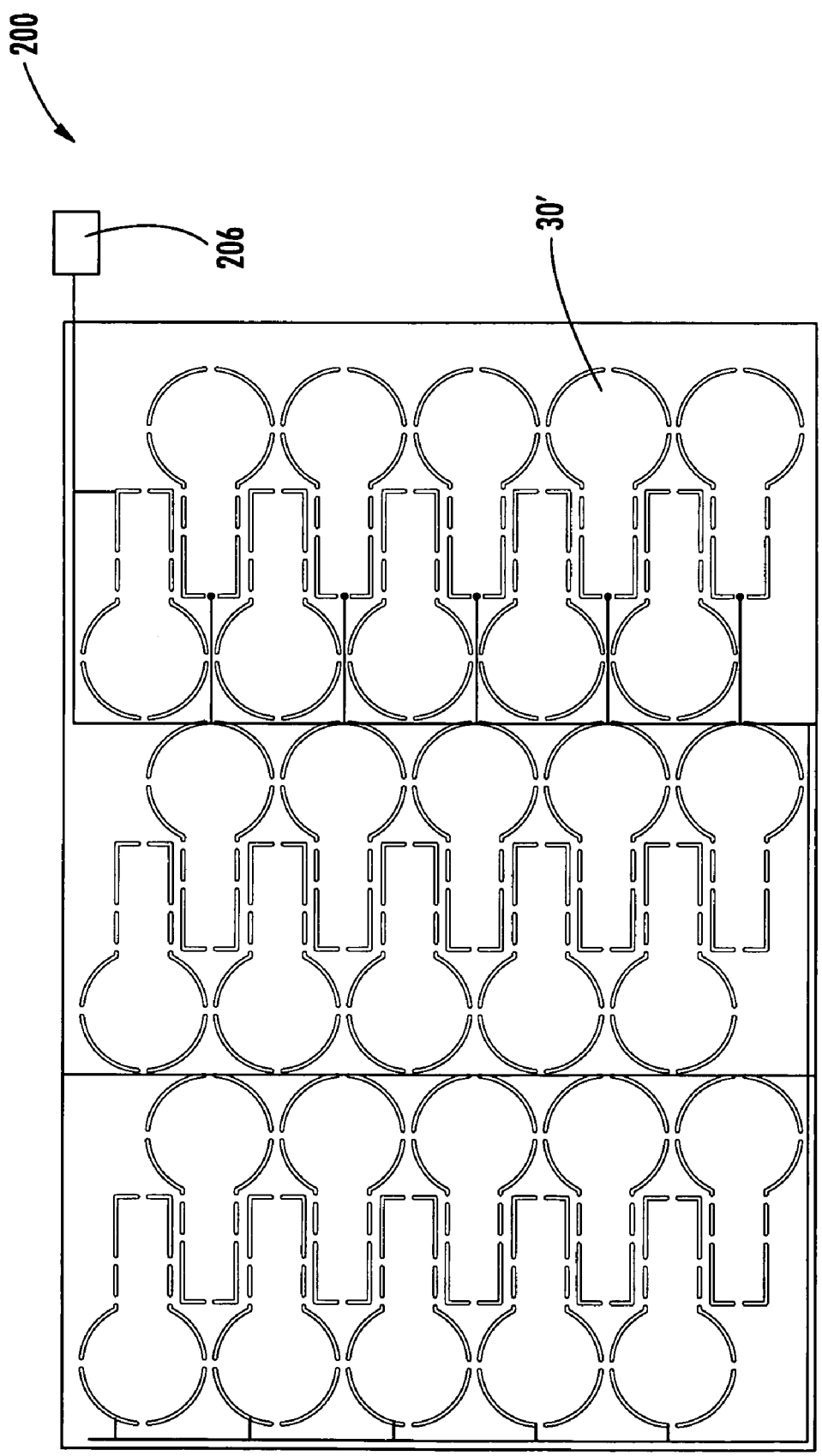
FIG. 20C is a schematic illustration of a sheet of sensors according to still further embodiments of the present invention.
Figure 20D:
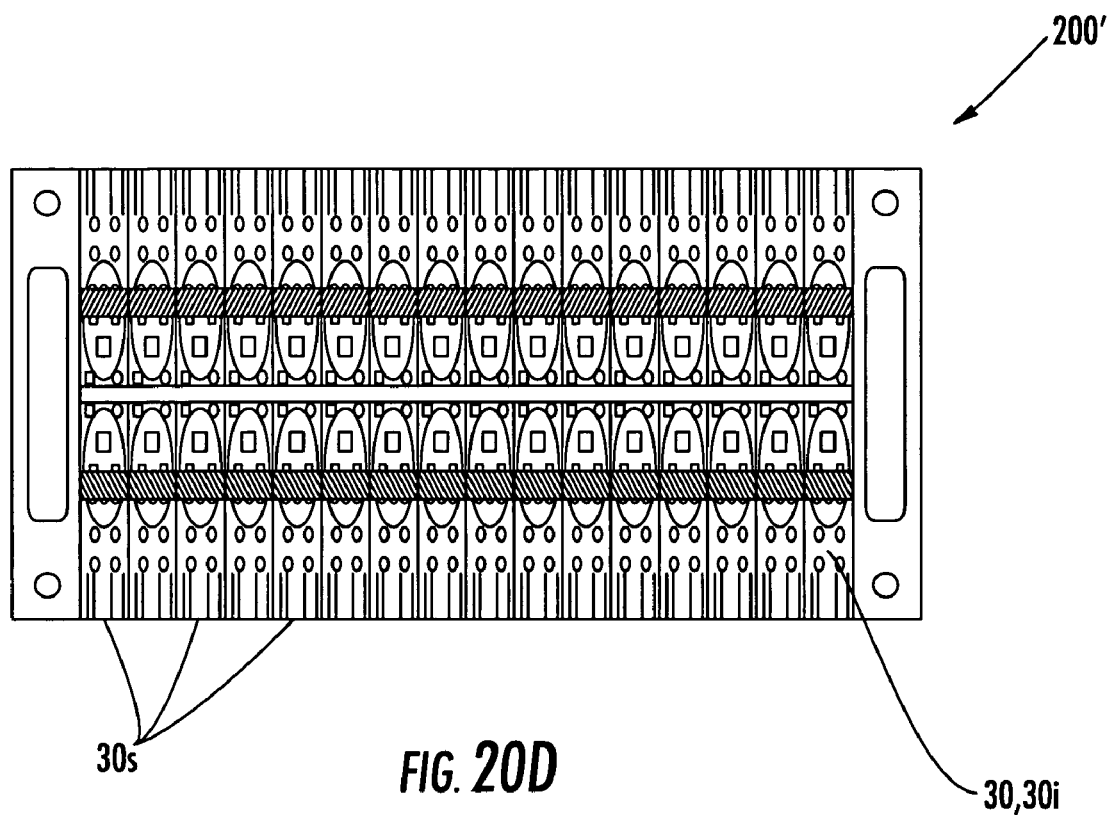
FIG. 20D is still a further schematic illustration of a sheet of sensors according to some embodiments of the present invention.

As further illustrated in FIG. 20D, in some embodiments of the present invention, the sensors 30*c* may be configured in an array 200' of 16×2 sensor circuits 30*c*. This arrangement may provide a method of processing 32 patches in a single batch. Each patch or radiation circuit 30*c* may be singularized, i.e., detached from the other sensors in the batch, in the final processing steps. In some embodiments of the present invention, the dimensions of the array may be selected so that the sheet fits within a 6" diameter cylinder, such as a cylindrical blood irradiator chamber. The final assembly may be calibrated using a research irradiator, blood irradiator, LINAC or other radiotherapy equipment without departing from the teachings of the present invention. It will be understood that calibration techniques known to those having skill in the art may be used to calibrate the radiation circuits 30*c* according to some embodiments of the present invention.

Each of the sensors 30*c* or the entire sheet 200 of sensor circuits 30*c* may be calibrated by providing a wire(s) 205 illustrated in FIG. 20B that electrically couples each of the sensors 30*c* on the sheet 200. For ease of reference, only a single electrical line to one sensor is shown on FIG. 20B. The calibration data may be provided to the sensors 30*c* through the wire(s) 205 and may be stored in the respective memory storage device 67. The ability to calibrate a plurality of sensors 30*c* simultaneously may provide more precision in the dosimetry process and, therefore, possibly more reliable results. It will be understood that the sensors 30*c* may each have a dedicated wire or the sheet can have a calibration line all connected to a common lead 206 as shown in FIG. 20C that may be used to calibrate and/or pre-dose the sensor circuits 30*c* individually.

As discussed above, the sensor circuits 30*c* may be pre-dosed, i.e. dosed prior to placement on the patient. Dosing a sensor patch may include, for example, setting the amount of radiation to be delivered to a patient and the particular region (s) on the patient to which the radiation should be delivered. This process is typically performed by a physicist and can be very time consuming. The possibility of accurately pre-dosing a sensor circuit 30*c* may reduce the need for a physicist to be involved in the dosimetry confirmation process. In other words, using reliable dose patches can reduce the time a physicist expends to confirm the treatment beam and path dose.

It will be understood that dosimeters 30*i* adapted to be received by a reader 75 are not limited to the configuration illustrated in the figures provided herein. These figures are provided for exemplary purposes only and are not meant to limit the present invention.

Figure 32:
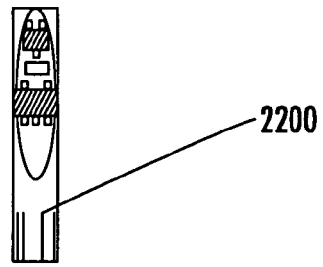
FIG. 32 is a schematic diagram of a test strip according to further embodiments of the present invention.

Some embodiments of the present invention provide a test strip 2200 as illustrated in FIG. 32. The test strip 2200 may allow the functionality and calibration of the reader 75 to be tested and verified. According to some embodiments of the present invention, the test strip 200 may consist of a sensor patch including an EEPROM and a resistor and a voltage reference instead of the MOSFET/RADFET. Thus, in the event that the reader 75 is, for example, left in the radiation treatment beam, has a mechanical failure or the like, a 4.096 V reference or a current source may be altered and, therefore, may yield incorrect dose readings. The test strip 2200 may provide an external reference that may be used to verify proper operation and calibration of the reader 75.

As stated above, the test strip 2200 may be similar to the sensor patch 30 and/or selected internal dosimeter 30*i*, except the RADFET may be replaced with a series combination of a voltage reference and a resistance, for example, a 1.2V shunt reference (specified at 0.1% tolerance such as an LM4051-1.2) and a 10KΩ resistor (0.1% tolerance). In some embodiments of the present invention, the gate/drain connection may have a 39KΩ, 0.1% tolerance resistor coupled to ground on the test strip 2200. The 39KΩ resistor may provide an additional 52 µA bias to the series 1.2V reference and 10 KΩ resistor.

The test strip 2200 may include a memory map, which may include, among other things, the defaults from the base load (at the ZTC process), i.e. the pre-radiation data. Table 7 of FIG. 41 contains a listing of functional specifications of test strips according to some embodiments of the present invention. It will be understood that the functional specifications listed in FIG. 41 are provided for exemplary purposes only and that embodiments of the present invention are not limited to this configuration.

The reader 75 may interrogate the test strip memory and request that a doctor technician perform a "zeroing operation" discussed further below. The test strip 2200 may be zeroed and the resulting digital to analog conversion (DACB) value may be compared to the DACB value determined at the factory. The result may indicate, for example, "Reader OK" if the DACB value is within a set of limits provided or "Reader needs Cal" if the DACB value is outside the set of limits. It will be understood that the limits may be determined on a per-reader basis during factory calibration.

In certain embodiments of the present invention, the test strip 2200 may be configured to prevent modification by the reader 75. In some embodiments of the present invention, the reader may be configured to indicate "Reader OK" when the test strip 2200 is inserted and a predetermined reference voltage, such as about 4.096 V, is within a predetermined range. The reader may be further configured to indicate "Reader needs Cal" if the reference voltage is outside of the predetermined range. In some embodiments of the present invention, the predetermined range may be from about 4.075 to about 4.116V. The tolerance on the limits may be about +/−0.005V.

It is noted that the remainder of the specification may discuss the sensor circuit 30c and/or MOSFET 63m in relation to the sensor patch 30, but the same concepts and/or functions can be used for certain embodiments of the circuit 30c of the internal dosimeters 30i.

Figure 21:
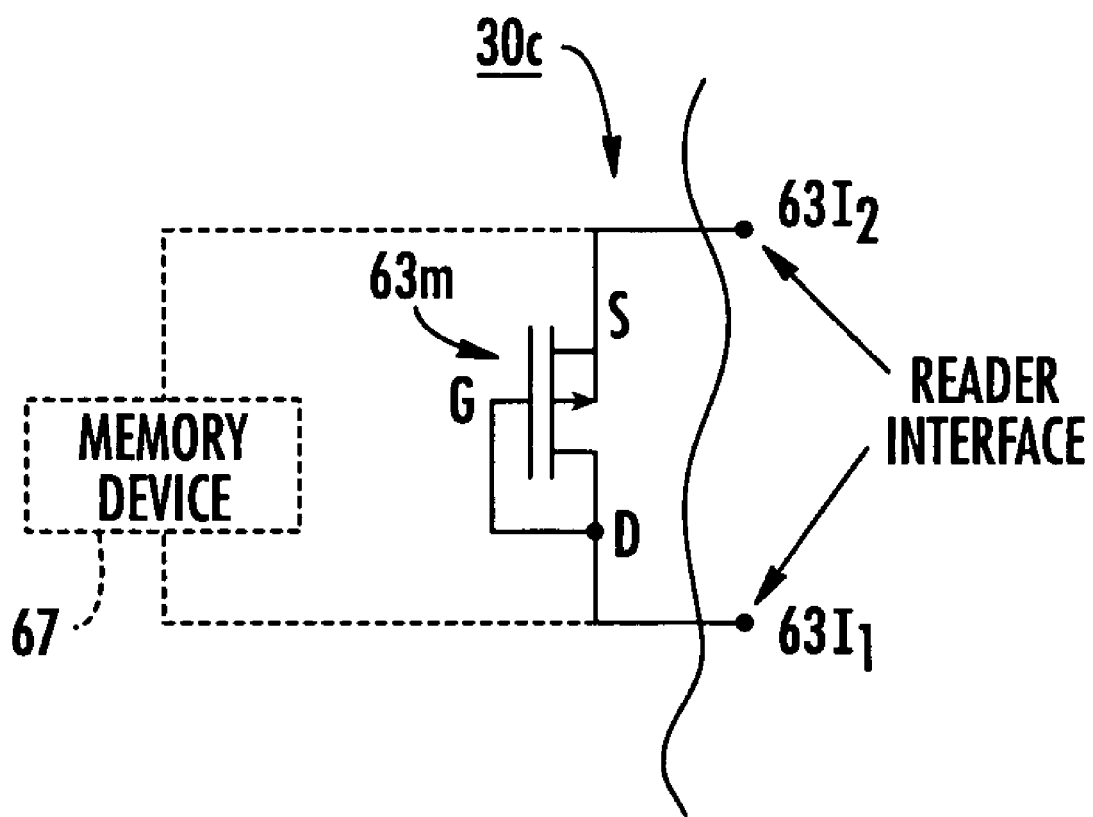
FIG. 21 is a schematic of a circuit diagram of a MOSFET sensor with a reader interface and an optional memory according to some embodiments of the present invention.

As shown in FIG. 21, in certain embodiments, the radiation sensitive device 63 is a RADFET. The RADFET can be biased with a gate/drain short so that it acts as a two-terminal device. FIG. 21 illustrates a portion of the circuit 30c with a RADFET 63 and two associated reader 75 interface or contact points $63I_1$, $63I_2$. FIG. 22A illustrates a reader 75 (upper broken line box) and the circuit 30c (lower broken line box) with the RADFET 63 configured with a gate to drain short. As shown, the reader 75 can include a RADFET bias circuit 75b that includes a controlled current source to allow a voltage reading to be obtained corresponding to the threshold voltage of the RADFET.

As shown by the graph in FIG. 22B, changes in surface state charge density induced by ionizing radiation causes a shift in threshold voltage in the RADFET.

FIG. 22B illustrates a radiation response of a standard P210W2 400 nm implanted gate oxide RADFET with lines for 0V (the -0- marked line) and 5V (the line with the -*- markings) irradiation bias responses. To obtain the amount of threshold voltage ("Vth") shift, the Vth value (zero dose) can be subtracted from the post-irradiation value and the calibration curve used to determine radiation dose. The calibration curve can be pre-loaded into the controller of the reader or a computer to provide the dose data. In certain embodiments, when obtaining the readings, the clinician may wear grounding straps to reduce static sensitivity of the circuitry. In certain embodiments, such as where contact points are exposed, ESD protection may be integrated into the sensor patch 30 or dosimeter 30i itself.

As shown in FIG. 22A, the Vth change can be measured by determining the change in applied gate voltage necessary to induce a set current flow. As noted above, the RADFET characterization data can be obtained prior to exposure to radiation (zero dose). Thus, the starting threshold voltage of the sensor 30c will be known from a priori information (or can be obtained by the clinician prior to placing on the patient or after on the patient but before radiation exposure) and can be placed in the reader 75 or computer associated or in communication therewith.

FIG. 23 illustrates the threshold voltage relationship between output voltage (voltage) and current Ids (the electrical current, drain-to source, in microamps) as measured using the output voltage of the reader circuit shown in FIG. 22A. In operation, the reader circuit is configured to contact the sensor to provide a constant current source to the circuit so as to be able measure Vth at a substantially constant or fixed bias condition.

In some embodiments of the present invention, the zero temperature coefficient of the MOSFET/RADFET 63m (FIG. 21) may be obtained. The zero temperature coefficient of a MOSFET refers to a specific bias current level at which the threshold voltage of the MOSFET does not change significantly with temperature variation in the range of temperatures likely to be encountered according to some embodiments of the present invention. Although the zero temperature bias current typically varies from one MOSFET to another, it is a parameter that may be measured before the administration of radiation therapy to the patient and stored, for example, in the memory device 67, along with the pre-radiation threshold voltage of the MOSFET measured when the MOSFET is biased with the zero temperature bias current. After recording and storing these parameters, the patch 30 or internal dosimeter 30i may be exposed to radiation and inserted into the reader 75 or wirelessly coupled to the reader 75. The MOSFET may be biased with the stored zero temperature bias current (which the reader 75 may obtains from the memory device 67) and the post-radiation threshold voltage of the MOSFET may be measured. The change in the threshold voltage, i.e., the difference between the pre-radiation threshold voltage and the post-radiation threshold voltage, may be used by the reader 75 to calculate the radiation dose. It will be understood that in these embodiments of the present invention the MOSFET is not operated in a biased configuration or otherwise powered during the radiation treatment session.

The memory device 67 may include a memory map identifying memory locations and contents thereof. In some embodiments of the present invention, the memory map may resemble a spreadsheet. The memory map may include one or more fields containing data, such as serial numbers, calibration factors, dose records, time stamps, biasing parameters, factory calibration information and the like. The reader 75 may access data stored in the memory map using, for example, a standard I2C protocol as discussed further below. Details with respect to memory maps will be understood by those having skill in the art and will not be discussed further herein.

In some embodiments of the present invention, the dose may be calculated using Equation 1 set out below:

$$Dose = k_{energy} * k_{rate} * k_{SSD} * k_{fieldsize} * k_{temp} * k_{wedge} * k_{fade} * [a(v_{shift})^3 + b(v_{shift})^2 + c(v_{shift}) + d]$$ (Equation 1)

Figure 33:
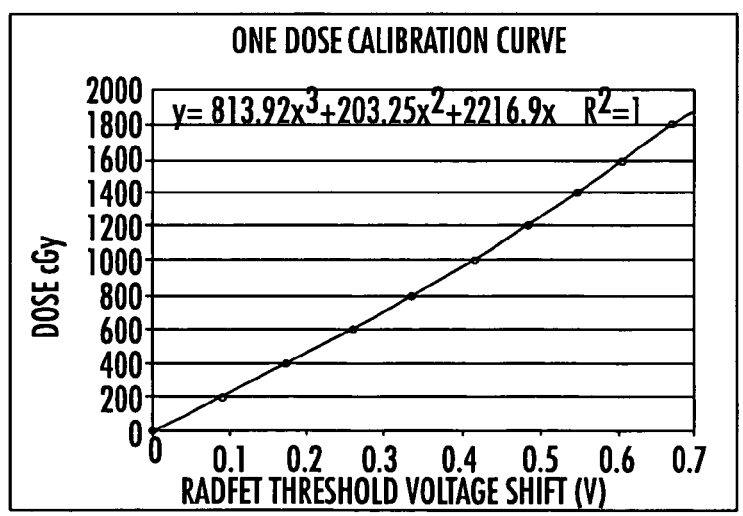
FIG. 33 is a calibration curve illustrating a dose response of an exemplary MOSFET/RADFET according to still further embodiments of the present invention.

$V_{shift}$ is the voltage difference (as seen by the 24-bit A/D converter) between the pre-radiation and post-radiation threshold voltage when measured at the zero temperature coefficient current ($I_{BiasZTC}$) discussed below. $k_{energy}$ (Energy), $k_{rate}$ (Dose Rate), $k_{SSD}$, $k_{fieldsize}$ (Field Size), $k_{temp}$ (Temperature), $k_{wedge}$ (Wedge Angle), $k_{fade}$ (Fade Time) (See FIG. 35) and/or other correction factors (collectively the "k-factors") may be stored in memory locations of the memory map stored in the electronic memory 67. In some embodiments of the present invention, if a coefficient is required, the reader may prompt the user for the coefficient during the zeroing operation. A calibration curve illustrating a dose response of an exemplary MOSFET/RADFET according to some embodiments of the present invention is provided in FIG. 33. It will be understood that the calibration curve provided in FIG. 33 is provided for exemplary purposes only and that embodiments of the present invention are not limited by this example.

Figures 34, 35, 36:
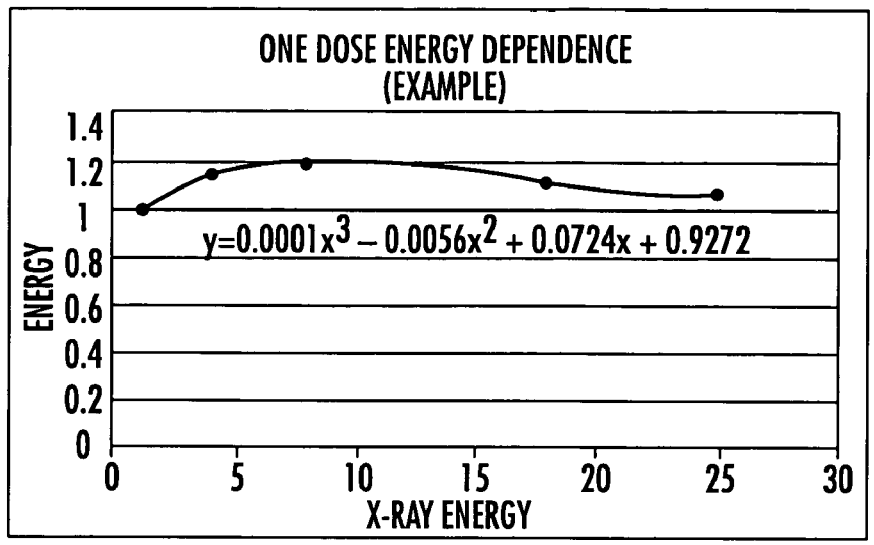
FIG. 34 is a graph illustrating an exemplary correction factor for energy dependence according to some embodiments of the present invention.
FIG. 35 is a table illustrating exemplary "k-factors" that may be applied to a dose equation according to further embodiments of the present invention.
FIG. 36 is a table illustrating an order of storing temperature correction coefficients according to still further embodiments of the present invention.

As necessary, correction factors may be applied for energy, dose rate, field size, temperature, wedge factors, fading or other user-defined corrections. The reader 75 can be configured to provide automatic prompts to a user or a station to obtain the desired patient-specific or equipment inputs. Coefficients for the correction factors may be stored in the electronic memory 67. User-input correction factors may also be stored in the reader 75 non-volatile memory and may be copied into the electronic memory 67 as a record if the correction factors are used in the dose calculation. A graph set out in FIG. 34 illustrates and an exemplary correction factor for energy dependence. It will be understood that the graph provided in FIG. 34 is provided for exemplary purposes only and that embodiments of the present invention are not limited by this example.

Referring to FIG. 34, the correction factors are curve-fitted to a 3rd-order polynomial and the coefficients may be stored in the memory cell locations of the memory map in the electronic memory 67. In some embodiments of the present invention, the default values may be 0, 0, 0, 1 for a, b, c, and d, respectively. Table 2 of FIG. 35 sets out exemplary "k-factors", discussed above, that may be applied to the dose equation set out in Equation 1 above.

In particular, temperature correction factor coefficients may be stored in the memory locations of the memory map stored in the electronic memory 67. In some embodiments of the present invention, the temperature correction factor coefficients may be stored in a floating point format. The coefficients may be stored in the order illustrated in Table 3 of FIG. 36 illustrating temperature correction coefficient locations.

The standard temperature may be normalized to about 20° C. The correction factors may be curve-fitted to a 3rd-order polynomial and the coefficients may be stored in the memory map 67. The default values may be, for example, set to 0, 0, 0, 1 for a, b, c, and d, respectively. The input to the equation may be the temperature in ° C. determined by calculating the temperature (° C.). This is calculated from the difference in a diode reference voltage and a diode voltage measured during the post-radiation process. The difference may be multiplied by the diode temperature coefficient stored in the memory 67 and added to 27° C. plus 1/10th of $T_{offset}$ discussed below.

For example, the patch temperature may be determined according to Equations 2 and 3 set out below:

$$V_{Diode} = 2.048 - (V_{ADC\_Diode} - 800000h) * 4.096/224 \quad \text{(Equation 2)}$$

$$\text{Temperature} = 27 + 10*(T_{Offset}) + (V_{Diode} - \text{Diode Voltage Reference})/\text{Temp Coeff. of the Diode} \quad \text{(Equation 3)}$$

Figures 37, 38, 39:
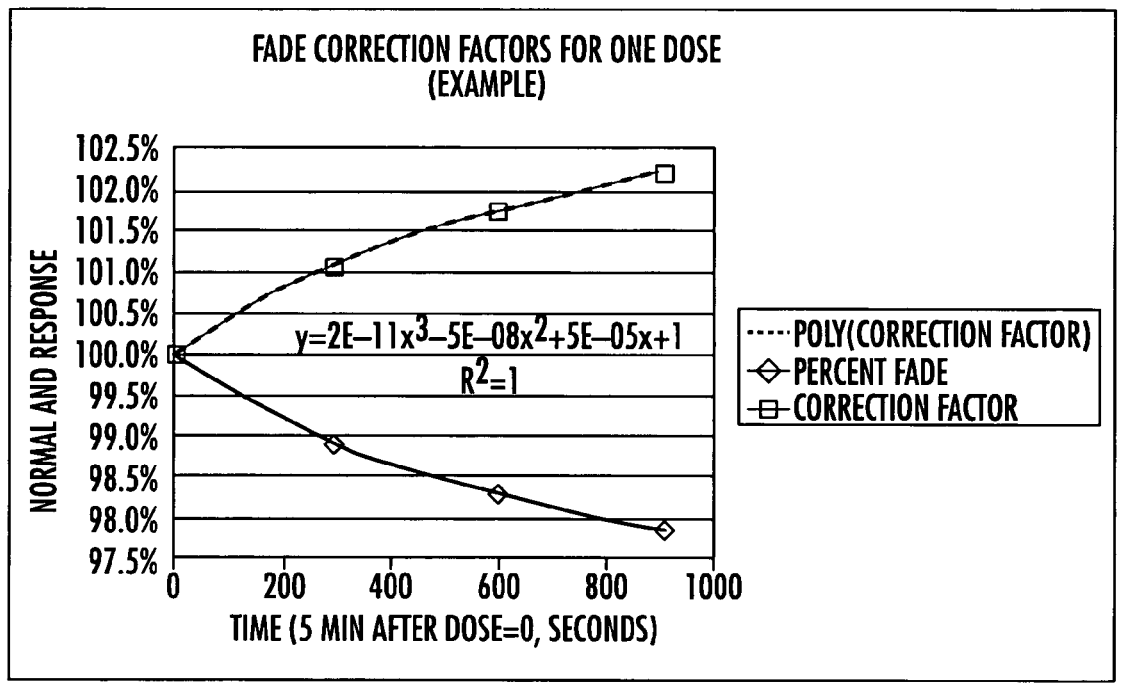
FIG. 37 is a table illustrating an order of storing fade correction coefficients according to some embodiments of the present invention.
FIG. 38 is a graph illustrating an exemplary response for fade in the RADFET voltage following a dose application according to further embodiments of the present invention.
FIG. 39 is a table including V/I relationships of readers according to still further embodiments of the present invention.

Furthermore, fade correction factor coefficients, i.e., coefficients of the correction factors for fading of the RADFET voltage, may be stored in the memory locations of the memory map stored in the electronic memory 67. In some embodiments of the present invention, the fade correction factor coefficients may be stored in a floating point format. The coefficients may be stored in the order illustrated in Table 4 of FIG. 37 illustrating fade correction coefficient locations.

The standard time may be normalized to about 300 seconds (5 minutes). The correction factors may be curve-fitted to a 3rd-order polynomial and the coefficients may be stored in the respective locations in the patch memory 67. The default values may be set to 0, 0, 0, 1 for a, b, c, and d, respectively. The input to the dose equation (Equation 1) is the difference in time (seconds) between the Dose-End timestamp and the Reading Time versus the 300 second normalized time. For example, if the reading takes place 5 minutes and 30 seconds after the dose end time, the input to the dose equation (Equation 1) would be 30 seconds. If the reading takes place 4 minutes after the dose end time, then the input to the equation would be −60 seconds.

In some embodiments of the present invention, the user may be prompted to input, such as via a touch sensor or a keypad, to indicate the end of the dose treatment. If there are multiple fields of radiation involved, the user may be instructed to press the timestamp button during the last treatment field. The time difference may be calculated (in seconds) between the dose end time and the reading time and may be used to correct for fade. If the prompt for dose time is not configured (in the reader) then the Zero-reading time plus 300 seconds may be used as the dose end time. A graph set out in FIG. 38 illustrates an exemplary response for fade in the RADFET voltage following a dose application.

The cells of the memory map may further include a standardized hex-coded D/A Converter value that may be used to bias the RADFET 63 to the factory-determined zero temperature bias current (ZTC). The value of the ZTC current may be determined at the factory and may be stored in the memory device 67 during the calibration process for each individual sensor. The value that may be stored in the memory device 67 is the D/A value and would be written if the particular reader reference voltages, D/A (assume 16-bit), resistor values, offset voltages and bias currents are ideal. For example, if the factory determined ZTC current is:

$$i_{Bias\_ZTC} = 10.00 \, \mu A \quad \text{(Equation 4)}$$

The value of the ZTC current stored in the memory device 67 ($I_{BiasZTC}$) during the calibration process for each individual sensor may be calculated using Equation 5 set out below.

$$I_{BiasZTC} = ((V_{4.096} - i_{Bias\_ZTC} * R_{Bias})/V_{4.096}) * 2^{16} \quad \text{(Equation 5)}$$

In some embodiments of the present invention, the parameters used in this calculation may be: $V_{4.096} = 4.096$ V, $V_{2.048} = 2.048$ V and $R_{Bias} = 10.00$ KΩ. Inserting these values into Equation 5, $I_{BiasZTC}$ may be 79 $C0_H$.

The actual DAC value that may be used for a particular reader 75 depends on the reader calibration coefficients. The actual DAC value may be adjusted so that the effects of the non-ideal, such as 4.096 and 2.048 VDC references, 10.00KΩ resistor, op-amp input offset voltage and/or bias current of each particular reader 75 may be corrected. In some embodiments of the present invention, the reader calibration coefficients for the $I_{BiasZTC}$ current are "$I_{Bias\_Offset}$" and "$I_{Bias\_Gain}$" as may be stored in a memory location of the reader 75 and may be determined during factory calibration. The actual value written to a particular reader DAC may be calculated using Equation 6 set out below:

$$I_{bias-ztc_{reader(x)}} = I_{BiasZTC} * I_{Bias\_Gain} + I_{Bias\_Offset} \quad \text{(Equation 6)}$$

Table 5 of FIG. 39 includes exemplary V/I relationships of readers determined during calibration according to some embodiments of the present invention. It will be understood that the V/I relationships set out in Table 5 are provided for exemplary purposes only and embodiments of the present invention are not limited to this configuration.

In some embodiments of the present invention, the bias current accuracy for any individual reader 75 may be specified at about +/−100 nA. The trans-conductance of the RADFET may be specified at about 1/100KΩ max at the ZTC bias current. If the bias current changes between the "pre-radiation" and "post-radiation" dose readings due to, for example, switching readers, there may be a potential voltage error of about 100 nA * 100KΩ=10 mV. Since the initial sensitivity of the RADFET may be specified at about 0.25 mV/cGy, this represents a potential 40 cGy error. The specified error for the system may be about +/−1 cGy for a 20 cGy dose. The repeatability of the bias current (between "pre" and "post" dose measurements) on an individual reader 75 may be specified at about +/−1 nA so that the error due to a "trans-conductance effect" may be limited to about 1 nA * 100KΩ=100 μV.

The reader 75 may initially "zero" an un-dosed sensor patch 30 by adjusting the output of a digital to analog converter (DAC) so that the analog to digital (A/D) converter input is near zero. The DAC is the standardized bias current setting that may be used for the A/D readings for the pre-radiation and post-radiation threshold voltage measurements. The "zeroed" value may be stored in the electronic memory 67 and the patch status register may be updated to indicate that the patch has been "zeroed". The zeroing operation may limit the range of the RADFET bias current source. After the patch has been dosed and reinserted, the reader 75 may reset the DAC-B channel to a previous level using data stored in the memory location of the electronic memory 67 so that the voltage measured by the A/D converter may represent the shift in voltage due to radiation. The scaling may be arranged in hardware so that the voltage generated by the DAC-B is approximately ⅓ of the threshold voltage at the RADFET. The A/D conversion result and the standardized bias current (DAC or DAC-A) may be stored in cells of the electronic memory 67.

The Digital-to-Analog Converter (DAC) may provide two functions. The first is to establish the bias current in the RADFET based on a factory-derived bias current setting. This current may be established so that there is a minimum influence of temperature on the RADFET threshold voltage. The second DAC, OFFSET DAC, may provide a means to offset the RADFET initial threshold voltage in the "zeroing" procedure. In other words, prior to dosing, the patch may be zeroed by adjusting the OFFSET DAC so that the output of the summing amplifier is about 2.048V +/−100 mV when the patch RADFET is connected. The summing amplifier subtracts the voltage from the OFFSET DAC from the RADFET and applies the difference to the A/D Converter. This DAC setting may be stored in electronic memory 67 and reused after dose is applied to bias the RADFET. The difference in the pre-dose and post-dose RADFET threshold voltages measured by the A/D Converter may be used to calculate the measured dose.

The memory map may also include a memory cell including $T_{offset}$, which may be, for example, a byte representing the temperature at which the diode voltage of the RADFET may be measured. In some embodiments of the present invention, the offset may be based on a nominal temperature of about 27.0° C. Accordingly, if, for example, the actual temperature during the RADFET diode measurement (during the ZTC process) is 27.0° C., then the offset will be 00 h.

In some embodiments of the present invention, the diode voltage may be measured (at the $I_{Bias\_Diode}$ current) during ZTC processing and the voltage may be converted to hexadecimal notation using Equation 7 set out below.

$$V_{Diode@Temp} = 800000\ h + (2.048 - V_{Diode(measured)}) * 2^{24} / 4.096 \quad \text{(Equation 7)}$$

This value may be stored in memory locations of the memory map in the electronic memory 67.

As noted above, the MOSFET bias parameters, along with customized calibration coefficients, are stored in the EEPROM memory provided on each patch. The patch memory also includes a patch identifier or serial number, and instructions on how the reader interfaces with the patch. Provision of these instructions allows the reader to work with multiple generations of patches without necessitating upgrades to the reader. The patch memory also stores the detected and calculated radiation dosages, the date and time of the treatment, and a clinician-entered patient identifier and/or record number. After use, the patch can be placed in the patient file or medical record to form a part of the archived patient treatment history, or may be discarded.

FIGS. 24A and 24B illustrate alternate embodiments of MOSFET based circuits 30c. Each circuit 30c employs a RADFET pair 63p (FIG. 24A), 63p' (FIG. 24B) as the radiation sensitive device 63. The configuration on the left of each of these figures illustrates the irradiation configuration and the configuration on the right illustrates the read dose configuration. In the embodiment shown in FIG. 24A, the RADFET pair 63p are differentially biased during irradiation to create different voltage offsets. Each of the RADFETs in the pair $63p_1$, $63p_2$ can be differentially biased during radiation to generate different voltage offsets when exposed to radiation. Using a pair of RADFETS can reduce the influence of temperature in the detected voltage shift value. In particular embodiments, the RADFET pair can be matched (such as taken from the same part of the substrate during fabrication) to reduce drift effects (Vth drift). In certain embodiments, the voltage reading can be obtained with a zero bias state, and/or without requiring wires during radiation, and/or without requiring a floating gate structure.

In the embodiment shown in FIG. 24B, one of the RADFETs $63p_1'$ in the pair 63p is selectively implanted with dopant ions to shift the threshold voltage (Vth) of that RADFET with respect to the other RADFET $63p_2'$. The ion implantation can be carried out in various manners as known to those of skill in the art, such as by masking one of the FETs with photoresist to inhibit ions from entering into the gate region. As is well known, using the proper implant species and/or dopant material can increase the FET sensitivity to radiation effects. In certain embodiments of the present invention, a MOSFET (RADFET) pair is used to effectively provide "differential biasing" without the need to apply an external voltage and without the need for a floating gate structure. That is, the MOSFETs can be configured to be individually unbiased and readings of the two MOSFETs (one at a different threshold voltage value) generates the differential biasing. In particular embodiments, this radiation sensitive MOSFET pair configuration that does not require floating gate structures and/or external voltage can be used in implantable as well as skin mounted sensors, such as in implantable sensors used as described in U.S. Pat. No. 6,402,689 to Scarantino et al.

Figure 25A:
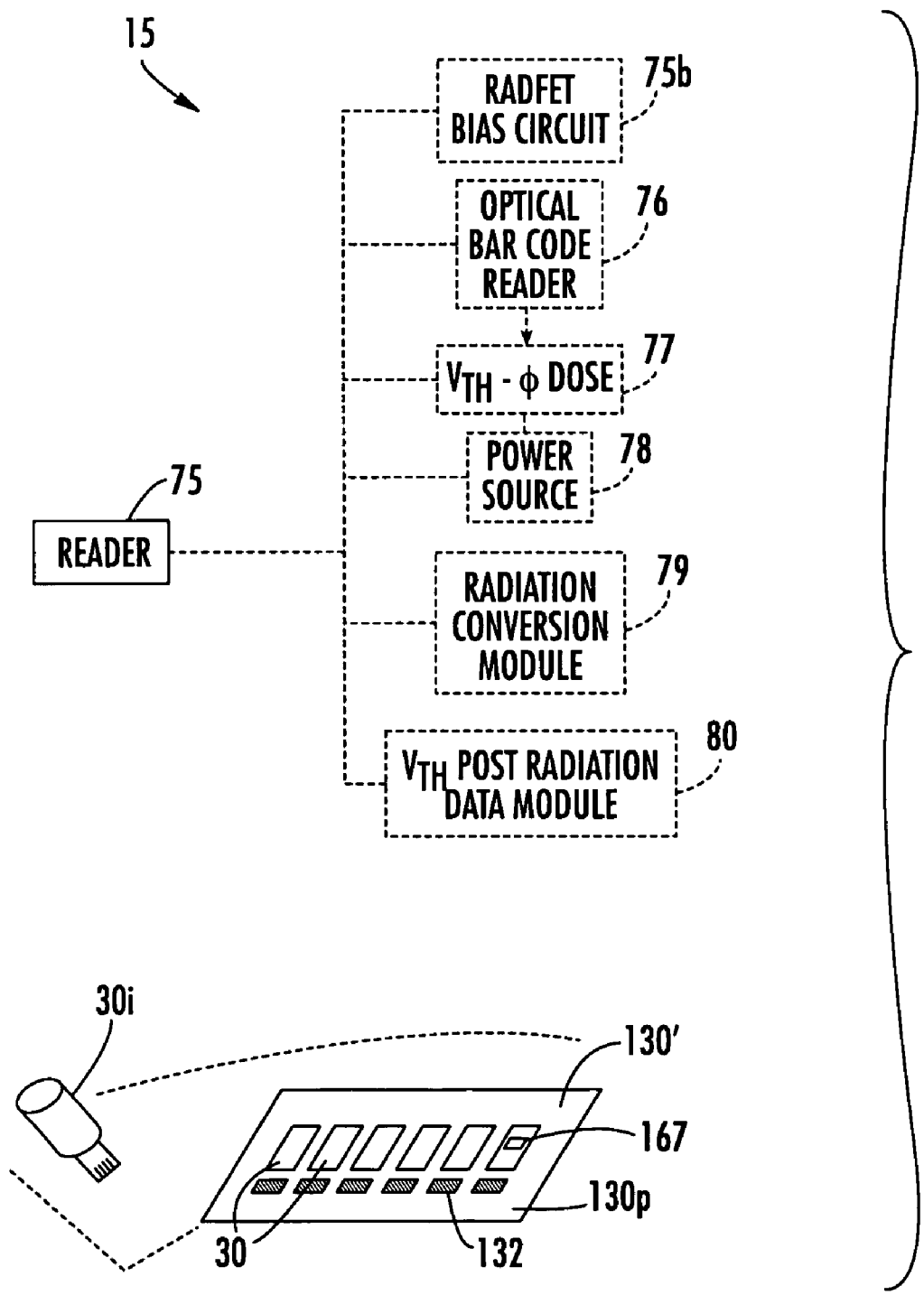
FIG. 25A is a schematic diagram of a system or computer program product for estimating radiation based on data taken from a point contact-reader data acquisition system according to still further embodiments of the present invention.
Figure 25B:
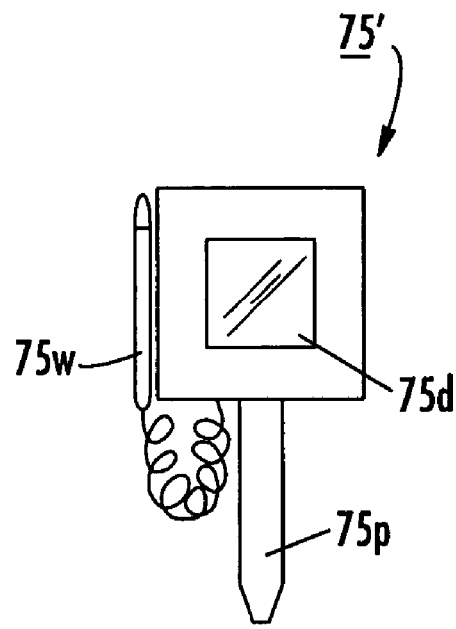
FIG. 25B is a schematic diagram illustrating a reader device according to some embodiments of the present invention.
Figure 25C:
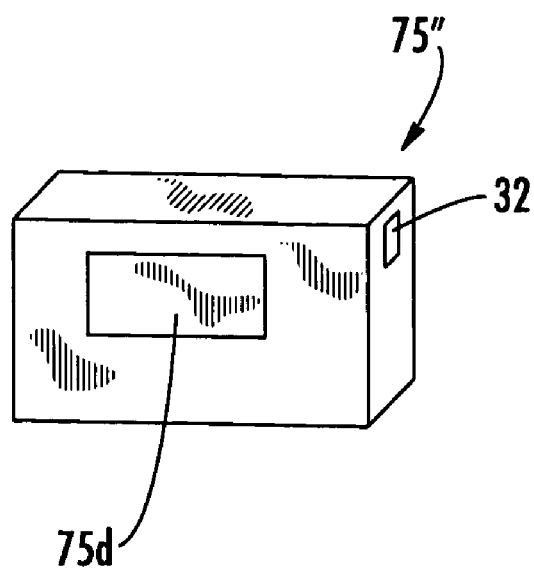
FIG. 25C is a schematic diagram illustrating a reader device according to further embodiments of the present invention.

FIG. 25A illustrates embodiments of a radiation dose evaluation system 15 according to embodiments of the present invention. As shown, the system 15 includes a reader 75 and a set of sensor patches 130' and an internal dosimeter 30i. The reader 75 may include, for example, the reader 75 of FIG. 17A. The sensor patches 30 can be arranged as a strip of patches 30 held in a single-patient sized package 130p. The reader 75 can include a RADFET bias circuit 75b. In certain embodiments, the reader 75 is a portable flat pocket or palm size reader that a clinician can carry relatively non-obtrusively in his/her pocket or a similar sized casing.

As shown by the dotted line boxes in FIG. 25A, the reader 75 may hold a power source 78 and plurality of operational software modules including: an optical bar code reader module 76, a zero-dose threshold voltage data module 77, a radiation dose conversion module (based on a predetermined voltage threshold to radiation dose response curve) 79, and a threshold voltage post radiation data module 80.

In some embodiments, in operation, the reader 75 can be configured to supply a bias current to the RADFET by attaching to the sensor patch 30 and electrically contacting the conductive probe region 30p or the electrical contacts 31. The reader 75 can measure the voltage shift response of the RADFET on the sensor patch 30 and calculate radiation dose based on the shift and the dose conversion algorithm. The reader 75 can display the results to the clinician (such as on an integrated LCD screen 75d incorporated into the body of the reader) and may be configured to download or upload the data to another device (such as a computer or computer network) for electronic record generation or storage.

The reader may include an electronic memory map identifying memory locations and contents thereof. In some embodiments of the present invention, the memory map may resemble a spreadsheet. The memory map may include one or more fields containing data, such as serial numbers, revision number, reader calibration data, A/D gain correction, A/D offset correction, D/A gain correction, D/A offset correction, hospital ID and the like. In some embodiments of the present invention, the reader memory may be large enough to store at least 100, typically about 250 dose records of about 64 bytes each. The dose record may include items listed in Table 6 of FIG. 40. It will be understood that the dose record of FIG. 40 is provided for exemplary purposes only and embodiments of the present invention should not be limited to this configuration. Details with respect to memory maps will be understood by those having skill in the art and will not be discussed further herein.

The dose amount can be calculated for each sensor 30c and/or dosimeter 30i used. In particular embodiments, the system can be configured to generate an average or weighted average of the dose amount determined over a plurality of the patches. In certain embodiments, where there is a large variation in values (or if it departs from a statistical norm or predicted value) the system can be configured to discard that sensor value or to alert the clinician of potential data corruption. Of course, much smaller values are predicted in sensitive areas away from the targeted zone and the system can be configured to evaluate whether the sensor is in a primary location or in a secondary zone as regards the radiation path.

It is noted that features described with respect to one embodiment of the sensor, reader and/or system may be incorporated into other embodiments and the description and illustrations of such features are not be construed as limited to the particular embodiment for which it was described.

As will be appreciated by one of skill in the art, the present invention may be embodied as a method, data or signal processing system, or computer program product. Accordingly, the present invention may take the form of an entirely hardware embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as LABVIEW, Java®, Smalltalk, Python, or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Figure 26:
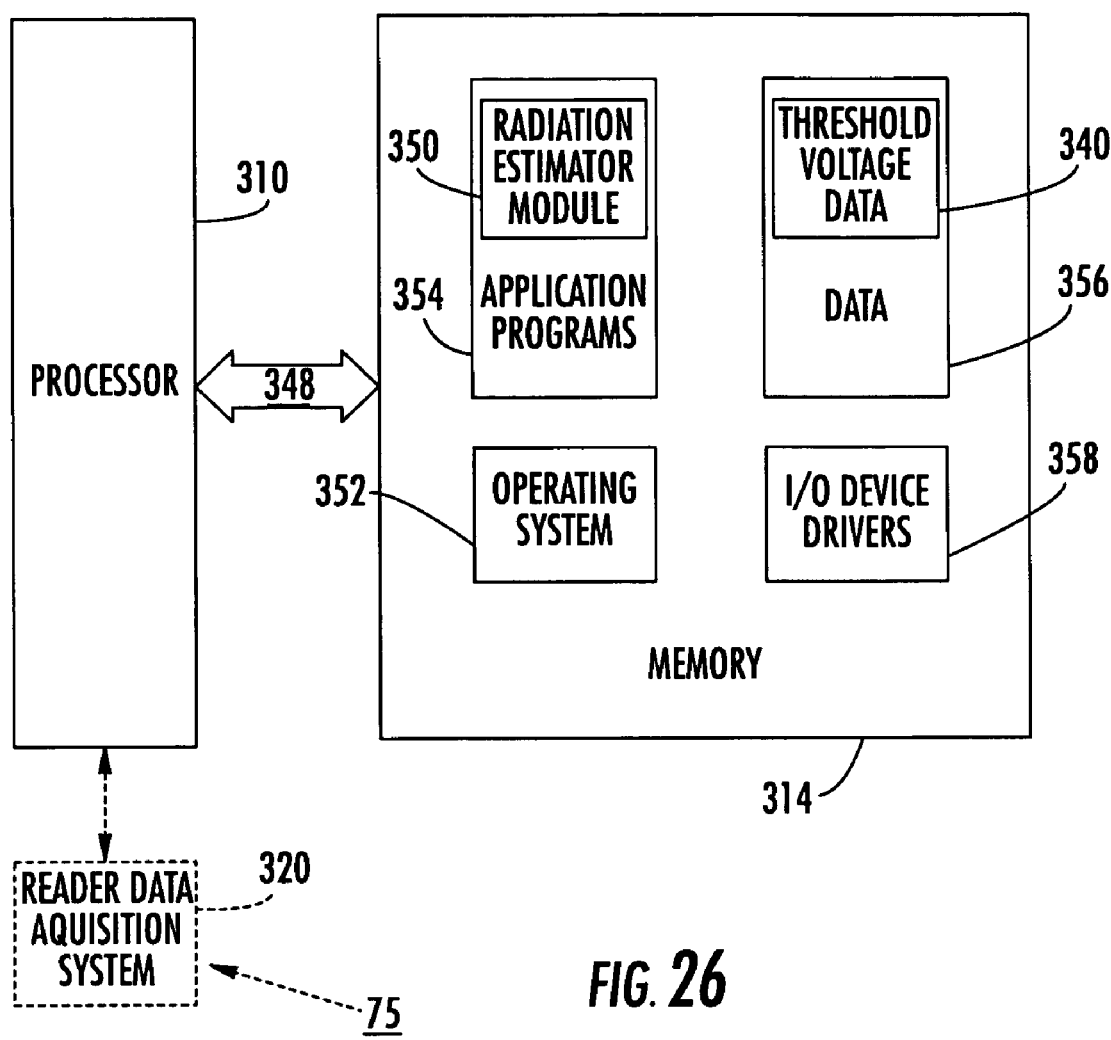
FIG. 26 is a block diagram of a computer program having a radiation estimation module according to still further embodiments of the present invention.

FIG. 26 is a block diagram of exemplary embodiments of data processing systems that illustrate systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system. The memory 314 can include, but is not limited to, the following types of devices: cache, ROM, PROM, EPROM, EEPROM, flash memory, SRAM, and DRAM.

As shown in FIG. 26, the memory 314 may include several categories of software and data used in the data processing system 305: the operating system 352; the application programs 354; the input/output (I/O) device drivers 358; a radiation estimator module 350; and the data 356. The data 356 may include threshold voltage data 340 (zero dose and post irradiation dose levels) which may be obtained from a reader data acquisition system 320. As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98, Windows2000 or Windows XP from Microsoft Corporation, Redmond, Wash., Unix or Linux or FreeBSD, Palm OS from Palm, Inc., Mac OS from Apple Computer, or proprietary operating systems. The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and preferably include at least one application that supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the radiation estimator module 350 being an application program in FIG. 26, as will be appreciated by those of skill in the art, other configurations may also be utilized while still benefiting from the teachings of the present invention.

For example, the radiation estimation module 350 may also be incorporated into the operating system 352, the I/O device drivers 358 or other such logical division of the data processing system. Thus, the present invention should not be construed as limited to the configuration of FIG. 26, which is intended to encompass any configuration capable of carrying out the operations described herein.

In certain embodiments, the radiation estimation module 350 includes computer program code for estimating radiation dose based on the measured threshold voltage shift. The I/O data port can be used to transfer information between the data processing system and the reader data acquisition system 320 or another computer system or a network (e.g., the Internet) or to other devices controlled by the processor. These components may be conventional components such as those used in many conventional data processing systems that may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configurations illustrated in the figures but is intended to encompass any configuration capable of carrying out the operations described herein.

The flowcharts and block diagrams of certain of the figures herein illustrate the architecture, functionality, and operation of possible implementations of radiation detection means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 27:
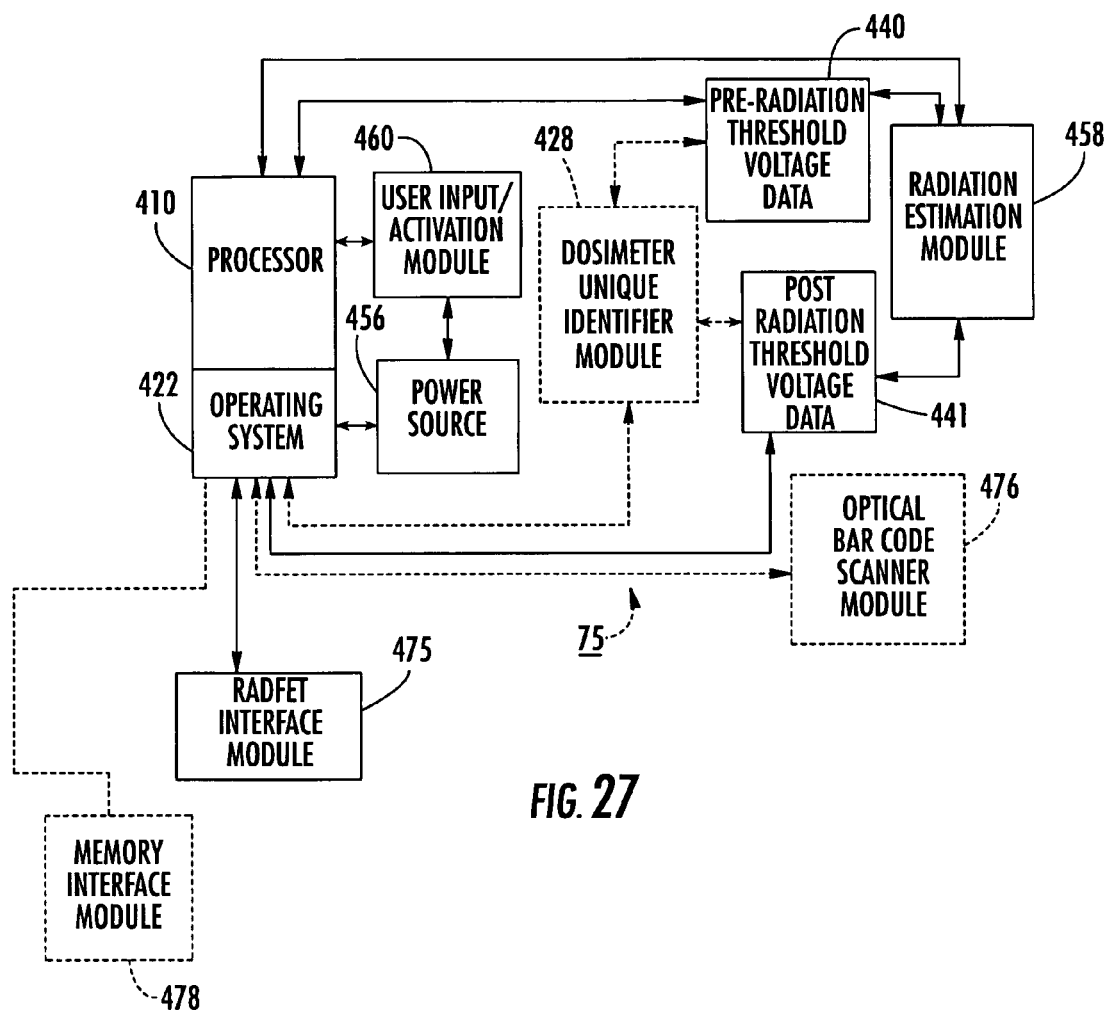
FIG. 27 is a block diagram of a point-contact reader data acquisition system some according to embodiments of the present invention.

FIG. 27 is a block diagram illustration of one embodiment of a reader 75 according to the present invention. As shown, the reader 75 includes an operating system 422, a processor 410, a power source 456, and a user activation/input module 460. The reader 75 can also include a RADFET interface module 475 and a sensor patch memory interface module 478. The reader 75 may communicate with the sensor patch memory using, for example, a standard 12C protocol and in some embodiments may use a clock as a data line. As discussed above, in certain embodiments, the sensor patch 30 may be configured to communicate wirelessly with the reader 75. In these embodiments, the interface module 475 may be configured to receive wireless signals from the sensor patch 30. The reader 75 may optionally include a sensor patch identifier module 428 to track which sensor patch 30 has a particular radiation dose result. The identifier module 428 may allow the user to input via an input keypad associated with the reader, an alphanumeric identifier (F1, B1, etc.) for a particular sensor patch prior to obtaining the reading, or a bar code identifier or other automated identifier means can be used (such as scanning a bar code label on the sensor and the like).

The reader 75 also includes pre-radiation (zero dose) threshold voltage data 440, post radiation threshold voltage data 441, and a radiation estimation module 458. The pre-radiation threshold voltage data 440 and the post radiation threshold data 441 may be obtained when the MOSFET is biased with the zero temperature bias current discussed above. The zero temperature bias current may be obtained before the administration of the radiation therapy, stored in the sensor patch memory 67 (FIG. 21) and obtained by the reader using the sensor patch memory interface module 478. The radiation estimation module 458 may also be configured to extrapolate to arrive at the radiation dose delivered to the tumor site. In some embodiments of the present invention, the radiation estimation module 458 may be further configured to prompt a doctor or technician for predetermined data needed to calculate or estimate the radiation dose. The predetermined data may include conversion factors and/or correction factors associated with different versions of the sensor patches. As shown, the reader 75 may also include an optical bar code scanner module 476 to allow the reader to input the characterizing zero dose threshold voltage values by optically reading same. Similarly, calibration data can be entered via the bar the bar code scanner 476 or memory 67 from the patches 30. Alternatively, the clinician can enter the desired data in situ as desired.

Tables 8 and 9 of FIGS. 42A, 42B and 43 contain a listing the functional specification of readers and sensor patches, respectively, according to some embodiments of the present invention. It will be understood that the functional specifications listed in FIGS. 42A, 42B and 43 are provided for exemplary purposes only and that embodiments of the present invention are not limited to this configuration.

Although primarily described for oncologic therapies, the devices can be used to monitor other radiation exposures, particularly exposures during medical procedures, such as fluoroscopy, brachytherapy, and the like.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for monitoring radiation exposure for a patient undergoing a medical procedure, comprising:

inserting a single-use dosimeter into a patient, wherein the at least one dosimeter comprises at least one radiation sensor circuit with a MOSFET and electronic memory that holds calibration data for the MOSFET;

exposing the patient to radiation in a medical procedure during a treatment session;

transmitting data from the dosimeter to a dose-reader device after the exposing step, the transmitting data comprising the calibration data and data associated with a change in an operational parameter in the MOSFET of the dosimeter radiation sensor circuit;

removing the dosimeter from the patient after the exposing step during or proximate in time to the treatment session; and determining a radiation dose received by the patient during the exposing step based on the change in the operational parameter of the MOSFET and the calibration data.

2. A method according to claim 1, wherein the at least one radiation sensor circuit includes a single operative MOSFET that is unbiased and unpowered during irradiation.

3. A method according to claim 1, wherein the transmitting data is carried out after the dosimeter is removed from the patient by inserting a tab extending from the at least one dosimeter into a port in the dose-reader device.

4. A method according to claim 1, further comprising transmitting the determined radiation dose from the dose-reader to the at least one dosimeter and storing the determined radiation dose on the electronic memory that is integrated with the at least one dosimeter.

5. A method according to claim 1, further comprising storing a plurality of patient specific data records on the reader, then transmitting the radiation data obtained by the reader from the at least one dosimeter to a remote computer.

6. A method according to claim 1, further comprising sterilizing the single-use dosimeter and packaging the single-use dosimeter in a sterile package suitable for human medical use.

7. A method according to claim 1, wherein the at least one dosimeter is held in and/or on a mouthpiece, and wherein the inserting step comprises placing the mouthpiece in the mouth of the patient.

8. A method according to claim 7, wherein the mouthpiece is a bite block that includes an outwardly extending tab portion, and wherein the transmitting data step comprises engaging a portable reader with the tab portion to electronically engage the reader with the radiation sensor circuit and the electronic memory.

9. A method according to claim 1, wherein the at least one dosimeter is held in a generally conformable nose cavity plug, and wherein the inserting step comprises inserting the plug into a nasal cavity.

10. A method according to claim 9, wherein the nose cavity plug includes an outwardly extending tab portion, and wherein the transmitting data step comprises engaging a portable reader with the tab portion to electronically engage the reader with the radiation sensor circuit and the electronic memory after the exposing step.

11. A method according to claim 1. wherein the at least one dosimeter is held in a generally conformable ear plug, and wherein the inserting step comprises inserting the plug into an ear canal or cavity of the patient.

12. A method according to claim 11, wherein the ear plug includes an outwardly extending tab portion, and wherein the transmitting data step comprises engaging a portable reader with the tab portion to electronically engage the reader with the radiation sensor circuit and the electronic memory after the exposing step.

13. A method according to claim 12, wherein the at least one dosimeter is configured such that at least one dosimeter is held by two different ear plugs, and wherein the step of inserting comprises inserting the plugs into both a right and a left ear canal of the patient.

14. A method according to claim 1, wherein the at least one dosimeter is held in and/or on a flexible male genourinary catheter.

15. A method according to claim 14, wherein the dosimeter comprises a flex circuit with a MOSFET held at a distal end portion of the catheter and an external outwardly extending tab portion located at a proximal end portion of the catheter, and wherein the transmitting data step comprises engaging a portable reader with the tab portion to electronically engage the reader with the radiation sensor circuit and the electronic memory after the exposing step.

16. A method according to claim 14, wherein the inserting step is carried out so that the MOSFET in at least one of the at least one radiation sensor circuit is disposed proximate a prostate of a male patient.

17. A method according to claim 16, wherein the exposing step is carried out during brachytherapy or external radiation beam therapy.

18. A method according to claim 1, wherein the at least one dosimeter is held in and/or on a flexible female genourinary probe.

19. A method according to claim 18, wherein the at least one dosimeter is held in a vaginal probe.

20. A method according to claim 18, wherein the at least one dosimeter is held in a urethral probe.

21. A method according to claim 18, wherein the at least one dosimeter includes an outwardly extending tab portion, and wherein the transmitting data step comprises engaging a portable reader with the tab portion to electronically engage the reader with the radiation sensor circuit and the electronic memory after the exposing step.

22. A method according to claim 1, wherein the at least one dosimeter is held in or on a rectal probe.

23. A method according to claim 22, wherein the rectal probe includes an outwardly extending tab portion, and wherein the transmitting data step comprises engaging a portable reader with the tab portion to electronically engage the reader with the radiation sensor circuit and the electronic memory after the exposing step.

24. A method according to claim 1, wherein the exposing step is carried out during a high-dose rate brachytherapy using a plurality of catheters having an open end to slidably receive the dosimeter, the catheters held in a transcutaneous geometric matrix with a radioactive Ir-192 source that travels in the open catheters into the patient, and wherein the inserting step comprises placing the dosimeter inside at least one of the open catheters.

25. A method according to claim 24, wherein the dosimeter includes an outwardly extending tab portion, and wherein the transmitting data step comprises engaging a portable reader with the tab portion to electronically engage the reader with the radiation sensor circuit and the electronic memory after the exposing step.

26. A method according to claim 1, wherein the at least one dosimeter is a plurality of dosimeters spaced apart in a lengthwise direction, each having a respective radiation sensor circuit with a single operative MOSFET, and wherein the determining step comprises determining a radiation dose for each of the radiation sensor circuits to provide a plurality of dose readings at different internal depths associated with the exposing step.

27. A method according to claim 1, further comprising positioning at least one substantially conformable skin-mounted single-use dosimeter patch on the patient, the at least one surface mount dosimeter patch comprising a flex circuit with a radiation sensor circuit having an unbiased MOSFET and electronic memory configured to hold calibration data for the radiation sensor circuit.

28. A method according to claim 27, further comprising transmitting data from the at least one surface mount patch to the dose-reader device after the exposing step to obtain the calibration data and data associated with a change in an operational parameter in the MOSFET of the dosimeter radiation sensor circuit to determine radiation received by the patient during the exposing step based on the change in the operational parameter of the MOSFET and the calibration data.

29. A method according to claim 1, wherein the transmitting step further comprises electronically transmitting measurement methodology instructions to the reader from the dosimeter on how to communicate with the dosimeter.

30. A method according to claim 29, further comprising storing the determined radiation dose in the memory of the dosimeter after the determining step.

31. A method according to claim 1, wherein the transmitting step further comprises transmitting a type of internal dosimeter the dosimeter is to the reader.

32. A system for monitoring radiation administered to a patient during a diagnostic and/or therapeutic treatment, the system comprising:
at least one single-use internal dosimeter, the internal dosimeter comprising at least one radiation sensor circuit comprising a MOSFET having an associated threshold voltage that changes when exposed to radiation and electronic memory comprising calibration data for determining radiation dose; and
a portable dose-reader configured to obtain voltage threshold data and calibration data from the at least one internal dosimeter after the single-use dosimeter has been exposed to radiation corresponding to a dose amount of radiation exposure received during irradiation exposure.

33. A system according to claim 32, wherein the at least one internal dosimeter comprises at least one contact region that is configured and sized to enter a port in the dose-reader to transmit the voltage threshold data and the calibration data.

34. A system according to claim 32, wherein the dose reader is sized and configured as a handheld and/or pocket-sized portable reader.

35. A system according to claim 32, wherein the dose-reader is configured to obtain data from the internal dosimeter and from a substantially conformable single-use skin mounted dosimeter patch and determine radiation dose at a monitored location of the patient from each type of dosimeter.

36. A system according to claim 32, wherein the internal dosimeter is sized and configured as a natural body lumen and/or cavity probe.

37. A system according to claim 36, wherein the internal dosimeter is integrated in and/or on a mouthpiece.

38. A system according to claim 37, wherein the reader further comprises a computer readable storage medium having computer readable program code embodied in the medium, the computer readable program code comprising computer program code for identifying what type of dosimeter is undergoing evaluation from a plurality of differently configured dosimeters configured to be evaluated by the dose reader.

39. A system according to claim 38, wherein the reader comprises a computer readable storage medium having computer readable program code embodied in the medium, the computer readable program code comprising computer program code that prompts a user to identify the dosimeter configuration being evaluated.

40. A system according to claim 38, wherein the reader automatically identifies the type of dosimeter based on data in the electronic memory of the dosimeter.

41. A system according to claim 37, wherein the mouthpiece is a bite block that includes an externally extending tab portion, and wherein the tab portion is configured to electronically engage the reader with the radiation sensor circuit and the electronic memory.

42. A system according to claim 36, wherein the internal dosimeter is configured as a generally conformable nose cavity plug.

43. A system according to claim 42, wherein the nose cavity plug includes a tab portion that is configured to engage the portable reader to electronically engage the reader with the radiation sensor circuit and the electronic memory.

44. A system according to claim 36, wherein the internal dosimeter is configured as a generally conformable ear plug.

45. A system according to claim 44, wherein the ear plug includes an outwardly extending tab portion that is configured to electronically engage the portable reader with the radiation sensor circuit and the electronic memory.

46. A system according to claim 36, wherein the probe is a catheter, and wherein the at least one dosimeter is held in and/or on a flexible male genourinary catheter.

47. A system according to claim 46, wherein the dosimeter comprises a flex circuit with a MOSFET held at a distal end portion of the catheter and a tab portion located at a proximal end portion of the catheter that is configured to electronically engage the portable reader with the radiation sensor circuit and the electronic memory.

48. A system according to claim 46, wherein the at least one dosimeter is a plurality of dosimeters each having an associated radiation sensor circuit with a MOSFET, the dosimeters configured so that the MOSFETS are held spaced apart in a lengthwise direction on a flex circuit, and wherein the catheter comprises an expandable balloon that expands above a male urinary sphincter and holds the catheter in position during irradiation so that the MOSFET in at least one of the at least one radiation sensor circuits is configured to reside proximate a prostate of a male patient above the urinary sphincter.

49. A system according to claim 48, wherein the flex circuit is configured to be slidably received in the catheter to allow in situ axially adjustable placement of at least one of the radiation sensor circuits.

50. A system according to claim 48, wherein the dosimeter is configured to obtain radiation data during brachytherapy and/or external radiation beam therapy.

51. A system according to claim 36, wherein the at least one dosimeter is held in and/or on a flexible female genourinary probe.

52. A system according to claim 51, wherein the probe is configured as a vaginal probe.

53. A system according to claim 51, wherein the probe is configured as a urethral probe.

54. A system according to claim 51, wherein the dosimeter includes a tab portion configured to engage the portable reader to electronically engage the reader with the radiation sensor circuit and the electronic memory.

55. A system according to claim 36, wherein the dosimeter configured as a rectal probe.

56. A system according to claim 55, wherein the rectal probe includes an outwardly extending tab portion configured to electronically engage a portable reader with the radiation sensor circuit and the electronic memory.

57. A system according to claim 32, wherein the internal dosimeter is sized and configured as a transcutaneous probe.

58. A system according to claim 57, wherein the at least one dosimeter is sized and configured to be received in at least one of a plurality of catheters having an open end and being held in a transcutaneous geometric matrix during HDR (high dose rate) brachytherapy to provide radiation dose estimates of a radioactive source that travels in the open catheters into the patient.

59. A system according to claim 58, wherein the dosimeter includes an outwardly extending tab portion configured to engage a portable reader to electronically engage the reader with the radiation sensor circuit and the electronic memory, wherein the dosimeter is self-contained and unpowered during exposure to radiation.

60. A system according to claim 32, wherein the at least one dosimeter is a plurality of dosimeters held spaced apart in a lengthwise direction on a common flex circuit in a common probe body, each having a respective radiation sensor circuit with a single operative MOSFET, wherein the different dosimeters are configured to provide radiation data for a plurality of axially spaced apart subsurface depth locations.

61. A system according to claim 32, wherein the calibration data comprises data associated with a zero temperature coefficient of the MOSFET for radiation quantification.

62. A system according to claim 32, wherein the electronic memory is configured to store radiation data and patient information.

63. A system according to claim 32, wherein the at least one dosimeter is biocompatible and sterilized and held in a package for medical use.

64. A system according to claim 32, wherein the reader comprises computer program code for prompting a clinician to enter calibration data associated with a particular patient and medical procedure and computer program code for determining radiation exposure received by the patient whereby the reader can calculate the radiation dose for both a surface dosimeter and at least one internal dosimeter.

65. A system according to claim 64, wherein the reader comprises computer program code for prompting a user to select the type of radiation dosimeter being evaluated from a predetermined list of dosimeter types including external and internal dosimeter configurations.

66. An internal dosimeter according to claim 32, wherein the dosimeter is sized and configured to be slidably received in at least one of a plurality of catheters having an open end and held in a transcutaneous geometric matrix during HDR (high dose rate) brachytherapy to provide radiation dose estimates of a radioactive source that travels in the open catheters into the patient.

67. An internal dosimeter according to claim 66, wherein the dosimeter includes an outwardly extending tab portion that defines the reader contact zone and is configured to enter a port in the portable reader to electronically engage the reader with the radiation sensor circuit and the electronic memory.

68. An internal dosimeter according to claim 67, wherein the dosimeter comprises a plurality of radiation sensor circuits on a common flex circuit, each circuit having a respective single operative MOSFET with each MOSFET held spaced apart in a lengthwise direction on the dosimeter and being configured to provide dose data associated with a plurality of different internal depth locations.

69. A system according to claim 32, wherein the dosimeter memory includes instructions to tell the reader how to electronically communicate with the dosimeter.

70. A system according to claim 32, wherein the reader is configured to calculate the radiation dose and transmit the calculated radiation dose to the dosimeter memory for electronic storage.

* * * * *